(12) United States Patent
Ueno

(10) Patent No.: US 11,643,432 B2
(45) Date of Patent: May 9, 2023

(54) NUCLEOSIDE DERIVATIVE AND USE THEREOF

(71) Applicant: NATIONAL UNIVERSITY CORPORATION TOKAI NATIONAL HIGHER EDUCATION AND RESEARCH SYSTEM, Nagoya (JP)

(72) Inventor: Yoshihito Ueno, Gifu (JP)

(73) Assignee: NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 747 days.

(21) Appl. No.: 16/470,339

(22) PCT Filed: Dec. 14, 2017

(86) PCT No.: PCT/JP2017/044995
§ 371 (c)(1),
(2) Date: Jun. 17, 2019

(87) PCT Pub. No.: WO2018/110678
PCT Pub. Date: Aug. 21, 2018

(65) Prior Publication Data
US 2021/0371447 A1 Dec. 2, 2021

(30) Foreign Application Priority Data
Dec. 16, 2016 (JP) .............................. JP2016-244916

(51) Int. Cl.
*C07H 19/10* (2006.01)
*C12N 15/113* (2010.01)

(52) U.S. Cl.
CPC ............ *C07H 19/10* (2013.01); *C12N 15/113* (2013.01); *C12N 2310/141* (2013.01); *C12N 2310/322* (2013.01)

(58) Field of Classification Search
CPC ........................................................ C07H 9/10
See application file for complete search history.

(56) References Cited

U.S. PATENT DOCUMENTS

| | | |
|---|---|---|
| 5,446,137 A | 8/1995 | Maag et al. |
| 5,681,940 A | 10/1997 | Wang et al. |
| 5,712,378 A | 1/1998 | Wang |
| 6,191,266 B1 | 2/2001 | Wang |
| 6,743,902 B1 | 6/2004 | Wang |
| 2005/0214901 A1* | 9/2005 | Ealick ............... A61K 47/67 435/69.1 |
| 2015/0105341 A1* | 4/2015 | Beigelman ......... C07H 19/11 514/47 |

(Continued)

FOREIGN PATENT DOCUMENTS

| | | |
|---|---|---|
| JP | H05-148293 A | 6/1993 |
| JP | H10-506915 A | 7/1998 |
| JP | H11-130793 A | 5/1999 |

(Continued)

OTHER PUBLICATIONS

Pfundheller et al.; "Oligonucleotides Containing Novel 4'-C- or 3'-C-(Aminoalkyl)-Branched Thymidnes);" Helvetica Chimica Acta; 2000; pp. 128-151; vol. 83.

Gore et al.; "Synthesis, Gene, Silencing, and Molecular Modeling Studies of 4'-C- Aminomethyl-2'-O-methyl Modified Small Interfering RNAs;" The Journal of Organic Chemistry; 2012; pp. 3233-3245; vol. 77.

Pfundheller et al.; "Oligonucleotides Containing 4'-C-Aminomethyl-2'-Modified Thymidines Show Increased Binding Affinity Towards DNA and RNA;" Bioorganic & Medicinal Chemistry Letters; 1999; pp. 2667-2672; vol. 9.

(Continued)

*Primary Examiner* — Brian Whiteman
(74) *Attorney, Agent, or Firm* — Oliff PLC

(57) ABSTRACT

A nucleoside derivative represented below, or a salt thereof.

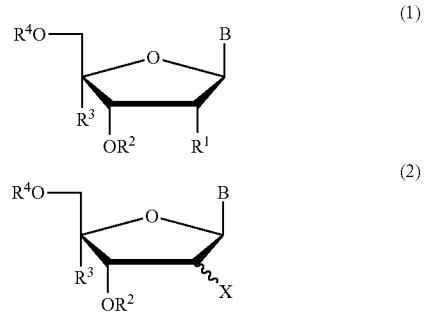

(In (1), $R^1$ represents a hydrogen atom, a hydroxyl group or a protected group, and in (2), X represent a halogen atom. In (1) and (2), $R^2$ and $R^4$ each represent a hydrogen atom, a hydroxyl protecting, phosphate, or protected phosphate group, or —P(=O)$_n$R$^5$R$^6$ (n is 0 or 1, $R^5$ and $R^6$ each representing a hydrogen atom, hydroxyl, protected hydroxyl, mercapto, protected mercapto, lower alkoxy, cyano lower alkoxy, amino or substituted amino group, when n is 1, $R^5$ and $R^6$ are not both hydrogen atoms), $R^3$ represents NHR$^7$ ($R^7$ represents a hydrogen atom, alkyl, alkenyl or protecting group for an amino group), an azide, amidino or guanidino group, each having a linking group (when $R^7$ is hydrogen atom, the linking group is an alkylene group), and B represents any of a purine-9-yl, 2-oxopyrimidin-1-yl, substituted purine-9-yl or substituted 2-oxopyrimidin-1-yl group).

7 Claims, 9 Drawing Sheets
Specification includes a Sequence Listing.

(56) References Cited

U.S. PATENT DOCUMENTS

2015/0337002 A1  11/2015  Obika et al.

FOREIGN PATENT DOCUMENTS

| JP | 2000-512853 | A | | 10/2000 | |
|---|---|---|---|---|---|
| JP | 2005-533517 | A | | 11/2005 | |
| WO | 94/22454 | A1 | | 10/1994 | |
| WO | 97/048714 | A1 | | 12/1997 | |
| WO | 2004/011647 | A1 | | 2/2004 | |
| WO | 2014/112463 | A1 | | 7/2014 | |
| WO | WO-2015038596 | A1 | * | 3/2015 | ......... A61K 31/7068 |
| WO | 2015/200219 | A1 | | 12/2015 | |
| WO | WO-2016106050 | A1 | * | 6/2016 | ......... A61K 31/7068 |
| WO | WO-2017024310 | A1 | * | 2/2017 | ............ A61P 31/12 |

OTHER PUBLICATIONS

Gore et al.; "Influence of 2'-Fluoro versus 2'-O-Methyl Substituent on the Sugar Puckering of 4'-C-Aminomethyluridine," The Journal of Organic Chemistry; 2013; pp. 9956-9962; vol. 78.
Prakash et al.; "Identification of metabolically stable 5'-phosphate analogs that support single-stranded siRNA activity;" Nucleic Acids Research; 2015; pp. 2993-3011; vol. 43, No. 6.
Wang et al.; "Biophysical and Biochemical Properties of Oligodeoxy-Nucleotides Containing 4'-C- and 5'-C-Substituted Thymidines;" Bioorganic & Medicinal Chemistry Letters; 1999; pp. 885-890; vol. 9.
Wang et al.; 5'-C-Branched Thymidines: Synthesis, Stereochemistry, and Incorporation Into Oligodeoxynucleotides Tetrahedron Letters; 1996; pp. 2739-2742; vol. 37, No. 16.
Hampton et al.; "Design of Substrate-Site-Directed Irreversible Inhibitors of Adenosine 5'-Phosphate Aminohydrolase. Effect of Substrate Substituents on Affinity for the Substrate Site;" Journal of Medicinal Chemistry; 1976; pp. 1029-1033; vol. 19, No. 8.
Kajino et al.; "Synthesis and evaluation of siRNA containing aminoalkyl modified nucleosides;" Lecture abstracts of annual conference of Nucleic Acids Therapeutics Society of Japan; 2018; pp. 81; vol. 4.
Kajino et al.; "Synthesis and Properties of siRNA Containing 5'-C-Aminopropyl-2'-O-methyl-nucleosides;" Lecture proceedings of the spring annual conference of the Chemical Society of Japan; 2018; vol. 98.
Kajino et al.; "Synthesis and Property of 5'-C-Aminoalkyl-modified siRNA;" Program & Abstracts, International Symposium on Nucleic Acids Chemistry; 2017; pp. 142-143; vol. 44.
Kajino et al.; "Synthesis and characteristics of saccharide 5'-aminoalkyl-modified siRNA;" Annual Meeting of Union of Chemistry-Related Societies in Chubu Area, Japan; 2017; p. 81; vol. 48.
Dec. 18, 2018 International Search Report issued in International Patent Application No. PCT/JP2018/040544.

Morita et al.; "Synthesis and Properties of 2'-O,4'-C-Ethylene-Bridged Nucleic Acids (ENA) as Effective Antisense Oligonucleotides"; Bioorganic & Medicinal Chemistry; 2003; pp. 2211-2226; vol. 11.
Jun. 13, 2019 International Preliminary Report on Patentability issued in International Patent Application No. PCT/JP2018/040544.
Pfundheller et al.; "Oligonucleotides Containing Novel 4'-C- or 3'-C-(Aminoalkyl)-Branched Thymidines[1])"; Helvetica Chimica Acta; 2000; pp. 128-151; vol. 83.
Gore et al.; "Synthesis, Gene Silencing, and Molecular Modeling Studies of 4'-C-Aminomethyl-2'-O-methyl Modified Small Interfering RNAs"; The Journal of Organic Chemistry; vol. 77; 2012; pp. 3233-3245.
Ueno, Y. and Matsuda, M.; "Synthesis of Oligonucleotides Modified with Polyamines and Their Properties as Antisense and Antigene Molecules."; Journal of Synthetic Organic Chemistry; vol. 61; 2003; 890-899.
Atsumi et al.; "Nucleosides and Nucleotides. Part 214: Thermal Stability of Triplexes Containing 4'a-C-Aminoalkyl-2'-deoxynucleosides"; Bioorganic & Medicinal Chemistry; vol. 10; 2002; pp. 2933-2939.
Ueno et al.; "Nucleosides and Nucleotides. Part 206: Introduction of Lipophilic Groups into 4'a-C-(2-Aminoethyl) thymidine-Containing Phosphodiester Oligodeoxynucleotides and Thermal Stabilities of the Duplexes"; Tetrahedron; vol. 56; 2000; pp. 7903-7907.
Kanazaki et al.; "Highly Nuclease-Resistant Phosphodiester-Type Oligodeoxynucleotides Containing 4'a-C-Aminoalkylthymidines Form Thermally Stable Duplexes with DNA and RNA. A Candidate for Potent Antisense Molecules"; Journal of the American Chemical Society; vol. 122; 2000; pp. 2422-2432.
Uematsu et al., Synthesis and Properties of 4'-C-Guanidinomethyl-2'-O-methyl Modified RNA; Nucleic Acids Therapeutics Society of Japan; vol. 3; 2017; pp. 88.
Koizumi et al.; "Synthesis and Properties of 4'-C-Aminoalkyl-2'-O-methyl Modified RNA"; Nucleic Acids Therapeutics Society of Japan; vol. 3; 2017; pp. 87.
Maeda et al.; "Synthesis and properties of 4'-C-aminoethyl-2'-F modified nucleic acids"; Nucleic Acids Therapeutics Society of Japan; vol. 3; 2017; pp. 85.
Koizumi et al.; "Synthesis and Properties of 4'-C-Aminoalkyl-2'-O-methyl Modified Nucleic Acids"; The Chemical Society of Japan Spring Annual Meeting; vol. 97; Mar. 3, 2017; pp. 85.
Nawale et al.; "Incorporation of 4'-C-aminomethyl-2'-O-methylthymidine into DNA by thermophilic DNA polymerases"; Chemical Communications; vol. 48; 2012; pp. 9619-9621.
Jan. 30, 2018 International Search Report issued in International Patent Application No. PCT/JP2017/044995.
Aug. 15, 2018 International Preliminary Report on Patentability issued in International Patent Application No. PCT/JP2017/044995.
U.S. Appl. No. 16/760,781, filed Apr. 30, 2020 in the name of Ueno et al.

* cited by examiner

Melting temperatures (Tm) of RNA duplex sequences

| | Sequence | $T_m$ (°C) | $\Delta T_m$ (°C) | $\Delta T_m$ (°C)/mod |
|---|---|---|---|---|
| RNA1 | 5'- F UUC UUC UUC UUS -3'<br>3'-   AAG AAG AAG AA   -5' | 43.9 | | |
| RNA2 | 5'- F UuC UUC uUC UuS -3'<br>3'-   AAG AAG AAG AA   -5' | 37.5 | -6.4 | -2.1 |
| RNA3 | 5'- F UUC UUC UuC uuS -3'<br>3'-   AAG AAG AAG AA   -5' | 37.7 | -6.2 | -2.1 |
| RNA4 | 5'- F uuC uUC uUC uuS -3'<br>3'-   AAG AAG AAG AA   -5' | 34.1 | -9.8 | -1.6 |
| RNA5 | 5'- F uuC uUC uUC uuS -3'<br>3'-   AAG AAG AAG AA   -5' | 47.6 | 3.7 | 0.6 |

Change in UV absorption (260 nm) with temperature change

Melting temperatures (Tm) of RNA duplex sequences

| | Sequence | $T_m$ (°C) | $\Delta T_m$ (°C) | $\Delta T_m$ (°C)/mod |
|---|---|---|---|---|
| RNA6 | 5'- F UUC UUC UUC UUS -3'<br>3'-   aag aag aag aa     -5' | 45.5 | | |
| RNA7 | 5'- F UuC UUC uUC UuS -3'<br>3'-   aag aag aag aa     -5' | 38.7 | -6.8 | -2.3 |
| RNA8 | 5'- F UUC UUC UuC uuS -3'<br>3'-   aag aag aag aa     -5' | 39.6 | -5.9 | -2.0 |
| RNA9 | 5'- F uuC uUC uUC uuS -3'<br>3'-   aag aag aag aa     -5' | 34.2 | -11.3 | -1.9 |
| RNA10 | 5'- F uuC uUC uUC uuS -3'<br>3'-   aag aag aag aa     -5' | 49.8 | 4.3 | 0.7 |

Change in UV absorption (260 nm) with temperature change

Comparison of nuclease resistance according to differences in length of aminoalkyl side chains

FIG. 7

|  | ON1 | ON2 | ON3 | ON4 |
|---|---|---|---|---|
|  |  |  |  |  |
|  |  |  |  |  |

Comparison of cellular uptake ability according to position of aminoethyl uridine modification Comparison of cellular uptake ability according to differences in length of aminoalkyl side chains

```
                        SEQUENCE LISTING

<160> NUMBER OF SEQ ID NOS: 4

<210> SEQ ID NO 1
<211> LENGTH: 11
<212> TYPE: RNA
<213> ORGANISM: Artificial Sequence
<220> FEATURE:
<223> OTHER INFORMATION: Synthetic origonucleotide

<400> SEQUENCE: 1
uucuucuucu u                                                        11

<210> SEQ ID NO 2
<211> LENGTH: 11
<212> TYPE: DNA
<213> ORGANISM: Artificial Sequence
<220> FEATURE:
<223> OTHER INFORMATION: Synthetic origonucleotide

<400> SEQUENCE: 2
aagaagaaga a                                                        11

<210> SEQ ID NO 3
<211> LENGTH: 21
<212> TYPE: RNA
<213> ORGANISM: Artificial Sequence
<220> FEATURE:
<223> OTHER INFORMATION: Synthetic origonucleotide

<400> SEQUENCE: 3
ggccuuucac uacuccuacu u                                             21

<210> SEQ ID NO 4
<211> LENGTH: 21
<212> TYPE: RNA
<213> ORGANISM: Artificial Sequence
<220> FEATURE:
<223> OTHER INFORMATION: Synthetic origonucleotide

<400> SEQUENCE: 4
guaggaguag ugaaaggccu u                                             21
```

NUCLEOSIDE DERIVATIVE AND USE THEREOF

TECHNICAL FIELD

The present Description relates to a nucleoside derivative and a use thereof.

BACKGROUND ART

Many diseases including cancer are known to be caused by or associated with genetic mutations and abnormal gene expression. RNA drugs such as siRNA that suppress gene expression are useful against such diseases, and are considered to have excellent drug potential.

However, the problem with siRNA and the like is that they have difficulty passing through cell membranes, and are likely to be broken down by nucleases. Another problem is that although they are highly target-selective, they are difficult to transport selectively to target tissue. To resolve these issues, delivery carriers such as lipid nanoparticles (LNP) are being studied. Efforts have also been made to modify RNA by introducing aminomethyl groups into the ribose and the like (Non Patent Literature 1 to 4).

SUMMARY

Despite these efforts, however, there is demand for further improvement in the effectiveness of RNA drugs. Delivery carriers are also still unsatisfactory in some respects, and such RNA modifications have not achieved sufficient cell membrane permeability, ribonuclease resistance or target tissue delivery. Thus, the original drug potential of siRNA and the like has yet to be realized.

It is an object of this Description to provide a nucleoside that is more practical for applications such as RNA pharmaceuticals, along with a use therefor.

SOLUTION TO TECHNICAL PROBLEM

The inventors focused on ribose, which is the sugar part of a ribonucleotide. We discovered that both ribonuclease resistance and cell membrane permeability could be improved by providing a basic substituent such as an amino group at the 4' position of ribose, or by substituting a halogen atom for the 2' hydroxyl group. The present Description provides the following means based on these findings.

(1) A nucleoside derivative represented by formula (1) or (2) below, or a salt thereof.

[C1]

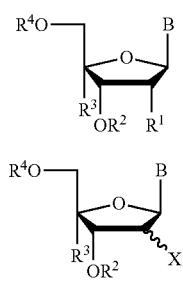

(In formula (1), $R^1$ represents a hydrogen atom, a hydroxyl group, a hydroxyl group in which a hydrogen atom is substituted by an alkyl group or alkenyl group, or a protected group, and in formula (2), X represent a halogen atom. In formula (1) and formula (2), $R^2$ and $R^4$ may be the same or different, and each represents a hydrogen atom, a hydroxyl protecting group, a phosphate group, a protected phosphate group, or —P(=O)$_n$$R^5$$R^6$ (in which n is 0 or 1, and $R^1$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group, but when n is 1, $R^5$ and $R^6$ are not both hydrogen atoms), $R^3$ represents NHR$^7$ (in which $R^7$ represents a hydrogen atom, an alkyl group, an alkenyl group or a protecting group for an amino group), an azide group, an amidino group or a guanidino group, each having a linking group (but when $R^7$ is hydrogen atom, the linking group is an alkylene group which has at least 2 carbon atoms), and B represents any of a purine-9-yl group, 2-oxo-pyrimidin-1-yl group, substituted purine-9-yl group or substituted 2-oxo-pyrimidin-1-yl group.)

(2) The nucleoside derivative or salt thereof according to (1), wherein in formulae (1) and (2) above, either $R^7$ represents a hydrogen atom or $R^3$ represents the guanidino group having a linking group.

(3) A nucleoside derivative or salt thereof according to (1) or (2), wherein the linking group of $R^3$ in formulae (1) and (2) above is a $C_{2-6}$ alkylene group.

(4) A nucleoside derivative or salt thereof according to any of (1) to (3), wherein in formulae (1) and (2) above, the linking group of $R^3$ is a $C_{2-6}$ alkylene group, and $R^7$ represents a hydrogen atom.

(5) A cell membrane permeability imparting agent for oligonucleotides, containing a nucleoside derivative according to any one of (1) to (4).

(6) A ribonuclease resistance imparting agent for oligonucleotides, containing a nucleoside derivative according to any one of (1) to (4).

(7) An oligonucleotide derivative or salt thereof, provided with at least 1 partial structure selected from the group consisting of formula (3) and formula (4) below.

[C2]

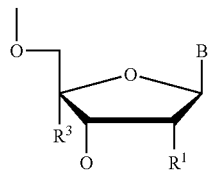

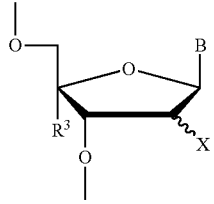

(In formula (3), $R^1$ represents a hydrogen atom, a halogen atom, a hydroxyl group, a hydroxyl group in which a hydrogen atom is substituted by an alkyl group or alkenyl group, or a protected hydroxyl group, and in formula (4), X represents a halogen atom. In formula (3) and formula (4), $R^3$ represents $NHR^7$ (in which $R^7$ represents a hydrogen atom, an alkyl group, an alkenyl group or a protecting group for an amino group), an azide group, an amidino group or a guanidino group, each having a linking group (but when $R^7$ is hydrogen atom, the linking group is an alkylene group which has at least 2 carbon atoms), and B represent any of a purine-9-yl group, 2-oxo-pyrimidin-1-yl group, substituted purine-9-yl group or substituted 2-oxo-pyrimidin-1-yl group.)

(8) The oligonucleotide derivative or salt thereof according to (7), provided with at least 2 of the partial structure.

(9) An oligonucleotide derivative or salt thereof according to (7) or (8), provided with at least 3 of the partial structure located at the 5' end, the center, and the 3' end of the oligonucleotide.

(10) An oligonucleotide derivative or salt thereof according to any of (7) to (9), provided with at least 6 of the partial structure.

(11) An oligonucleotide derivative or salt thereof according to any of (7) to (10), wherein the oligonucleotide is an oligoribonucleotide.

BRIEF DESCRIPTION OF DRAWINGS

FIG. 7 shows the results of an evaluation of cell membrane permeability due to aminoalkyl group modification;

DESCRIPTION OF EMBODIMENTS

Figure 1:
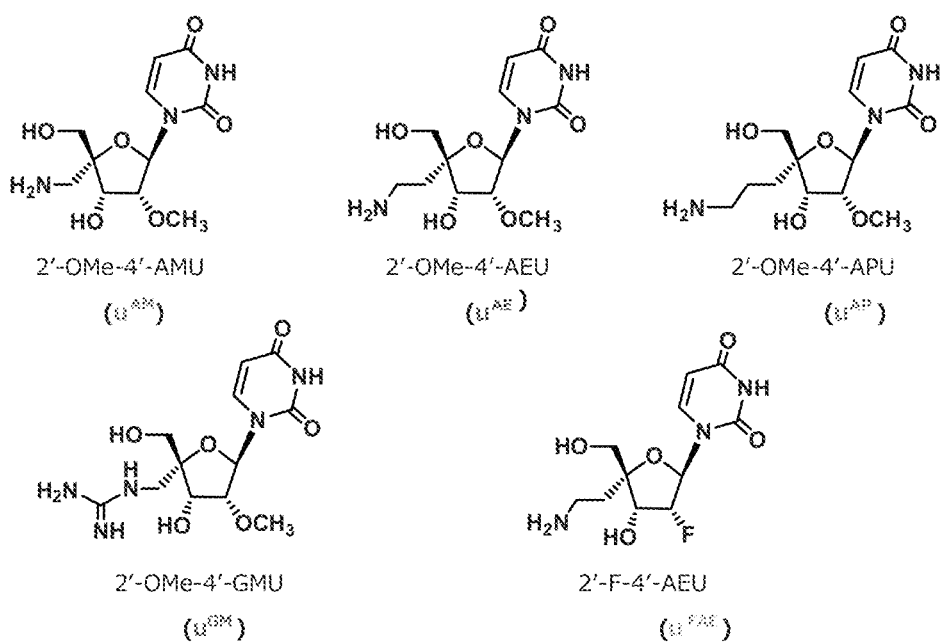
FIG. 1 shows the structures of monomers for oligonucleotide synthesis.

The disclosures of this Description relate to a nucleoside derivative or salt thereof that is practical for use in RNA pharmaceuticals, along with a use therefor. With the nucleoside derivative or salt thereof disclosed in this Description (hereunder sometimes called the nucleoside derivative), both ribonuclease resistance and cell membrane permeability are excellent. It is thus possible to provide an oligonucleotide suitable for administration without using carriers such as delivery LNPs that have been used in conventional RNA pharmaceuticals.

The nucleoside derivative is also useful as a reagent such as a detection probe using RNA. That is, an oligonucleotide suited to various RNA reagents can be provided.

The nucleoside derivative disclosed in this Description is based on the discovery that unexpectedly useful features were obtained when various aminoalkyl substituents were introduced into the 4' position of ribose (something that was difficult to achieve in the past), and the properties were scrutinized. Conventionally, ribonuclease resistance has been achieved by 2' or 3' substitution of ribose. With the nucleoside derivative disclosed in this Description, it is possible to achieve the properties of both unexpected ribonuclease resistance and cell membrane permeability, which are useful in RNA pharmaceuticals and the like.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and teachings to provide a further improved nucleoside derivative and use thereof.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the teaching, separately from the constitution of features described in the Examples and/or Claims. Moreover, all descriptions of numerical ranges and groups or sets are intended to include intermediate configurations for purposes of restricting the initial disclosures and the claimed matter specifying the teaching.

(Nucleoside Derivative)

The nucleoside derivative may be a nucleoside derivative represented by formula (1) or formula (2) below, or a salt thereof. This nucleoside derivative may be included in a partial structure of an oligonucleotide by methods well known to those skilled in the art.

[C3]

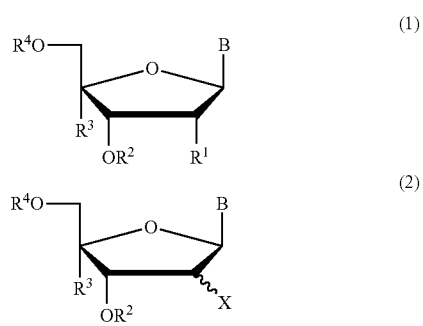

Because this nucleoside derivative is provided with a basic substituent at the 4' position of ribose and deoxyribose, it can have charge control properties that allow at least part of the negative charge derived from phosphoric acid groups and the like of the oligonucleotide to be neutralized in an oligonucleotide provided with a partial structure derived from the nucleoside derivative.

The cell membrane permeability of an oligonucleotide provided with such a partial structure can also be improved.

Furthermore, ribonuclease resistance can also be improved in an oligonucleotide provided with a partial structure derived from the nucleoside derivative.

In this Description, "lower" in a substituent of a compound represented by a formula or the like means that the number of carbon atoms constituting the substituent is not more than 10. For example, the number of carbon atoms is normally 1 to 6, or 1 to 5 for example, or 1 to 4, or preferably 1 to 3.

The nucleoside derivative or salt thereof disclosed in this Description is explained below, along with a use therefor.

(Nucleoside Derivative and Salt Thereof)

One embodiment of the nucleoside derivative or salt thereof is a nucleoside derivative or salt thereof represented by formula (1) below.

[C4]

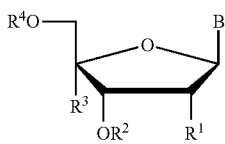

(1)

Another embodiment of the nucleoside derivative or salt thereof is a nucleoside derivative or salt thereof represented by formula (2) below.

[C5]

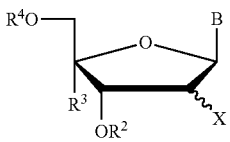

(2)

In formula (1), $R^1$ represents a hydrogen atom, a hydroxyl group, a hydroxyl group in which a hydrogen atom is substituted by an alkyl group or alkenyl group, or a protected hydroxyl group. When $R^1$ is a hydrogen atom, the nucleoside derivative is a deoxyribonucleoside derivative. When $R^1$ is a hydroxyl group, a hydroxyl group in which a hydrogen atom is substituted by an alkyl group or alkenyl group, or a protected hydroxyl group, the nucleoside derivative is a ribonucleoside derivative.

In formula (2), X represents a halogen atom. The halogen atom is not particularly limited, but may be a chlorine atom, iodine atom, fluorine atom, bromine atom or the like. When $R^1$ is a halogen atom, the nucleoside derivative is a deoxyribonucleoside. As is clear from formula (2), although the bonding direction of the halogen atom to the 2' carbon atom of ribose is not particularly limited, the halogen atom is preferably attached so as to correspond to the hydroxyl group of natural ribose.

(Alkyl Group)

In this Description, an alkyl group may be a saturated hydrocarbon group that is linear, branched, cyclic, or a combination of these. Normally a lower alkyl group is preferred, a $C_{1-6}$ lower alkyl group or $C_{1-5}$ lower alkyl groups is more preferred, and a $C_{1-4}$ or $C_{1-3}$ lower alkyl group is especially desirable. Desirable examples of linear $C_{1-4}$ alkyl groups include methyl, ethyl, n-propyl and n-butyl groups and the like, and of these, a methyl, ethyl or n-propyl group is preferred, a methyl or ethyl group is preferred for example, and a methyl group is preferred for example. Desirable examples of branched CIA alkyl groups include isopropyl, isobutyl, s-butyl and t-butyl groups and the like, and of these, an isopropyl group is especially desirable. Examples of cyclic $C_{1-4}$ alkyl groups include cyclopropyl, cyclobutyl and cyclopropylmethyl groups and the like.

(Alkenyl Group)

In this Description, an alkenyl group may be a saturated hydrocarbon group that is linear, branched, cyclic, or a combination of these. Normally a lower alkenyl group is preferred, and examples of lower alkenyl groups include ethenyl, 1-propenyl, 2-propenyl, 1-methyl-2-propenyl, 1-methyl-1-propenyl, 2-methyl-1-propenyl, 1-butenyl and 2-butenyl groups and the like.

(Hydroxyl Protecting Group or Protected Hydroxyl Group)

In this Description, a hydroxyl protecting groups may be one well known to those skilled in the art, and "Protective Groups in Organic Synthesis" (John Wiley and Sons, 2007) may be consulted for example. Typical examples of hydroxyl protecting groups include aliphatic acyl groups, aromatic acyl groups, lower alkoxymethyl groups, oxycarbonyl groups optionally having suitable substituents, tetrahydropyranyl groups optionally having suitable substituents, tetrathiopyranyl groups optionally having suitable substituents, methyl groups substituted with aryl groups that may be unsubstituted or have 1 to 3 substituents in total (in which a substituent in the substituted aryl group is a lower alkyl, a lower alkoxy, a halogen atom or a cyano group), or silyl groups or the like.

In this Description, an alkoxy group may be a saturated alkyl ether group that is linear, branched, cyclic, or a combination of these. A lower alkoxy group is preferred, and examples of lower alkoxy groups include $C_{1-6}$ lower alkoxy groups or $C_{1-5}$ lower alkoxy groups, of which a $C_{1-4}$ or $C_{1-3}$ alkoxy group is preferred, and a $C_{1-4}$ alkoxy group is especially preferred. Examples of CIA alkoxy groups include methoxy, ethoxy, n-propoxy and n-butoxy groups and the like. Other preferred examples include isopropoxy, isobutoxy, s-butoxy and t-butoxy groups and the like. Other preferred examples include cyclopropoxy, cyclobutoxy and cyclopropylmethoxy groups and the like.

In this Description, an alkylthio group may be a saturated alkylthio group that is linear, branched, cyclic, or a combination of these. A lower alkylthio group is preferred, a $C_{1-6}$ or $C_{1-5}$ lower alkylthio group is preferred as a lower alkylthio group for example, and a $C_{1-4}$ lower alkylthio group or $C_{1-3}$ alkylthio group is especially preferred. Preferred examples of $C_{1-4}$ saturated alkylthio groups include methylthio, ethylthio, n-propylthio and n-butylthio groups and the like. Other preferred examples include isopropylthio, isobutylthio, s-butylthio and t-butylthio groups and the like. Other preferred examples include cyclopropylthio and cyclobutylthio groups, and a cyclopropylmethylthio group is still more preferred.

Of these, especially preferred examples include aliphatic acyl groups, aromatic acyl groups and silyl groups. A methyl group substituted with an unsubstituted aryl group or an aryl group having 1 to 3 substituents in total (in which the substitutes of the substituted aryl are as described above) is also a preferred example.

Examples of the aliphatic acyl groups include alkylcarbonyl, carboxyalkylcarbonyl, halogeno lower alkyl carbonyl and lower alkoxy lower alkylcarbonyl groups.

The alkyl in the alkylcarbonyl group is as discussed above. That is, examples of alkylcarbonyl groups include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosyl groups. Of these, an acetyl, propionyl, butyryl, isobutyryl, pentanoyl or pivaloyl group is preferred, and an acetyl group is especially preferred. The alkyl in the carboxylated alkylcarbonyl group is as described above. The substitution position of carboxylation and the like may be selected appropriately. That is, examples of carboxylated alkylcarbonyl groups include succinoyl, glutaroyl and adipoyl groups.

The terms halogen, lower and alkyl in the halogeno lower alkylcarbonyl group are as explained above. The substitution position and the like of the halogen may also be selected appropriately. That is, examples of halogeno lower alkylcarbonyl groups include chloroacetyl, dichloroacetyl, trichloroacetyl and trifluoroacetyl groups.

The terms alkoxy, alkyl and lower in the lower alkoxy lower alkylcarbonyl group are as explained above. The substitution position and the like of the lower alkoxy can also be selected appropriately. That is, the lower alkoxy lower alkylcarbonyl group may be a methoxyacetyl group for example.

Examples of the aromatic acyl groups include arylcarbonyl, halogeno arylcarbonyl, lower alkylated arylcarbonyl, lower alkoxylated arylcarbonyl, carboxylated arylcarbonyl, nitrated arylcarbonyl and arylated arylcarbonyl groups.

Examples of the arylcarbonyl groups include benzoyl, α-naphthoyl and β-naphthoyl groups, and a benzoyl group is especially preferred. Examples of the halogeno arylcarbonyl groups include 2-bromobenzoyl and 4-chlorobenzoyl groups. Examples of the lower alkylated arylcarbonyl groups include 2,4,6-trimethylbenzoyl, 4-toluoyl, 3-toluoyl and 2-toluoyl groups. Examples of the lower alkoxylated arylcarbonyl group include 4-anisoyl, 3-anisoyl and 2-anisoyl groups.

Examples of the carboxylated arylcarbonyl groups include 2-carboxybenzoyl, 3-carboxybenzoyl and 4-carboxybenzoyl groups. Examples of the nitrated arylcarbonyl groups include 4-nitrobenzoyl, 3-nitrobenzoyl and 2-nitrobenzoyl groups. An example of an arylated arylcarbonyl group is 4-phenylbenzoyl.

Examples of the lower alkoxymethyl groups include methoxymethyl, 1,1-dimethyl-1-methoxymethyl, ethoxymethyl, propoxymethyl, isopropoxymethyl, butoxymethyl and t-butoxymethyl groups. A methoxymethyl group is especially preferred.

Examples of the oxycarbonyl groups optionally having suitable substituents include lower alkoxycarbonyl groups, lower alkoxycarbonyl groups substituted with halogens or silyl groups, and alkenyl oxycarbonyl groups.

Examples of the lower alkoxycarbonyl groups include methoxycarbonyl, ethoxycarbonyl and t-butoxycarbonyl isobutoxcarbonyl groups. Examples of the lower alkoxycarbonyl groups substituted with halogens or silyl groups include 2,2-trichloroethoxycarbonyl and 2-(trimethylsilyl) ethoxycarbonyl groups.

Examples of the alkenyl oxycarbonyl groups include vinyloxycarbonyl groups. Desirable example of the tetrahydropyranyl groups optionally having suitable substituents include tetrahydropyran-2-yl or 3-bromotetrahydropyran-2-yl, and tetrahydropyran-2-yl is especially desirable.

Examples of the tetrathiopyranyl groups optionally having suitable substituents include tetrahydrothiopyran-2-yl and 4-methoxytetrahydrothiopyran-4-yl, and tetrahydrothiopyran-2-yl is especially desirable. In a methyl group substituted with an aryl group optionally having 1 to 3 substituents in total, examples of the substituent of the substituted or unsubstituted aryl include lower alkyl and lower alkoxy groups, halogens, and cyano groups.

Examples of methyl groups substituted with aryl groups optionally having 1 to 3 substituents in total include benzyl, α-naphthylmethyl, β-naphthylmethyl, diphenylmethyl, triphenylmethyl and α-naphthyldiphenylmethyl groups, and a benzyl or triphenylmethyl group is preferred. Other examples include 9-anthrylmethyl-4-methylbenzyl, 2,4,6-trimethylbenzyl and 3,4,5-trimethylbenzyl groups, and a 2,4,6-trimethylbenzyl or 3,4,5-trimethylbenzyl group is preferred. Other examples include 4-methoxybenzyl, 4-methoxyphenyldiphenylmethyl and 4,4'-dimethoxytriphenylmethyl groups, and a 4-methoxybenzyl, 4-methoxyphenyldiphenylmethyl group, and 4,4'-dimethoxytriphenylmethyl groups are preferred. Other examples include 4-chlorobenzyl and 4-bromobenzyl groups. Another preferred example is a 4-cyanobenzyl group.

Examples of silyl groups in this Description include trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl and diphenylisopropylsilyl phenyldiisopropylsilyl groups and the like. Of these, a trimethylsilyl, t-butyldimethylsilyl, triisopropylsilyl or diphenylmethylsilyl group is preferred, and a trimethylsilyl, t-butyldimethylsilyl or diphenylmethylsilyl group is especially preferred.

A hydroxyl protecting group in this Description may mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). Substituents that are eliminated by hydrogenolysis or hydrolysis are especially desirable as hydroxyl protecting groups. Note that a protected hydroxyl group can be said to be a hydroxyl group in which such a protective group is substituted for a hydrogen atom.

[$R^2$ and $R^4$]

In formula (1) and formula (2), R and $R^4$ may be the same or different, and each represents a hydrogen atom, a hydroxyl protecting group, a phosphate group, a protected phosphate group, or —P(=O)$_n$($R^5$)$R^6$. The hydroxyl protecting group was already explained above.

(Protected Phosphate Group)

Protecting groups in protected phosphate groups are well known to those skilled in the art, and the above reference literature and explanations may be consulted.

Examples of protecting groups for phosphate groups include lower alkyl groups, lower alkyl groups substituted with cyano groups, ethyl groups substituted with silyl groups, lower alkyl groups substituted with halogens, lower alkenyl groups, lower alkenyl groups substituted with cyano groups, cycloalkyl groups, lower alkenyl groups substituted with cyano groups, aralkyl groups, aralkyl groups with nitro groups substituted on the aryl ring, aralkyl groups with halogens substituted on the aryl ring, aryl groups substituted with lower alkyl groups, aryl groups substituted with halogens, and aryl groups substituted with nitro groups.

Examples of the lower alkyl groups are as described above. Examples of the lower alkyl groups substituted with cyano groups include 2-cyanoethyl and 2-cyano-1,1-dimethylethyl groups, and a 2-cyanoethyl group is especially preferred. Examples of the ethyl groups substituted with silyl groups include 2-methyldiphenylsilylethyl, 2-trimethylsilylethyl and 2-triphenylsilylethyl groups.

Examples of the lower alkyl groups substituted with halogens include 2,2,2-trichloroethyl, 2,2,2-tribromoethyl, 2,2,2-trifluoroethyl and 2,2,2-trichloroethyl groups, and a 2,2,2-trichloroethyl group is especially preferred. Examples of the lower alkenyl groups include ethenyl, 1-propenyl, 2-propenyl, 1-methyl-2-propenyl, 1-methyl-1-propenyl, 2-methyl-1-propenyl, 1-butenyl and 2-butenyl groups and the like.

Examples of the lower alkenyl groups substituted with cyano groups include 2-cyanoethyl, 2-cyanopropyl and 2-cyanobutenyl groups. Examples of the aralkyl groups include benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl and 4-phenylbutyl groups, of which a benzyl group, diphenylmethyl group, triphenylmethyl group, 1-phenethyl group or 2-phenethyl group is more preferred, and a benzyl group is especially preferred.

Examples of the aralkyl groups with nitro groups substituted on the aryl ring include 2-(4-nitrophenyl) ethyl, 0-nitrobenzyl, 4-nitrobenzyl, 2,4-dinitrobenzyl and 4-chloro-2-nitrobenzyl groups and the like.

A protecting group for phosphoric acid in the present Description may mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). Substituents that are eliminated by hydrogenolysis or hydrolysis are especially desirable as protecting groups for phosphoric acid.

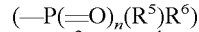
($-P(=O)_n(R^5)R^6$)

The $R^2$ and $R^4$ of the nucleoside analog of the present Description may be $-P(=O)_n(R^5)R^6$, in which n is 0 or 1, and $R^5$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group. However, when n is 1, $R^5$ and $R^6$ are not both hydrogen atoms. The protected hydroxyl group and lower alkoxy group are as explained above.

(Protected Mercapto Group)

Protected mercapto groups are well known to those skilled in the art. In addition to those given as examples of hydroxyl protecting groups above, examples of protected mercapto groups include alkylthio, arylthio, aliphatic acyl and aromatic acyl groups. An aliphatic acyl or aromatic acyl group is preferred, and an aromatic acyl group is especially preferred. A lower alkylthio group is preferred as an alkylthio group, and desirable examples include methylthio, ethylthio and t-butylthio groups. An example of an arylthio group is a benzylthio group. An example of an aromatic acyl group is a benzoyl group.

Preferred examples of the cyano lower alkoxy group include cyano-group substituted $C_{1-5}$ alkoxy groups (excluding the carbon atoms in the cyano group) that are linear, branched, cyclic, or a combination of these, and specific examples include cyanomethoxy, 2-cyanoethoxy, 3-cyanopropoxy, 4-cyanobutoxy, 3-cyano-2-methylpropoxy and 1-cyanomethyl-1,1-dimethylmethoxy groups and the like, with 2-cyanoethoxy group being especially preferred.

Substituted amino groups may be selected for $R^5$ and $R^6$. The substituent of such an amino group is any of a lower alkoxy group, lower alkylthio group, cyano lower alkoxy group or lower alkyl group. When both $R^5$ and $R^6$ are substituted amino groups, the substituted amino groups may be different from one another. The lower alkoxy, lower alkylthio, cyano lower alkoxy and lower alkyl groups are as explained above.

More specifically, preferred examples of $-P(=O)_n(R^5)R^6$ include phosphoramidite, H-phosphonate and phosphonyl groups, and a phosphoramidite group is especially desirable.

$-P(=O)_n(R^5)R^6$ becomes a phosphoramidite group when n is 0 and at least one of $R^5$ and $R^6$ is a substituted amino group, while the other may be anything. A phosphoramidite group in which one of $R^5$ and $R^6$ is a substituted amino group and the other is a lower alkoxy or cyano lower alkoxy group is especially desirable because it has good reaction efficiency in the condensation reaction. Preferred examples of the substituted amino group include diethylamino, diisopropylamino and dimethylamino groups, and a diisopropylamino group is especially desirable. A preferred example of a lower alkoxy group as another substituent of $R^5$ and $R^6$ is a methoxy group. A preferred example of a cyano lower alkoxy group is a 2-cyanoethyl group. Specific preferred examples of the phosphoramidite include $-P(OC_2H_4CN)N(CH(CH_3)_2)_2$ and $-P(OCH_3)N(CH(CH_3)_2)_2$.

$-P(=O)_n(R^5)R^6$ becomes an H-phosphonate group when n is 1 and at least one of $R^5$ and $R^6$ is a hydrogen atom while the other may be anything other than a hydrogen atom. Examples of the substituent other than a hydrogen atom include hydroxy, methyl, methoxy and thiol groups and the like, and a hydroxyl group is especially preferred.

$-P(=O)_n(R^5)R^6$ becomes a phosphonyl group when n is 1 and $R^5$ and $R^6$ are both lower alkoxy groups. The lower alkoxy groups of $R^5$ and $R^6$ may be the same or different. Preferred examples of these lower alkoxy groups include methoxy and ethoxy groups. A specific example of a phosphonyl group is $-P(=O)(OCH_3)_2$.

An especially preferred example of $R^2$ in the nucleoside derivative is $-P(=O)_n(R^5)R^6$. $-P(=O)_n(R^5)R^6$ preferably represents a phosphoramidite group, H-phosphonate group or phosphonyl group. $R^2$ may also preferably be a phosphate group or protected phosphate group. Other preferred examples of $R^2$ include a hydrogen atom and a hydroxyl protecting group.

Other specific examples of $R^2$ include a hydrogen atom, acetyl group, benzoyl group, benzyl group, p-methoxybenzyl group, trimethylsilyl group, tert-butyl diphenylsilyl group, $-P(OC_2H_4CN)N(CH(CH_3)_2)_2$, $-P(OCH_3)N(CH(CH_3)_2)_2$, or a phosphonyl group.

A hydrogen atom or hydroxyl protecting group is preferred as $R^4$ in the nucleoside derivative. A phosphate group, protected phosphate group or $-P(=O)_n(R^5)R^6$ is also desirable for example. As specific examples of $R^4$, a hydrogen atom, acetyl group, benzoyl group, benzyl group, p-methoxybenzyl group, dimethoxytrityl group, monomethoxytrityl group, tert-butyl diphenylsilyl group or trimethylsilyl group is preferred.

[$R^3$]

In formula (1) and formula (2), $R^3$ may represent $NHR^7$, an azide group, an amidino group or a guanidino group, each having a linking group. That is, the NHR⁷, azide group, amidino group and guanidino group are each linked to the 4' carbon atom via a linking group.

The linking group may represent a divalent hydrocarbon group having 1 or more carbon atoms for example. That is, examples of the divalent hydrocarbon group include $C_{1-8}$ alkylene and $C_{2-8}$ alkenylene groups.

An alkylene group used as a linking group may be linear or branched, but is preferably linear. A lower alkyl group is preferred, such as a $C_{1-6}$ lower alkyl group for example, or preferably a $C_{2-6}$ lower alkyl group, or a $C_{2-4}$ or $C_{2-3}$ lower alkyl group for example. Examples of linear $C_{1-4}$ alkyl groups include methylene, ethylene, propane-1,3-diyl, n-butane-1,1-diyl, n-pentyl-1,5-diyl and n-hexyl-1,6-diyl groups and the like. Other examples include butane-1,2-diyl group and the like. Especially desirable examples include ethylene, propane-1,3-diyl and n-butane-1,1-diyl groups.

An alkenylene group used as a linking group may be linear or branched, but is preferably linear. For example, a lower alkenylene group is preferred, and examples of lower alkenylene groups include ethene-1,2-diyl, propene-1,3-diyl and butene-1,4-diyl groups and the like.

In the nucleoside derivative represented by formula (1), a divalent hydrocarbon group such as an ethylene or other alkylene group with 2 or more carbon atoms is preferred from the standpoint of the nuclease resistance and cell membrane permeability of the oligonucleotide derivative. Moreover, a divalent hydrocarbon group such as an ethylene or other alkylene group with 1 or more carbon atoms is also desirable from the standpoint of nuclease resistance and cell membrane permeability in the nucleoside derivative represented by formula (2).

$R^7$ may be a hydrogen atom, alkyl group, alkenyl group, or amino group protecting group. In addition to the alkyl groups explained above, the alkyl group may preferably be a lower alkyl group. In addition to the alkenyl groups explained above, the alkenyl group may preferably be a lower alkenyl group. If $R^7$ is a hydrogen atom or one of these groups, the linking group is preferably an alkylene group with at least 2, or at least 3, or at least 4 carbon atoms for example, and not more than 6, or not more than 5, or not more than 4 carbon atoms for example. More preferably, the linking group has at least 2 carbon atoms, and is an alkylene group with 2 or more carbon atoms.

When $R^7$ is a hydrogen atom, $R^3$ is an $NH_2$ (amino group) having a linking group, which means that when the linking group is an alkylene group or alkenylene group, $R^3$ is an aminoalkyl or aminoalkenyl group. When $R^3$ is an aminoalkyl group or the like in formula (1) and formula (2), the nucleotide derivative and an oligonucleoside derivative provided with monomer units derived from the nucleoside derivative may demonstrate chargeability associated with the property of changing charge depending on the surrounding pH conditions. For example, the charge may be cationic under acidic conditions, but the positive charge may be reduced to zero charge in a neutral environment under physiological conditions. That is, due to this charge control ability, the charge of the nucleotide derivative can be made dynamic as necessary or the desired charge can be imparted by changing the pH environment. Consequently, with such a nucleoside derivative of the teaching the charge of the oligonucleoside can be controlled in a different way or with a greater degree of freedom than before. For this reason, a nucleoside derivative of the teaching in which $R^3$ is such an aminoalkyl group or the like is useful as a charge (positive charge) imparting agent or charge control agent for oligonucleotides and the like.

$R^3$ may be an azide group, an amidino group or in other words $CH_3(NH)C(NH)$-(amidine minus one hydrogen atom from the amino group), or a guanidino group or in other words $NH_2(NH)C(NH)$— (guanidine minus one hydrogen atom from the amino group), each having a linking group. Of these, it may be a guanidino group for example. When $R^3$ has these groups, the linking group may be an alkenylene group or alkylene group having at least 1 or at least 2 carbon atoms for example. When $R^3$ is an amidino group or guanidino group having a linking group, it is always cationic, unlike the case of the aminoalkyl group described above. Such a nucleoside derivative is useful when used in combination with a nucleoside derivative of the teaching in which $R^3$ is an aminoalkyl group or the like.

Protecting groups for amino groups are well known to those skilled in the art, and the reference literature described above may be consulted. In addition to those given as examples of hydroxyl protecting groups above, examples include benzyl, methylbenzyl, chlorobenzyl, dichlorobenzyl, fluorobenzyl, trifluoromethylbenzyl, nitrobenzyl, methoxyphenyl, methoxymethyl (MOM), N-methylaminobenzyl, N,N-dimethylaminobenzyl, phenacyl, acetyl, trifluoroacetyl, pivaloyl, benzoyl, phthalimido, allyloxycarbonyl, 2,2,2-trichloroethoxycarbonyl, benzyloxycarbonyl, t-butoxycarbonyl (Boc), 1-methyl-1-(4-biphenyl) ethoxycarbonyl (Bpoc), 9-fluorenylmethoxycarbonyl, benzyloxymethyl (BOM) and 2-(trimethylsilyl) ethoxymethyl (SEM) groups and the like. A benzyl, methoxyphenyl, acetyl, trifluoroacetyl (TFA), pivaloyl, benzoyl, t-butoxycarbonyl (Boc), 1-methyl-1-(4-biphenyl) ethoxycarbonyl (Bpoc), 9-fluorenylmethoxycarbonyl, benzyloxymethyl (BOM) or 2-(trimethylsilyl) ethoxymethyl (SEM) group is preferred, and a benzyl, methoxyphenyl, acetyl, benzoyl or benzyloxymethyl group is especially preferred.

A protecting group of an amino group in the present teaching may also mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). A substituent that is eliminated by hydrogenolysis or hydrolysis is especially desirable as an amino protecting group.

[B: Base]

The B: base in the nucleoside derivative may be a known natural base or an artificial base. For example, B may be selected from a purine-9-yl group, 2-oxo-pyrimidin-1-yl group, substituted purine-9-yl group and substituted 2-oxo-pyrimidin-1-yl group.

That is, examples of B include purine-9-yl and 2-oxo-pyrimidin-1-yl, as well as 2,6-dichloropurin-9-yl and 2-oxo-pyrimidine-1-yl. Other examples include 2-oxo-4-methoxy-pyrimidin-1-yl, 4-(1H-1,2,4-triazol-1-yl)-pyrimidin-1-yl, and 2,6-dimethoxypurin-9-yl.

Other examples include 2-oxo-4-amino-pyrimidin-1-yl in which the amino group is protected, 2-amino-6-bromopurin-9-yl in which the amino group is protected, 2-amino-6-hydroxypurin-9-yl in which the amino group is protected, 2-amino-6-hydroxypurin-9-yl in which the amino group and/or hydroxyl group are protected, 2-amino-6-chloropurin-9-yl in which the amino group is protected, 6-aminopurin-9-yl in which the amino group is protected, and 4-amino-5-methyl-2-oxo-pyrimidin-1-yl in which the amino group is protected. The respective protecting groups of the hydroxyl and amino groups are as explained above.

Other examples include 6-aminopurin-9-yl (adenine), 2-amino-6-hydroxypurin-9-yl (guanidine), 2-oxo-4-aminopyrimidin-1-yl (cytosine), 2-oxo-4-hydroxypyrimidin-1-yl (uracil) and 2-oxo-4-hydroxy-5-methylpyrimidin-1-yl (thymine).

Still other examples include 4-amino-5-methyl-2-oxo-pyrimidin-1-yl (methylcytosine), 2,6-diaminopurin-9-yl, 6-amino-2-fluoropurin-9-yl, 6-mercaptopyurin-9-yl, 4-amino-2-oxo-5-chloro-pyrimidin-1-yl, and 2-oxo-4-mercapto-pyrimidin-1-yl.

Yet other examples include 6-amino-2-methoxypurin-9-yl, 6-amino-2-chloropurin-9-yl, 2-amino-6-chloropurin-9-yl, and 2-amino-6-bromopurin-9-yl.

The respective substituents in the substituted purine-9-yl group or substituted 2-oxo-pyrimidin-1-yl group may be any of a hydroxyl group, a protected hydroxyl group, a lower alkoxy group, a mercapto group, a protected mercapto group, a lower alkylthio group, an amino group, a protected amino group, an amino group substituted with a lower alkyl group, a lower alkyl group, a lower alkoxymethyl group, a halogen atom, or a combination of these. These substituents have already been explained above.

Substituted purine-9-yl or substituted 2-oxo-pyrimidin-1-yl in which the substituents are those explained above is preferred as B in the nucleoside derivative, but it is also desirable to add a triazole group or lower alkoxymethyl group.

Desirable examples of substituted purine-9-yl include 6-aminopurin-9-yl, 2,6-diaminopurin-9-yl, 2-amino-6-chloropurin-9-yl, 2-amino-6-bromopurin-9-yl, 2-amino-6-hydroxypurin-9-yl, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl and 6-mercaptopurin-9-yl. If the substituent contains an amino group or hydroxyl group, desirable examples include substituents in which these amino groups and/or hydroxyl groups are protected.

Examples of substituted 2-oxo-pyrimidin-1-yl include 2-oxo-4-amino-pyrimidin-1-yl, 1H-(1,2,4-triazol-1-yl)-pyrimidin-1-yl, 4-1H-1,4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl, 2-oxo-4-hydroxy-5-methylpyrimidin-1-yl, 4-amino-5-methyl-2-oxo-pyrimidin-1-yl and the like.

Other desirable examples include 2-oxo-4-methoxy-pyrimidin-1-yl and 4-(1H-1,2,4-triazol-1-yl)-pyrimidin-1-yl.

Of these B bases, desirable examples include substituents in which the amino group or hydroxyl group has been protected if there is an amino group or hydroxyl group in the substituent.

The nucleoside derivative may also be a salt. The form of the salt is not particularly limited, but common examples include acid-addition salts, and the salt may also take the form of an intermolecular counter-ion. Depending on the types of substituents, it may also take the form of a base-addition salt. The salt is preferably a pharmacologically acceptable salt. Types of acids and bases used to form pharmacologically acceptable salts are well known to those skilled in the art, and reference may be made to those described in J. Pharm. Sci., 1-19 (1977) and the like. Examples of acid-addition salts include mineral acid salts and organic acid salts. When one or more substituents contain acidic parts, a base-addition salt may be preferred.

Examples of mineral acid salts include hydrochloride salts, hydrobromide salts, hydroiodide salts, nitrate salts, sulfate salts, hydrogen sulfate salts, phosphate salts, hydrogen phosphate salts and the like. Normally, a hydrochloride salt or phosphate salt is preferred. Examples of organic acid salts include acetate salts, trifluoroacetate salts, gluconate salts, lactate salts, salicylate salts, citrate salts, tartrate salts, ascorbate salts, succinate salts, maleate salts, fumarate salts, formate salts, benzoate salts, methansulfonate salts, ethanesulfonate salts, p-toluenesulfonate salts and the like. Normally, an acetate salt or the like is preferred. Examples of base-addition salts include alkali metal salts, alkali earth metal salts, organic amine salts, and amino acid addition salts.

Examples of the alkali metal salts include sodium salts, potassium salts and the like. Examples of the alkali earth metal salts include magnesium salts, calcium salts and the like. Examples of the organic amine salts include triethylamine salts, pyridine salts, procaine salts, picoline slats, dicyclohexylamine salts, diethanolamine salts, triethanolamine salts, tris(hydroxymethyl) aminomethane salts and the like. Examples of amino acid addition salts include arginine salts, lysine salts, ornithine salts, serine salts, glycine salts, aspartate salts, glutamate salts and the like.

The nucleoside derivative or salt thereof may be in the form of a hydrate or solvate, and these substances are also within the scope of the disclosures of this Description. The nucleoside derivative or salt thereof can be easily manufactured by a person skilled in the art by well-known methods, or following the synthesis examples below.

The nucleoside derivative can improve the nuclease resistance of a single- or double-stranded oligonucleotide when introduced as at least part of an oligonucleotide, and can also improve cell membrane permeability with respect to mammalian cells and the like. That is, the nucleoside derivative is itself useful as a nuclease resistance improving agent and/or cell membrane permeability imparting agent. The nucleoside derivative may also be provided with a basic substituent at the 4' position. It can thus function as a positive charge imparting agent or charge control agent by regulating the negative charge derived from phosphate groups in the oligonucleotide and the like.

(Oligonucleotide Derivative and Salt Thereof)

The oligonucleotide derivative disclosed in this Description (hereunder sometimes called "the oligonucleotide derivative") may contain at least 1 partial structure represented by formula (3) or (4). The partial structures represented by formula (3) and formula (4) can be obtained based on the nucleoside derivatives represented by formulae (1) and (2), respectively, or their salts.

[C6]

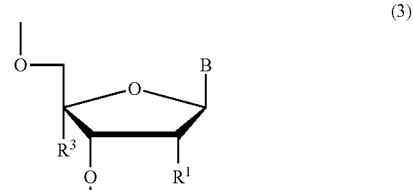

(3)

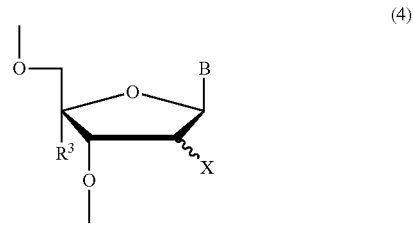

(4)

$R^1$, X, $R^3$ and B in the partial structures represented by formula (3) and formula (4) are defined as in formula (1) and formula (2).

2 or more of the partial structures represented by formula (3) and formula (4) may also be contained in the oligonucleotide derivative. In this case, these partial structure may be the same or different. Moreover, the total of the partial structures contained in the oligonucleotide derivative may consist only of partial structures represented by formula (3), or only of partial structures represented by formula (4). They may also comprise 1 or 2 or more partial structures represented by formula (3) and 1 or 2 or more partial structures represented by formula (4).

In terms of the arrangement of the partial structures represented by formulae (3) and (4), they may be disposed adjacent to one another or apart from one another. For example, the oligonucleotide derivative may be provided with at least 3 of such partial structures. In this case, the 3 partial structures may be more or less evenly distributed at the 5' end, center, and 3' end of the oligonucleotide derivative. The expression "partial structures are more or less evenly distributed at the above described locations of the oligonucleotide derivative" does not necessary mean that the same number of partial structures are provided at each location, but only that at least 1 partial structure is provided at each location. For example, if 1 to 3 partial structures are provided at each location, they may be considered evenly distributed. The oligonucleotide derivative may be provided with at least 6 partial structures.

Since the sugar chain part of the partial structure represented by formula (3) derives from ribose or deoxyribose, the oligonucleotide derivative may be either an oligoribonucleotide or an oligodeoxyribonucleotide. This oligonucleotide derivative may also be a chimera comprising both ribonucleotides and deoxyribonucleotides.

The oligonucleotide derivative is itself single-stranded, but it can also assume a hybrid form or in other words a double-stranded form with oligoribonucleotides, oligodeoxyribonucleotides and oligodeoxyribo/ribonucleotides (chimera strands).

The oligonucleotide derivative may also be provided with other partial structures corresponding to natural nucleotides, known nucleoside derivatives and/or known nucleotide derivatives and the like as partial structures other than those represented by formula (3) and formula (4). The partial structures stipulated in this Description and other partial structures may be linked together by phosphate diester linkage, phosphate monoester linkage or thiophosphate ester linkage or the like.

In terms of the number of units of the partial structures and other nucleoside derivatives, the oligonucleotide derivative of the teaching may have at least 2 such units, or preferably at least 8, or especially at least 15 such units. There is no particular maximum, but the number of units may be not more than 100, or not more than 80, or not more than 60, or not more than 50, or not more than 40, or not more than 30, or not more than 20 for example.

The oligonucleotide derivative may have one or more asymmetric centers in the partial structures represented by formula (3) and formula (4) as well as in other partial structures, and similarly when stereoisomers exist, the scope of the teaching encompasses any mixtures of stereoisomers or racemic mixtures. Tautomers may also be present.

The oligonucleotide derivative may also be a salt. The form of the salt is not particularly limited, and desirable examples include pharmacologically acceptable salts. Embodiments of the salt of the nucleoside derivative of the teaching described above may be applied to the salt. The oligonucleotide derivative or salt thereof may be in the form of a hydrate or solvate, and these are included within the scope of the teaching.

(Manufacturing Nucleoside Derivative and Oligonucleotide Derivative)

The nucleoside derivative and oligonucleotide derivative of the teaching can be easily synthesized by a person skilled in the art based on the specific synthesis examples below and on known synthesis technology for nucleosides and oligonucleotides as of the date of the application.

The nucleoside derivative and oligonucleotide derivative of the teaching can be manufactured by the following methods for example, but the methods for manufacturing the nucleoside derivative and oligonucleotide derivative of the teaching are not limited to the following methods.

The reaction times in the respective reactions are not particularly limited, and because the progress of the reaction can be easily tracked by the analysis methods described below, the reaction may be terminated at the point at which the yield of the target product the largest. Moreover, the respective reactions may also be performed in an inactive gas atmosphere such as a nitrogen flow or argon flow as necessary. When protection with a protecting group or subsequent deprotection is necessary in the respective reactions, these reactions may be accomplished appropriately by the methods described below.

In this Description, Bn represents a benzyl group, Ac an acetyl group, Bz a benzoyl group, PMB a p-methoxybenzyl group, Tr a triphenylmethyl group, THA a trifluoroacetyl group, TsO a tosyloxy group, MMTr a 4-methoxytriphenylmethyl group, DMTr a 4,4'-dimethoxytriphenylmethyl group, TMS a trimethylsilyl group, TBDMS a tert-butyl dimethylsilyl group, TBDPS a tert-butyl diphenylsilyl group, MOM a methoxymethyl group, BOM a benzyloxymethyl group, and SEM a 2-(trimethylsilyl) ethoxymethyl group.

For example, one example of the nucleoside derivative can be synthesized according to the following synthesis scheme. This scheme is an example of a scheme for synthesizing a thymine ribonucleoside derivative using glucose as a starting material, and then synthesizing a phosphoramidite agent for synthesizing the oligonucleotide derivative.

[C7]

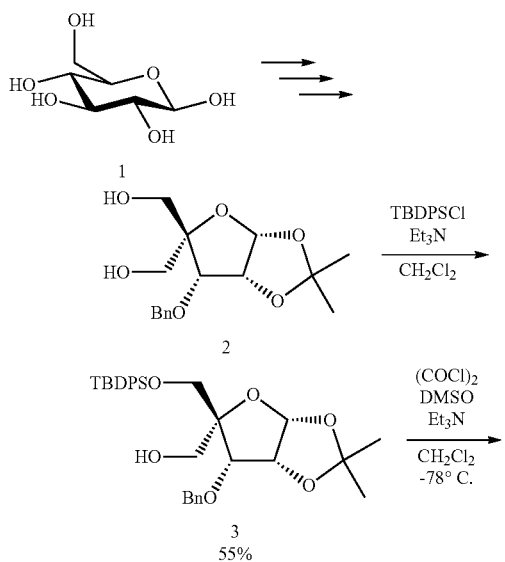

-continued
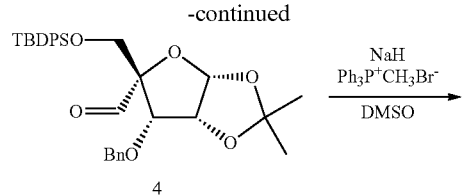
4
93%
NaH
Ph₃P⁺CH₃Br⁻
DMSO
→
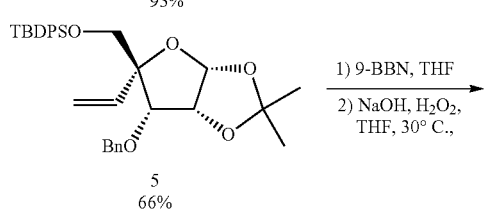
5
66%
1) 9-BBN, THF
2) NaOH, H₂O₂, THF, 30° C.,
→
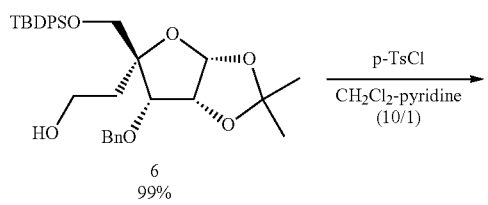
6
99%
p-TsCl
CH₂Cl₂-pyridine
(10/1)
→
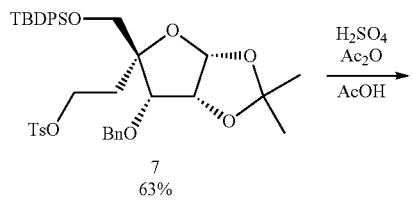
7
63%
H₂SO₄
Ac₂O
AcOH
→
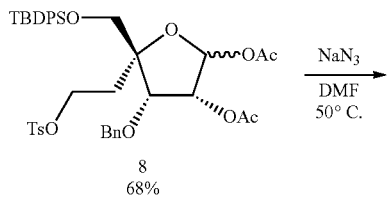
8
68%
NaN₃
DMF
50° C.
→
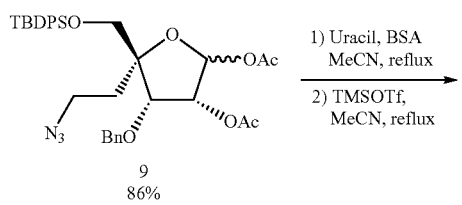
9
86%
1) Uracil, BSA
MeCN, reflux
2) TMSOTf, MeCN, reflux
→
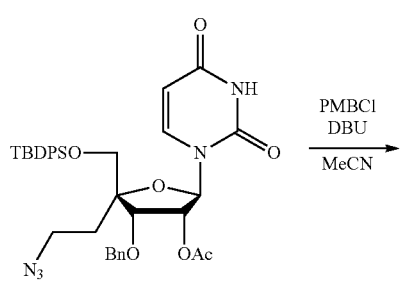
10
78%
PMBCl
DBU
MeCN
→
-continued
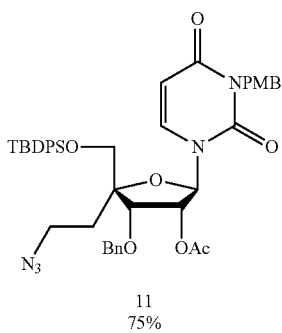
11
75%
[C8]
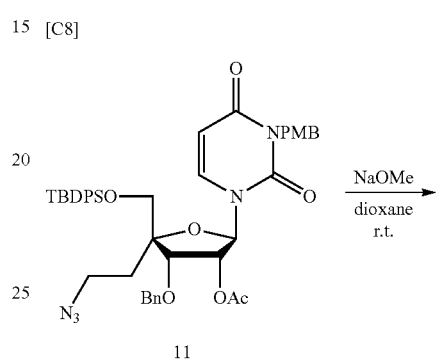
11
NaOMe
dioxane
r.t.
→
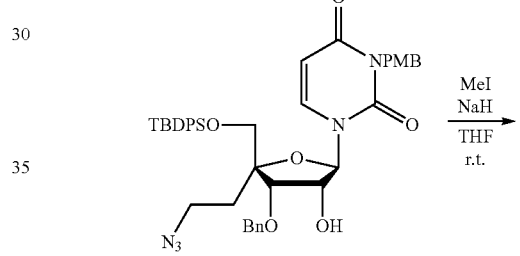
12
86%
MeI
NaH
THF
r.t.
→
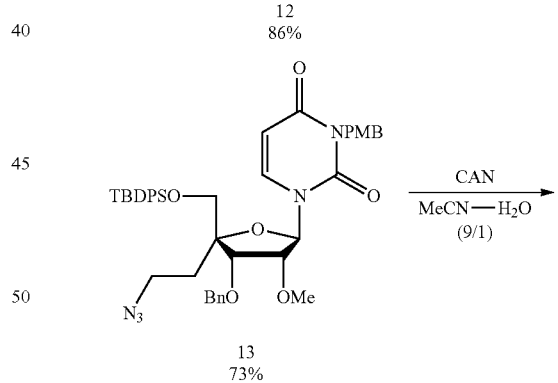
13
73%
CAN
MeCN—H₂O
(9/1)
→
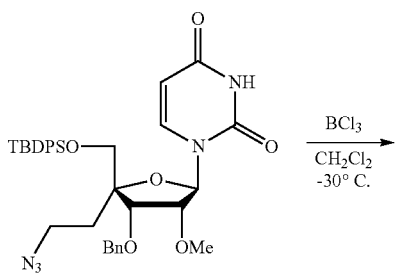
14
72%
BCl₃
CH₂Cl₂
-30° C.
→

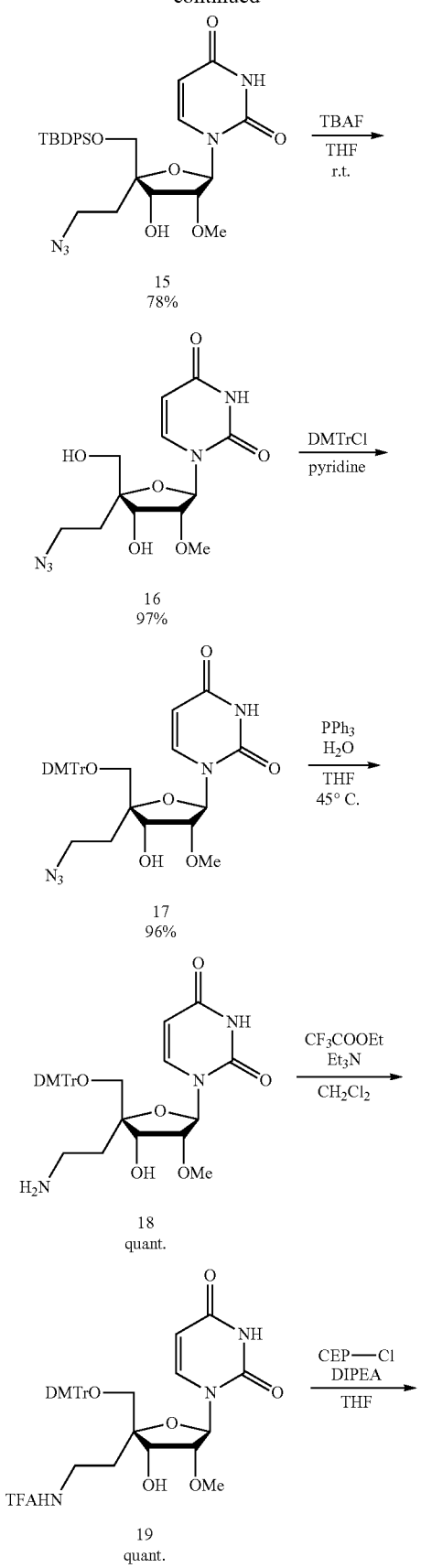

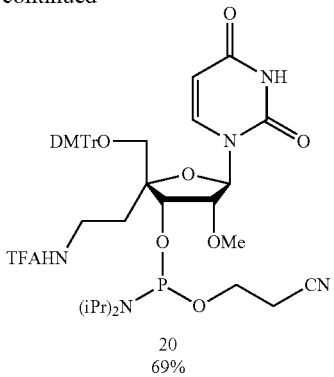

The compound 2 was obtained by ordinary methods from glucose 1. The compounds 3 to 20 can be obtained from the compound 2 based on the descriptions of Bioorganic & Medicinal Chemistry 11 (2003), 2211-2226, Bioorganic & Chemistry Letters (1999), 2667-2672, The Journal of Organic Chemistry 2013, 78, 9956-9962, HELVETICA CHIMICA ACTA Vol. 83 (2000), 128-151 and the like, as well as Bioorganic & Medicinal Chemistry 11 (2003), 2211-2226 and Bioorganic & Chemistry Letters (1999), 2667-2672.

Oligonucleotide derivatives of the teaching having the partial structures represented by formula (3) and formula (4) can be easily manufactured by using various kinds of the nucleoside derivatives represented by formula (1) or formula (2) as amidite agents and the like. That is, an oligonucleotide derivative of the teaching can be synthesized with a known DNA synthesizer from such a nucleoside derivative, the resulting oligonucleotide derivative can be purified with a column, and the purity of the product can be analyzed by reverse-phase HPLC or MALDI-TOF-MS to obtain the oligonucleotide derivative in purified form. Methods for making the oligonucleotide derivative into an acid-addition salt are well known to those skilled in the art.

Because the oligonucleotide derivative has a specific N-containing group at the ribose 4' position via a linking group, the net charge of RNA can be controlled, fat solubility (Van der Waals intermolecular force) can be increased, and the dsRNA melting temperature can be reduced while maintaining RNA functions such as RNA interference in vivo. It is thus possible to improve both ribonuclease resistance and cell membrane permeability. It is also possible to neutralize minus charge derived from phosphate groups and the like, and adjust the overall charge.

At least 2 of the partial structure may be provided in the oligonucleotide derivative. By providing a plurality of these partial structures, it is possible to effectively improve or regulate cell membrane permeability, ribonuclease resistance and the like. The oligonucleotide derivative of the teaching may also be provided with at least 3 of these partial structures.

The site provided with 1 or 2 or more of the partial structures in the oligonucleotide derivative is not particularly limited, and may be either the 5' end, or the 3' end, or both. The 5' end and 3' end are regions encompassing suitable numbers of nucleotides extending from each end of the polymer chain of the oligonucleotide, and are each regions consisting of not more than 30% for example of the total constituent units of the polymer chain. The percentage of the range from each end differs depending on the total length of the polymer chain, and may not more than 25%, or not more than 20%, or not more than 10%, or not more than 5% for example. More specifically, the 5' end and 3' end may be regions of constituent units derived from 1 to 30, or 1 to 25, or 1 to 20, or 1 to 15, or 1 to 10, or 1 to 8, or 1 to 6, or 1 to 5, or 1 to 4, or 1 to 3, or 1 to 2 nucleoside derivatives for example at each end of the oligonucleotide. The oligonucleotide derivative may be provided with 1 or 2 or more of the partial structures in either of these end regions, with 2 or more being preferred. Moreover, the oligonucleotide derivative may be provided with the partial structures at either the 5' end, or the 3' end (that is, as the first constituent unit from each end) or both.

In the oligonucleotide derivative, 1 or 2 or more of the partial structure may also be provided in the center, which is a part other than the 5' end and 3' end. Ribonuclease resistance and cell membrane permeability are even easier to improve or regulate when the oligonucleotide derivative is provided with the partial structure in the center. It also becomes easier to regulate the charge of the oligonucleotide as a whole.

The oligonucleotide derivative may also be provided with the partial structure in the center and in either or both of the 5' end and 3' end. Preferably, it may be provided with 1 or 2 or more of the partial structure at all of the 5' end, the 3' end, and the center. By thus distributing the partial structure more or less uniformly overall, it is possible to improve the ribonuclease resistance and cell membrane permeability as well as the charge control properties. Providing 2 or more of the partial structure in the center of the oligonucleotide derivative is useful for improving the characteristics.

A partial structure derived from the ribonucleoside derivative represented by formula (3) or a partial structure derived from the deoxyribonucleotide derivative represented by formula (4) may be used as the partial structure in the oligonucleotide derivative. The ribonucleoside derivative represented by formula (3) and the partial structure of formula (4) can be used as substitutes for ribonucleoside derivatives because they comprise an RNA base (uracil (U) or the like) as the B base.

From the standpoint of ribonuclease resistance and cell membrane permeability as well as charge control, $R^3$ in formula (3) and formula (4) preferably has $NHR^7$ with an alkylene having 1 or 2 or more carbon atoms as a linking group in the partial structure. In this case, $R^7$ may be a hydrogen atom or an acyl group having a roughly $C_{1-6}$ alkyl group. This alkylene group may be an ethylene group, propylene group, butylene group, pentylene group or hexylene group or the like. It may also be an ethylene group, propylene group, butylene group or the like for example. It may also be an ethylene group, propylene group or the like for example. By using an ethylene group or propylene group as a linking group, it is possible to obtain greater ribonuclease resistance, cell membrane permeability and charge control properties than are obtained using a methylene group.

The partial structure may also be an amidino group, azide group or guanidino group provided with a linking group. With such a functional group, it is possible to obtain high ribonuclease resistance and cell membrane permeability. In this case, the linking group may be an alkylene group with 1 or more carbon atoms.

In the partial structure, the linking group of $R^3$ in formula (3) and formula (4) is preferably a roughly $C_{1-6}$ alkyl group, and the lower limit of the carbon number is preferably at least 2, or more preferably at least 3. This structure is effective for obtaining ribonuclease resistance and cell membrane permeability.

The oligonucleotide derivative is preferably provided with at least 6 of the partial structure. Having 6 or more is effective for obtaining ribonuclease resistance and cell membrane permeability, as well as charge control properties.

The oligonucleotide derivative may be used for example as siRNA. That is, an oligonucleotide derivative forming a double strand can form complexes with in vivo components (RISC proteins) and sequence-specifically cleave mRNA, so that the information on the mRNA can no longer be translated into specific proteins by ribosomes. It is also thought that it can be incorporated as a constituent of miRNA or as a constituent of aptamer RNA, thus be used while simultaneously providing the features of improved ribonuclease resistance and cell membrane permeability. It can also link to other compounds to form conjugates. Moreover, the oligonucleotide derivative can also be used as a constituent of ribozymes. Furthermore, the oligonucleotide derivative is useful in reagents such as RNA chips.

Thus, because it has properties not found in natural nucleotides, the oligonucleotide derivative is expected to be more useful than natural nucleotides as a component of various RNA drugs that treat disease by inhibiting the action of genes, such as anti-tumor agents and anti-viral agents. That is, the oligonucleotide derivative is useful as such an RNA drug, and as a raw material or intermediate reagent. Moreover, the oligonucleoside derivative is useful as a raw material or intermediate of such RNA drugs.

The charge control properties, ribonuclease resistance, cell membrane permeability and charge control ability of the oligonucleotide derivative and the biological activity of various kinds of RNA containing the oligonucleotide derivative can be easily evaluated by a person skilled in the art with reference to Embodiments below and to well-known methods at the time of the application.

EMBODIMENTS

Embodiments are described below specific examples for explaining the disclosures of the Description in detail. The following Embodiments are for purposes of explaining the disclosures of the Description, and do not limit its scope.

First Embodiment (1) 2'OH-4' Aminomethyl Amidite Unit and Resin Body

A 2'OH-4' aminomethyl amidite unit and resin body were synthesized according to the following scheme.

[C9]

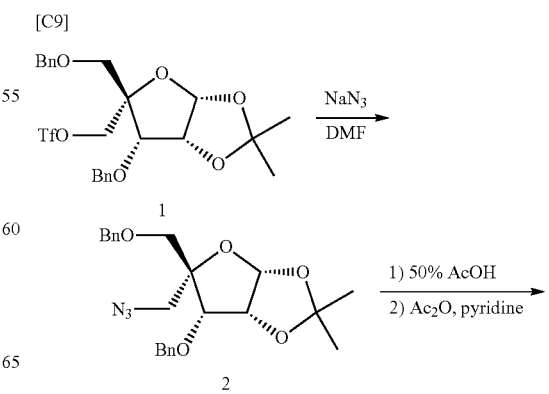

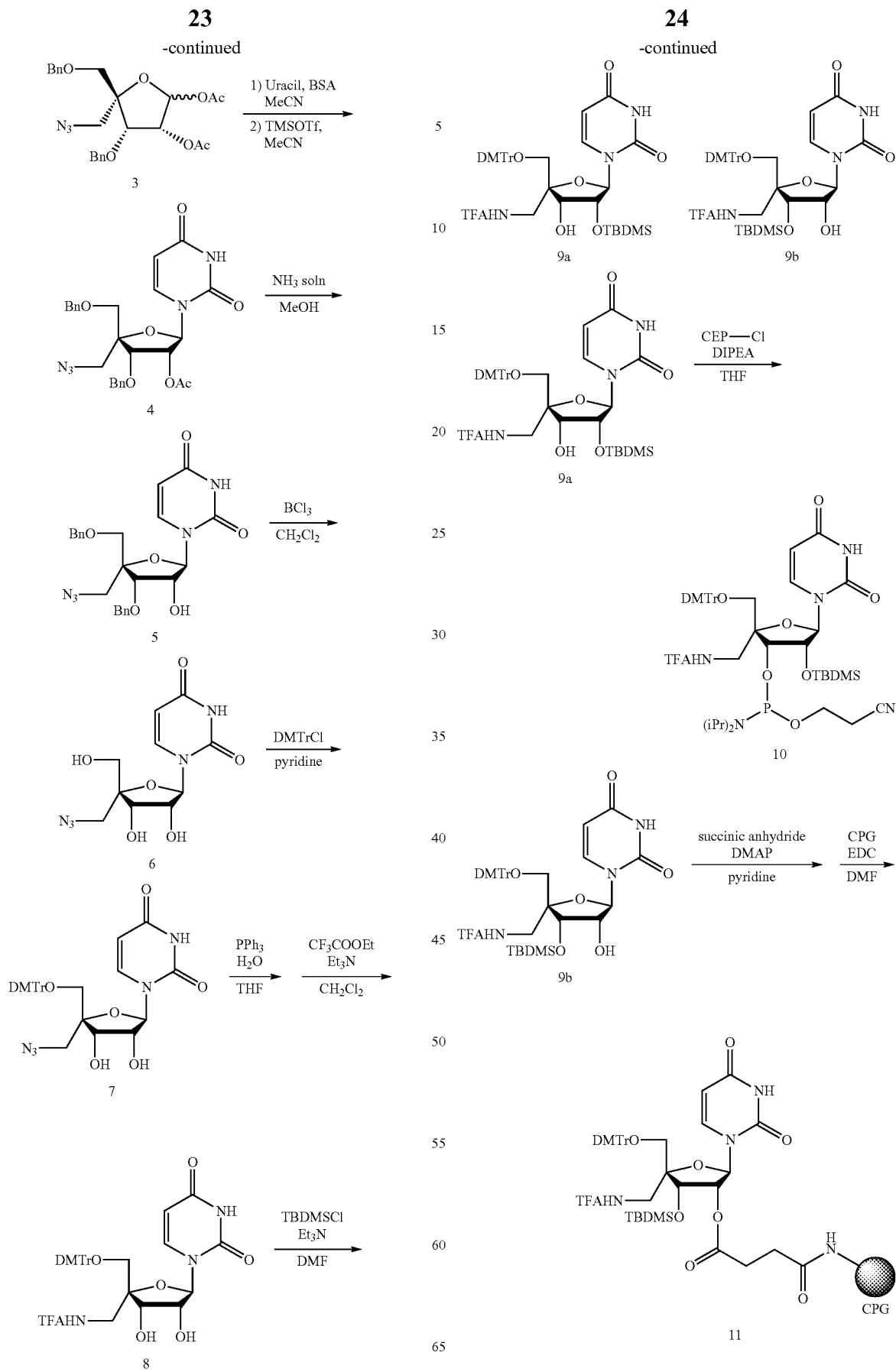

3,5-di-O-benzyl-4-C-{(trifluoromethanesulfonyl)oxy}methyl-1,2-O-(1-methylethylidene)-α-D-ribofuranose 1

A target substance 1 was synthesized by known methods (Bioorganic & Medicinal Chemistry 11 (2003), 2211-2226, Bioorganic & Chemistry Letters (1999), 2667-2672) using glucose as a starting material.

3,5-di-O-benzyl-4-C-azidomethyl-1,2-O-(1-methylethylidene)-α-D-ribofuranose 2

Sodium azide (NaN$_3$) (3.87 g, 59.6 mmol) was added in an argon atmosphere to dimethylformamide (DMF) solution (80 mL) of 3,5-di-O-benzyl-4-C-{(trifluoromethanesulfonyl)oxy}methyl-1,2-O-(1-methylethylidene)-α-D-ribofuranose (3.77 g, 7.09 mmol), and stirred overnight at 60° C. An ethyl acetate solution of the reaction mixture was washed with saturated saline. The organic layer was dried with anhydrous sodium sulfate, filtered, and concentrated under reduced pressure. The residue was purified by silica gel column chromatography [hexane-ethyl acetate, 4:1, v/v] to obtain a target substance 2 (2.16 g, 5.08 mmol, 72%).

$^1$H-NMR (400 MHz, CDCl$_3$) δ: 1.35 (s, 3H, CH$_3$), 1.65 (s, 3H, CH$_3$), 3.31 (d, J=13.3 Hz, 1H), 3.44 (d, J=10.6 Hz, 1H), 3.57 (d, J=10.1 Hz, 1H), 4.03 (d, J=13.3 Hz, 1H), 4.19 (d, J=5.0 Hz, 1H), 4.47 (d, J=11.9 Hz, 1H), 4.54 (d, J=12.4 Hz, 2H), 4.62 (t, J=3.7 Hz, 1H), 4.74 (d, J=12.4 Hz, 1H), 5.77 (d, J=4.1 Hz, 1H), 7.28-7.33 (m, 10H, Bn)

3,5-di-O-benzyl-4-C-azidomethyl-1,2-di-O-acetyl-α-D-ribofuranose 3

3,5-di-O-benzyl-4-C-azidomethyl-1,2-O-(1-methylethylidene)-α-D-ribofuranose (1.46 g, 3.44 mmol) was dissolved by addition of 50% acetic acid (29.6 mL), and stirred for 1 hour at 100° C. The reaction mixture was dried azeotropically with ethanol, pyridine (7.41 mL, 91.8 mmol) and acetic anhydride (Ac$_2$O) (4.93 mL, 52.2 mmol) were added, and the mixture was stirred overnight at room temperature in an argon atmosphere. The reaction mixture was cooled in an ice bath, poured into cold water, and extracted with ethyl acetate. The organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 4:1, v/v] to obtain a target substance 3 (1.46 g, 3.11 mmol, 90%).

$^1$H-NMR (400 MHz, CDCl$_3$) δ: 1.90 (s, 3H, CH$_3$), 2.13 (s, 3H, CH$_3$), 3.46 (ABq, J=19.2 Hz and 15.6 Hz, 2H), 3.60 (dd, J=11.9 Hz and 1.8 Hz, 2H), 4.35 (d, J=5.0 Hz, 1H), 4.48-4.52 (m, 4H), 4.60 (d, J=11.5 Hz, 1H), 5.34 (d, J=5.0 Hz, 1H), 6.16 (s, 1H), 7.28-7.36 (m, 10H, Bn)

3',5'-di-O-benzyl-4'-C-azidomethyl-2'-O-acetyluridine 4

Uracil (0.975 g, 8.70 mmol) and N,O-bis(trimethylsilyl)acetamide (BSA) (8.51 mL, 34.8 mmol) were added to an acetonitrile solution (20 mL) of 3,5-di-O-benzyl-4-C-azidomethyl-1,2-di-O-acetyl-α-D-ribofuranose (2.04 g, 4.35 mmol) in an argon atmosphere, and heat refluxed for 30 minutes at 95° C. This was cooled to 0° C., and trimethylsilyl trifluoromethanesulfonate (TMSOTf) (1.57 mL, 8.70 mmol) was carefully dripped in. This was then heat refluxed again for 15 minutes at 95° C. and then cooled in an ice bath, and saturated sodium bicarbonate solution was added. The reaction mixture was extracted with chloroform, and the organic layer was washed with saturated sodium bicarbonate solution. The organic layer was then dried with anhydrous sodium sulfate, filtered, and concentrated under reduced pressure. The residue was purified by silica gel column chromatography [hexane-ethyl acetate, 1:1, v/v] to obtain a target substance 4 (1.95 g, 3.75 mmol, 86%).

$^1$H-NMR (400 MHz, CDCl$_3$) δ:2.12 (s, 3H, CH$_3$), 3.36 (d, J=13.3 Hz, 1H), 3.48 (d, J=10.1 Hz, 1H), 3.66 (d, J=13.3 Hz, 1H), 3.77 (d, J=10.1 Hz, 1H), 4.38 (d, J=5.5 Hz, 1H), 4.42-4.48 (m, 3H), 4.63 (d, J=11.5 Hz, 1H), 5.32 (dd, J=7.8 Hz and 2.5 Hz, 1H), 5.40 (t, J=5.0 Hz, 1H), 6.18 (d, J=5.0 Hz, 1H), 7.27-7.41 (m, 10H, Bn), 7.64 (d, J=8.3 Hz, 1H), 8.25 (s, 1H)

3',5'-di-O-benzyl-4'-C-azidomethyluridine 5

Ammonia water (16 mL) and methanol (16 mL) were added to 3',5'-di-O-benzyl-4'-C-azidomethyl-2'-O-acetyluridine (1.95 g, 3.75 mmol), and stirred for 1.5 hours at room temperature. Ethanol was added to the reaction mixture, which was then concentrated under reduced pressure. The residue was purified by silica gel column chromatography [hexane-ethyl acetate, 1:2, v/v] to obtain a target substance 5 (1.73 g, 3.61 mmol, 96%).

$^1$H-NMR (400 MHz, CDCl$_3$) δ: 3.25 (d, J=8.3 Hz, 1H), 3.42 (d, J=12.8 Hz, 1H), 3.55 (d, J=10.1 Hz, 1H), 3.71 (m, 2H), 4.24 (d, J=6.0 Hz, 1H), 4.31-4.36 (m, 1H), 4.50 (2, 2H), 4.62 (d, J=11.5 Hz, 1H), 4.73 (d, J=11.4 Hz, 1H), 5.40 (dd, J=7.8 Hz and 2.3 Hz, 1H), 5.89 (d, J=4.6 Hz, 1H), 7.32-7.40 (m, 10H, Bn), 7.58 (d, J=8.4 Hz, 1H), 8.50 (s, 1H)

4'-C-azidomethyluridine 6

A dichloromethane solution (80 mL) of 3',5'-di-O-benzyl-4'-C-azidomethyluridine (3.16 g, 6.59 mmol) was cooled to −78° C. in an argon atmosphere, 1 M boron trichloride in dichloromethane (44.8 mL, 44.8 mmol) was added, and the mixture was stirred for 3 hours. The temperature was then raised to −30° C., and the mixture was stirred for 3 hours. Dichloromethane-methanol (1:1 v/v, 80 mL) was added to the reaction mixture, which was then concentrated under reduced pressure. The residue was purified by silica gel column chromatography [chloroform-methanol, 4:1, v/v] to obtain a target substance 6 (1.31 g, 4.38 mmol, 66%).

$^1$H-NMR (400 MHz, DMSO-d$_6$) δ: 3.15 (d, J=5.0 Hz, 1H), 3.58-3.55 (m, 3H), 4.02 (t, J=5.0 Hz, 1H), 4.22 (dd, J=6.4 Hz and 5.5 Hz, 1H), 5.30 (t, J=5.5 Hz, 1H), 5.38 (d, J=5.0 Hz, 1H), 5.45 (d, J=6.9 Hz, 1H), 5.68 (dd, J=8.2 Hz and 1.8 Hz, 1H), 5.88 (d, J=7.8 Hz, 1H), 7.82 (d, J=8.2 Hz, 1H), 11.4 (s, 1H); $^{13}$C-NMR (151 MHz, DMSO-d$_6$) δ 52.1, 62.9, 71.3, 73.0, 86.1, 87.0, 102.3, 140.8, 151.0, 163.0

5'-O-[bis(4-methoxyphenyl)phenylmethyl]-4'-C-azidomethyluridine 7

4,4'-dimethoxytrityl chloride (DMTrCl) (0.797 g, 2.35 mmol) was added in an argon atmosphere to a pyridine solution (5.4 mL) of 4'-C-azidomethyluridine (0.541 g, 1.81 mmol), and stirred overnight at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [chloroform-methanol, 12:1, v/v] to obtain a target substance 7 (0.464 g, 0.772 mmol, 43%) as a colorless amorphous substance.

$^1$H-NMR (400 MHz, CDCl$_3$) δ: 3.29 (d, J=3.6 Hz, 1H, 3'-OH), 3.33 (d, J=10.1 Hz, 1H, 4'(C)—CH$_2$), 3.39 (d, J=10.5 Hz, 1H, 4'(C)—CH$_2$), 3.58 (d, J=12.8 Hz, 1H, 5'-H), 3.67 (d, J=13.3 Hz, 1H, 5'-H), 3.77 (s, 6H, 2×OMe), 4.38 (q, J=5.5 Hz, 1H, 3'-H), 4.42 (q, J=5.5 Hz, 1H, 2'-H), 4.79 (d, J=5.0 Hz, 1H, 2'-OH), 5.41 (dd, J=8.3 Hz and 1.9 Hz, 1H, 5-H), 5.94 (d, J=5.5 Hz, 1H, 1'-H), 6.84 (d, J=9.2 Hz, 5H, DMTr), 7.23-7.37 (m, 8H, DMTr), 7.59 (d, J=8.2 Hz, 1H, 6-H), 9.65 (s, 1H, 3-NH)

5'-O-[bis(4-methoxyphenyl)phenylmethyl]-4'-C-trifluoroacetylaminomethyluridine 8

Triphenylphosphine (PPh$_3$) (0.491 g, 1.87 mmol) and water (0.540 mL, 30.0 mmol) were added to a tetrahydrofuran solution (15 mL) of 5'-O-[bis(4-methoxyphenyl)phenylmethyl]-4'-C-azidomethyluridine (0.450 g, 0.749 mmol), and stirred for 24 hours at 45° C. The tetrahydrofuran in the reaction mixture was distilled off under reduced pressure, and a dichloromethane solution (4.0 mL) was obtained. Ethyl trifluoroacetate (CF$_3$COOEt) (0.237 mL, 1.99 mmol) and triethylamine (Et$_3$N) (0.138 mL, 0.995 mmol) were added, and stirred for 24 hours at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [chloroform-methanol, 15:1, v/v] to obtain a target substance 8 (0.445 g, 0.663 mmol, 89%) as a colorless amorphous substance.

$^1$H-NMR (400 MHz, CDCl$_3$) δ: 1.26 (t, J=7.4 Hz, 2H, 4'(C)—CH$_2$), 3.27 (d, J=10.6 Hz, 1H, 5'-H), 3.32 (d, J=10.7 Hz, 1H, 5'-H), 3.76 (s, 6H, 2×OMe), 4.12 (q, J=7.3 Hz, 1H, 3'-OH), 4.35 (t, J=5.5 Hz, 1H, 3'-H), 4.51 (q, J=5.2 Hz, 1H, 2'-H), 5.07 (d, J=4.1 Hz, 1H, 2'-OH), 5.44 (dd, J=7.8 Hz and 1.8 Hz, 1H, 1'-H), 6.83 (d, J=8.7 Hz, 4H, DMTr), 7.11 (t, J=6.2 Hz, 1H, —NHCOCF$_3$), 7.22-7.34 (m, 9H, DMTr), 7.57 (d, J=8.2 Hz, 1H, 6-H), 9.74 (s, 1H, 3-NH)

5'-O-[bis(4-methoxyphenyl)phenylmethyl]-4'-C-trifluoroacetylaminomethyl-2'-O-[(1,1-dimethylethyl)dimethylsilyl]-uridine 9a 5'-O-[bis(4-methoxyphenyl)phenylmethyl]-4'-C-trifluoroacetylaminomethyl-3'-O-[(1,1-dimethylethyl)dimethylsilyl]-uridine 9b Triethylamine (Et$_3$N) (0.276 mL, 1.99 mmol) and tert-butyldimethylsilyl chloride (TBDMSCl) (0.200 g, 1.33 mmol) were added in an argon atmosphere to a dimethylformamide solution (4.4 mL) of 5'-O-[bis(4-methoxyphenyl)phenylmethyl]-4'-C-trifluoroacetylaminomethyluridine (0.445 g, 0.663 mmol), and stirred overnight at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 9a (0.221 g, 0.281 mmol, 42%) and a target substance 9b (0.142 g, 0.181 mmol, 27%).

Compound 9a $^1$H-NMR (600 MHz, CDCl$_3$) δ: 0.0520 (s, 3H, Si—SH$_3$), 0.108 (s, 3H, Si—CH$_3$), 0.911 (s, 9H, tert-butyl), 3.10 (s, 1H, 3'-OH), 3.33 (s, 2H, 5'-OH), 3.56 (m, 1H, 4'(C)—CH$_2$), 3.63 (m, 1H, 4'(C)—CH$_2$), 3.80 (s, 6H, 2×OMe), 4.23 (d, J=5.5 Hz, 1H, 3'-H), 4.60 (t, J=6.2 Hz, 1H, 2'-H), 5.42 (d, J=8.2 Hz, 1H, 5-H), 6.04 (d, J=6.9 Hz, 1H, 1'-H), 6.84 (d, J=8.9 Hz, 5H, DMTr), 7.20-7.22 (m, 4H, DMTr), 7.29-7.32 (m, 4H, DMTr), 7.65 (d, J=8.2 Hz, 1H, 6-H), 8.57 (s, 1H, 3-NH)

Compound 9b $^1$H-NMR (600 MHz, CDCl$_3$) δ: −0.0305 (s, 3H, Si—CH$_3$), 0.0749 (s, 3H, Si—CH$_3$), 0.866 (s, 9H, tert-butyl), 3.07 (d, J=4.1 Hz, 1H, 2'-OH), 3.22 (d, J=10.3 Hz, 1H, 5'-H), 3.37 (d, J=10.3 Hz, 1H, 5'-H), 3.59 (q, J=4.7 Hz, 1H, 4'(C)—CH$_2$), 3.64 (q, J=7.0 Hz, 1H, 4'(C)—CH$_2$), 3.79 (s, 6H, 2×OMe), 4.26 (m, 1H, 2'-H), 4.49 (d, J=6.2 Hz, 1H, 3'-H), 5.44 (d, J=7.6 Hz, 1H, 5-H), 5.76 (d, J=3.5 Hz, 1H, 1'-H), 6.83 (dd, J=8.9 Hz and 2.7 Hz, 4H, DMTr), 7.11 (s, 1H, —NHCOCF$_3$), 7.23-7.34 (m, 9H, DMTr), 7.57 (d, J=8.3 Hz, 1H, 6-H), 8.55 (s, 1H, 3-NH)

5'-O-[bis(4-methoxyphenyl)phenylmethyl]-4'-C-trifluoroaminomethyl-2'-O-[(1,1-dimethylethyl)dimethylsilyl]-3'-[2-cyanoethyl-N,N-bis(1-methylethyl)-phosphoramidite]-uridine 10

Diisopropyl ethylamine (DIPEA) (0.245 mL, 0.141 mmol) and 2-cyanoethyl N,N-diisopropylchlorophosphoramidite (CEP-Cl) (0.125 mL, 0.562 mmol) were added in an argon atmosphere to a tetrahydrofuran solution (2.2 mL) of 5'-O-[bis(4-methoxyphenyl)phenylmethyl]-4'-C-trifluoroacetylaminomethyl-2'-O-[(1,1-dimethylethyl)dimethylsilyl]-uridine (0.221 g, 0.281 mmol), and stirred for 1 hour at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 2:3, v/v] to obtain a target substance 10 (0.215 g, 0.218 mmol, 78%).

$^{31}$P-NMR (400 MHz, CDCl$_3$) δ: 151.67, 152.10

5'-O-[bis(4-methoxyphenyl)phenylmethyl]-4'-C-trifluoroacetylaminomethyl-3'-O-[(1,1-dimethylethyl)dimethylsilyl]-uridine carrying CPG carrier 11

N,N-dimethyl-4-aminopyridine (DMAP) (44.2 mg, 0.362 mmol) and succinic anhydride (72.5 mg, 0.724 mmol) were added in an argon atmosphere to a pyridine solution (2.0 mL) of 5'-O-[bis(4-methoxyphenyl)phenylmethyl]-4'-C-trifluoroacetylaminomethyl-3'-O-[(1,1-dimethylethyl)dimethylsilyl]-uridine (0.142 g, 0.181 mmol), and stirred for 24 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. Dimethylformamide (1.9 mL) was added to dissolve the residue, and controlled pore glass (CPG) (0.359 g) and 1-(3-dimethylaminopropyl)-3-ethylcarbodiimide hydrochloride (EDC) (36.6 mg, 0.191 mmol) were added and shaken for 3 days. The CPG was filtered and washed with pyridine, after which DMAP (0.183 g), pyridine (13.5 mL) and acetic anhydride (1.5 mL) were added in an argon atmosphere and left standing for 24 hours. The CPG was filtered, and dried after washing with pyridine, ethanol and acetonitrile to obtain a target substance 11 (activity: 35.6 μmol/g).

(2) 2'OH-4' Aminoethyl Resin Body

A 2'OH-4' aminoethyl amidite unit and resin body were synthesized according to the following scheme.

[10]

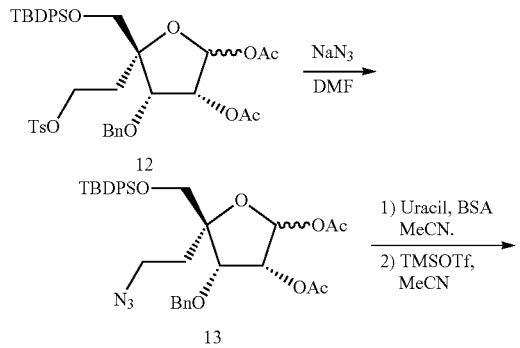

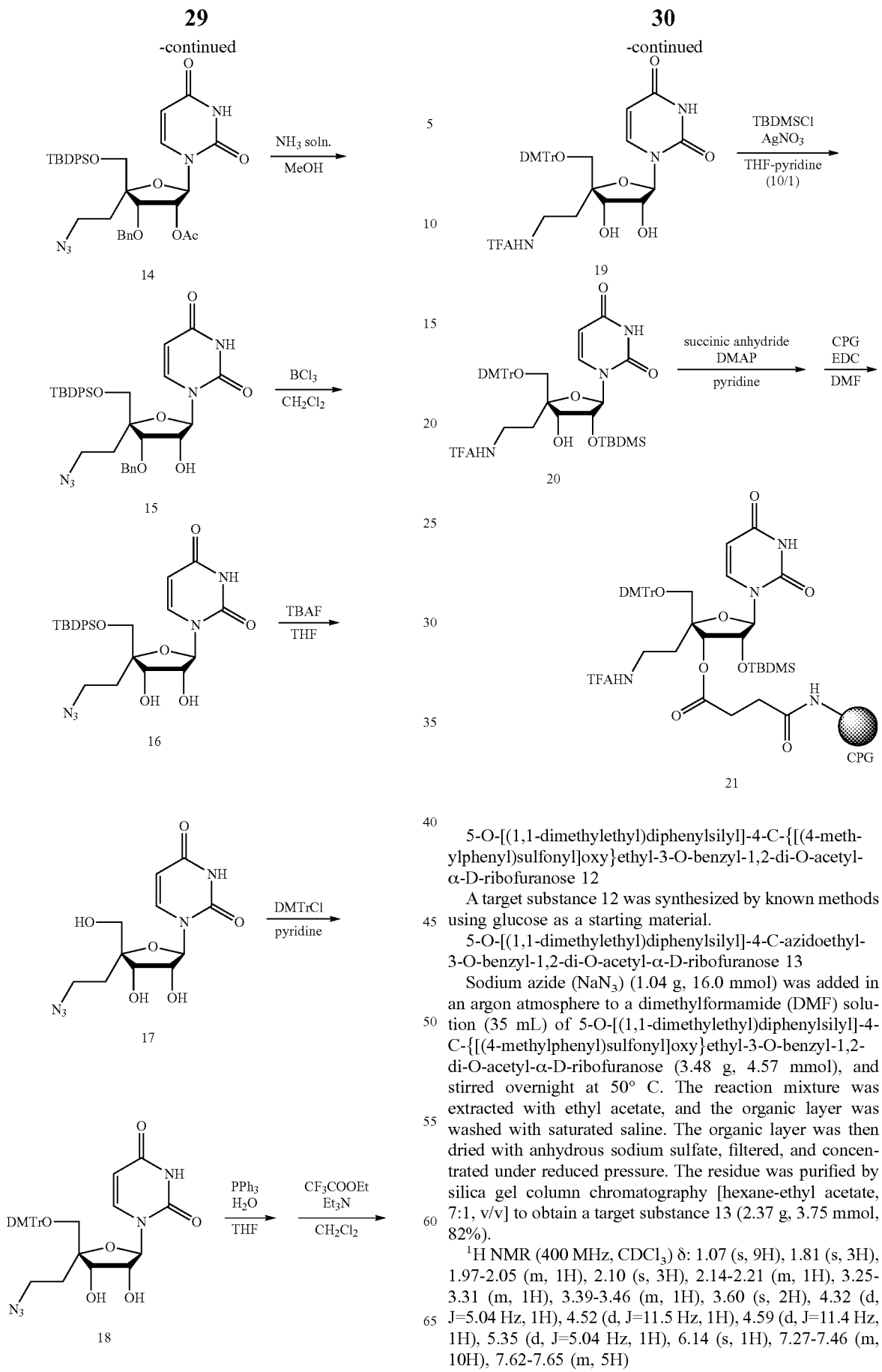

5-O-[(1,1-dimethylethyl)diphenylsilyl]-4-C-{[(4-methylphenyl)sulfonyl]oxy}ethyl-3-O-benzyl-1,2-di-O-acetyl-α-D-ribofuranose 12

A target substance 12 was synthesized by known methods using glucose as a starting material.

5-O-[(1,1-dimethylethyl)diphenylsilyl]-4-C-azidoethyl-3-O-benzyl-1,2-di-O-acetyl-α-D-ribofuranose 13

Sodium azide (NaN$_3$) (1.04 g, 16.0 mmol) was added in an argon atmosphere to a dimethylformamide (DMF) solution (35 mL) of 5-O-[(1,1-dimethylethyl)diphenylsilyl]-4-C-{[(4-methylphenyl)sulfonyl]oxy}ethyl-3-O-benzyl-1,2-di-O-acetyl-α-D-ribofuranose (3.48 g, 4.57 mmol), and stirred overnight at 50° C. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 7:1, v/v] to obtain a target substance 13 (2.37 g, 3.75 mmol, 82%).

$^1$H NMR (400 MHz, CDCl$_3$) δ: 1.07 (s, 9H), 1.81 (s, 3H), 1.97-2.05 (m, 1H), 2.10 (s, 3H), 2.14-2.21 (m, 1H), 3.25-3.31 (m, 1H), 3.39-3.46 (m, 1H), 3.60 (s, 2H), 4.32 (d, J=5.04 Hz, 1H), 4.52 (d, J=11.5 Hz, 1H), 4.59 (d, J=11.4 Hz, 1H), 5.35 (d, J=5.04 Hz, 1H), 6.14 (s, 1H), 7.27-7.46 (m, 10H), 7.62-7.65 (m, 5H)

¹³C NMR (151 MHz, CDCl₃) δ: 19.46, 20.96, 21.11, 27.04, 31.56, 46.78, 67.99, 73.65, 74.58, 79.32, 87.08, 97.82, 127.64, 127.94, 128.02, 128.07, 128.61, 130.03, 130.13, 132.71, 133.08, 135.65, 135.75, 137.49, 169.28, 169.78

5'-O-[(1,1-dimethylethyl)diphenylsilyl]-4'-C-azidoethyl-3'-O-benzyl-2'-O-acetyluridine 14

Uracil (3.95 g, 35.2 mmol) and N,O-bis(trimethylsilyl)acetamide (BSA) (34.4 mL, 141 mmol) were added in an argon atmosphere to an acetonitrile solution (100 mL) of 5-O-[(1,1-dimethylethyl)diphenylsilyl]-4-C-azidoethyl-3-O-benzyl-1,2-di-O-acetyl-α-D-ribofuranose (11.1 g, 17.6 mmol), and heat refluxed for 1 hour at 95° C. This was cooled to 0° C., and trimethylsilyl trifluoromethanesulfonate (TMSOTf) (6.36 mL, 35.2 mmol) was carefully dripped in. This was then stirred again for 3 hours at 50° C. and cooled in an ice bath, and saturated sodium bicarbonate solution was added. The reaction mixture was extracted with chloroform, and the organic layer was washed with saturated sodium bicarbonate solution. The organic layer was then dried with anhydrous sodium sulfate, filtered, and concentrated under reduced pressure. The residue was purified by silica gel column chromatography [hexane-ethyl acetate, 2:1, v/v] to obtain a target substance 14 (10.2 g, 14.9 mmol, 85%).

¹H NMR (400 MHz, CDCl₃) δ: 1.10 (s, 9H), 1.65-1.73 (m, 1H), 2.05-2.14 (m, 4H), 3.23-3.30 (m, 1H), 3.35-3.41 (m, 1H), 3.56 (d, J=11.5 Hz, 1H), 3.86 (d, J=11.5 Hz, 1H), 4.39-4.42 (m, 2H), 4.61 (d, J=11.0 Hz, 1H), 5.32-5.39 (m, 2H), 6.13 (d, J=5.04 Hz, 1H), 7.33-7.49 (m, 10H), 7.57-7.64 (m, 6H), 8.02 (s, 1H)

¹³C NMR (151 MHz, CDCl₃) δ: 19.46, 20.89, 27.18, 31.09, 46.53, 66.54, 74.59, 74.92, 86.85, 87.42, 103.07, 128.03, 128.21, 128.25, 128.39, 128.74, 130.38, 130.48, 131.91, 132.60, 135.47, 135.77, 137.10, 139.87, 150.18, 162.78, 170.09

5'-O-[(1,1-dimethylethyl)diphenylsilyl]-4'-C-azidoethyl-3'-O-benzyluridine 15

Ammonia water (83 mL) and methanol (83 mL) were added to 5'-O-[(1,1-dimethylethyl)diphenylsilyl]-4'-C-azidoethyl-3'-O-benzyl-2'-O-acetyluridine (10.2 g, 14.9 mmol), and stirred overnight at room temperature. Ethanol was added to the reaction mixture, which was then concentrated under reduced pressure. The residue was purified by silica gel column chromatography [hexane-ethyl acetate, 1:1, v/v] to obtain a target substance 15 (9.39 g, 14.6 mmol, 98%).

¹H NMR (500 MHz, CDCl₃) δ: 1.09 (s, 9H), 1.67-1.73 (m, 1H), 2.15-2.21 (m, 1H), 3.20-3.26 (m, 1H), 3.33-3.38 (m, 1H), 3.47-3.55 (m, 2H), 3.80 (d, J=10.9 Hz, 1H), 4.19 (d, J=6.30 Hz, 1H), 4.30 (q, J=5.75 Hz, 1H), 4.59 (d, J=11.5 Hz, 1H), 4.72 (d, J=11.5 Hz, 1H), 5.39 (d, J=8.60 Hz, 1H), 5.90 (d, J=5.70 Hz, 1H), 7.32-7.42 (m, 9H), 7.45-7.48 (m, 2H), 7.57-7.62 (m, 5H), 9.20 (s, 1H)

¹³C NMR (151 MHz, CDCl₃) δ: 19.44, 27.19, 31.19, 46.55, 66.86, 74.70, 74.99, 78.77, 87.23, 89.37, 102.84, 128.21, 128.25, 128.35, 128.61, 128.89, 130.39, 130.49, 131.99, 132.57, 135.49, 135.74, 136.89, 139.98, 150.83, 163.00

5'-O-[(1,1-dimethylethyl)diphenylsilyl]-4'-C-azidoethyluridine 16

A dichloromethane solution (95 mL) of 5'-O-[(1,1-dimethylethyl)diphenylsilyl]-4'-C-azidoethyl-3'-O-benzyluridine (2.42 g, 3.77 mmol) was cooled to −78° C. in an argon atmosphere, 1 M boron trichloride in dichloromethane (25.6 mL, 25.6 mmol) was added, and the mixture was stirred for 3 hours. The temperature was then raised to −30° C., and the mixture was stirred for 3 hours. Dichloromethane-methanol (1:1 v/v, 50 mL) was added to the reaction mixture, which was then concentrated under reduced pressure. The residue was purified by silica gel column chromatography [hexane-ethyl acetate, 1:1, v/v] to obtain a target substance 16 (1.91 g, 3.47 mmol, 92%).

¹H NMR (500 MHz, CDCl₃) δ: 1.08 (s, 9H), 1.85-1.91 (m, 1H), 2.10-2.16 (m, 1H), 3.32-3.38 (m, 2H), 3.45 (d, J=4.0 Hz, 1H), 3.66 (d, J=10.9 Hz, 1H), 3.78 (d, J=11.5 Hz, 1H), 4.33 (t, J=5.70 Hz, 1H), 4.43-4.44 (m, 1H), 5.11 (d, J=5.15 Hz, 1H), 5.38 (d, J=8.05 Hz, 1H), 5.95 (d, J=5.15 Hz, 1H), 7.40-7.48 (m, 6H), 7.61-7.64 (m, 4H), 7.74 (d, J=8.60 Hz, 1H), 10.2 (s, 1H)

¹³C NMR (151 MHz, CDCl₃) δ: 19.42, 27.15, 31.12, 46.86, 67.25, 72.31, 75.93, 88.67, 89.52, 102.61, 128.22, 128.24, 130.36, 130.47, 131.95, 132.55, 135.53, 135.75, 140.26, 151.79, 163.59

4'-C-azidoethyluridine 17

A 1 M tetrabutyl ammonium fluoride tetrahydrofuran solution (TBAF) (2.0 mL, 2.0 mmol) was added in an argon atmosphere to a tetrahydrofuran solution (8.0 mL) of 5'-O-[(1,1-dimethylethyl)diphenylsilyl]-4'-C-azidoethyluridine (0.746 g, 1.35 mmol), and stirred for 24 hours at room temperature. The solvent was then distilled off under reduced pressure, and the residue was purified by silica gel column chromatography [chloroform-methanol, 5:1, v/v] to obtain a target substance 17 (0.409 g, 1.31 mmol, 97%).

¹H NMR (400 MHz, CDCl₃) δ: 0.958-1.02 (m, 1H), 1.10-1.18 (m, 1H), 2.54-2.64 (m, 4H), 3.15 (t, J=5.04 Hz, 1H), 3.41 (q, J=7.32 Hz, 1H), 4.40-4.43 (m, 2H), 4.50 (d, J=6.40 Hz, 1H), 4.85 (d, J=8.24 Hz, 1H), 5.01 (d, J=7.36 Hz, 1H), 7.02 (d, J=8.24 Hz, 1H), 10.5 (s, 1H)

5'-O-[bis(4-methoxyphenyl)phenylmethyl]-4'-C-azidoethyluridine 18

4,4'-dimethoxytrityl chloride (DMTrCl) (1.93 g, 5.69 mmol) was added in an argon atmosphere to a pyridine solution (12 mL) of 4'-C-azidoethyluridine (1.19 g, 3.79 mmol), and stirred for 7 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:4, v/v] to obtain a target substance 18 (1.19 g, 1.94 mmol, 51%).

5'-O-[bis(4-methoxyphenyl)phenylmethyl]-4'-C-trifluoroacetylaminoethyluridine 19

Triphenylphosphine (PPh₃) (1.30 g, 4.95 mmol) and water (1.43 mL, 79.32 mmol) were added to a tetrahydrofuran solution (40 mL) of 5'-O-[bis(4-methoxyphenyl)phenylmethyl]-4'-C-azidoethyluridine (1.19 g, 1.94 mmol), and stirred for 7 hours at 45° C. The tetrahydrofuran in the reaction mixture was distilled off under reduced pressure, and a dichloromethane (11 mL) solution was obtained. Ethyl trifluoroacetate (CF₃COOEt) (0.691 mL, 5.79 mmol) and triethylamine (Et₃N) (0.401 mL, 2.90 mmol) were added, and stirred for 24 hours at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 1:2, v/v] to obtain a target substance 19 (1.05 g, 1.53 mmol, 79%).

¹H NMR (400 MHz, CDCl₃) δ: 2.00-2.05 (m, 1H), 2.11-2.17 (m, 1H), 3.25-3.35 (m, 4H), 3.78 (s, 6H), 3.96 (s, 1H), 4.35 (s, 1H), 4.52 (s, 1H), 5.17 (s, 1H), 5.41 (d, J=7.80

Hz, 1H), 5.96 (d, J=5.96 Hz, 1H), 6.86 (d, J=8.72 Hz, 5H), 7.28-7.41 (m, 8H), 7.46 (m, 1H), 7.65 (d, J=8.24 Hz, 1H), 10.2 (s, 1H)

5'-O-[bis(4-methoxyphenyl)phenylmethyl]-4'-C-trifluoroacetylaminoethyl-2'-O-[(1,1-dimethylethyl)dimethylsilyl]-uridine 20

Pyridine (0.753 mL, 9.33 mmol), silver nitrate (AgNO₃) (0.442 g, 2.60 mmol) and tert-butyldimethylsilyl chloride (TBDMSCl) (0.461 g, 3.06 mmol) were added in an argon atmosphere to a tetrahydrofuran solution (10 mL) of 5'-O-[bis(4-methoxyphenyl)phenylmethyl]-4'-C-trifluoroacetylaminoethyluridine (1.04 g, 1.53 mmol), and stirred for 3 hours at room temperature. The reaction mixture was diluted with chloroform, filtered through Celite, and concentrated under reduced pressure. The residue was purified by silica gel column chromatography [hexane-ethyl acetate, 3:2, v/v] to obtain a target substance 20 (1.13 g, 1.41 mmol, 92%).

¹H NMR (600 MHz, CDCl₃) δ: 0.0554 (s, 3H), 0.113 (s, 3H), 0.912 (s, 9H), 2.00 (t, J=6.18 Hz, 2H), 3.16 (d, J=1.38 Hz, 1H), 3.25-3.34 (m, 4H), 3.80 (s, 6H), 4.20 (d, J=4.14 Hz, 1H), 4.62 (t, J=5.52 Hz, 11H), 5.35 (dd, J=8.22 Hz and 2.04 Hz, 11H), 6.02 (d, J=6.84 Hz, 1H), 6.85 (d, J=8.22 Hz, 4H), 7.19-7.24 (m, 5H), 7.30-7.33 (m, 4H), 7.67 (d, J=8.28 Hz, 1H), 8.06 (s, 1H)

5'-O-[bis(4-methoxyphenyl)phenylmethyl]-4'-C-trifluoroacetylaminoethyl-2'-O-[(1,1-dimethylethyl)dimethylsilyl]-uridine carrying CPG carrier 21

N,N-dimethyl-4-aminopyridine (DMAP) (64.0 mg, 0.524 mmol) and succinic anhydride (0.105 g, 1.05 mmol) were added in an argon atmosphere to a pyridine solution (3.0 mL) of 5'-O-[bis(4-methoxyphenyl)phenylmethyl]-4'-C-trifluoroacetylaminoethyluridine (0.209 g, 0.262 mmol), and stirred for 24 hours at room temperature. The reaction mixture was extracted with ethyl acetate, and the organic layer was washed with saturated sodium bicarbonate solution. The organic layer was then dried with anhydrous sodium sulfate, filtered, and concentrated under reduced pressure. The residue was purified by silica gel column chromatography [chloroform-methanol, 15:1, v/v]. Dimethylformamide (2.77 mL) was added to dissolve the purified product, and controlled pore glass (CPG) (0.444 g) and 1-(3-dimethylaminopropyl)-3-ethylcarbodiimide hydrochloride (EDC) (51.8 mg, 0.270 mmol) were added and shaken for 4 days. The CPG was filtered and washed with pyridine, after which DMAP (0.183 g), pyridine (13.5 mL) and acetic anhydride (1.5 mL) were added in an argon atmosphere and left standing for 32 hours. The CPG was filtered, and dried after washing with pyridine, ethanol and acetonitrile to obtain a target substance 21 (activity: 30.7 μmol/g).

(3) 2'OMe-4' Aminoethyl Amidite Unit

A 2'OMe-4' aminoethyl amidite unit was synthesized according to the following scheme.

[C11]

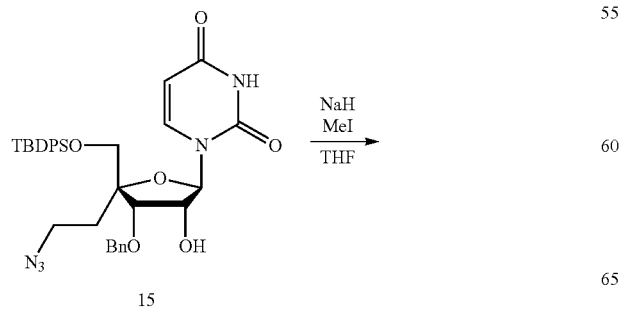

15

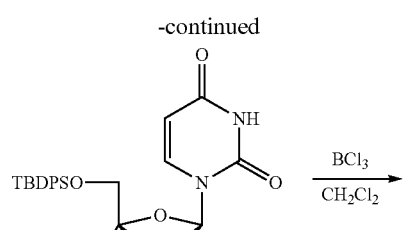

22

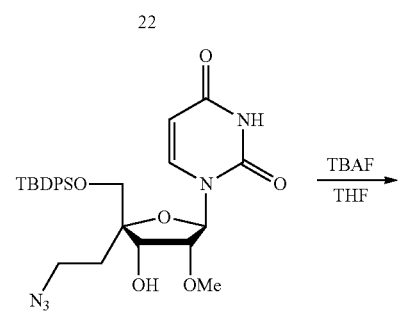

23

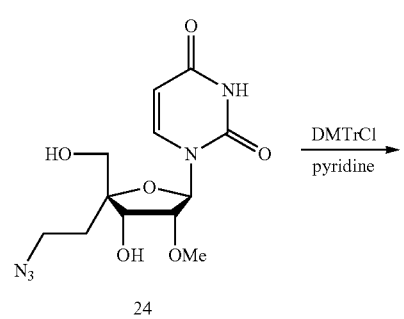

24

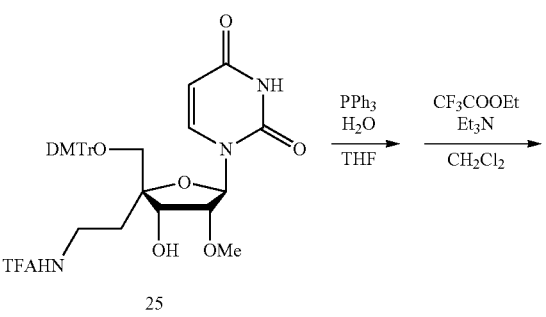

25

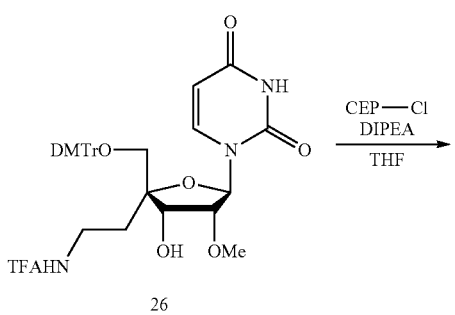

26

-continued

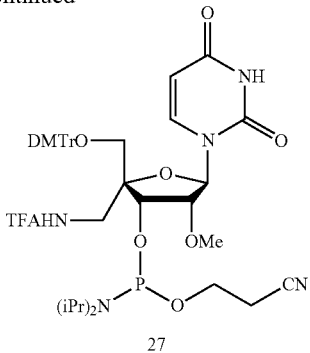

27 methyluridine 22

60% sodium hydride (NaH) (1.14 g, 28.4 mmol) was added in an ice bath in an argon atmosphere to a tetrahydrofuran solution (60 mL) of 5'-O-[(1,1-dimethylethyl)diphenylsilyl]-4'-C-azidoethyl-3'-O-benzyluridine (6.06 g, 9.46 mmol), and stirred for 10 minutes at 0° C. Iodomethane (CH$_3$I) (2.94 mL, 47.3 mmol) was then dripped carefully into this, and the mixture was shaken for 8 hours at 0° C. under shaded conditions. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 2:1, v/v] to obtain a target substance 22 (4.18 g, 6.37 mmol, 67%).

$^1$H NMR (400 MHz, CDCl$_3$) δ: 1.09 (s, 9H), 1.71-1.77 (m, 1H), 2.29-2.35 (m, 1H), 3.25-3.31 (m, 1H), 3.34-3.39 (m, 1H), 3.52 (s, 3H), 3.68 (d, J=11.5 Hz, 1H), 3.75 (dd, J=5.70 Hz and 2.30 Hz, 1H), 3.98 (d, J=11.5 Hz, 1H), 4.35 (d, J=6.30 Hz, 1H), 4.51 (d, J=11.5 Hz, 1H), 4.71 (d, J=11.5 Hz, 1H), 5.09 (dd, J=8.00 Hz and 1.70 Hz, 1H), 6.08 (d, J=2.30 Hz, 1H), 7.34-7.40 (m, 9H), 7.44-7.47 (m, 2H), 7.51 (d, J=7.45 Hz, 2H), 7.61 (d, J=6.85 Hz, 2H), 7.79 (d, J=8.05 Hz, 1H), 8.96 (s, 1H)

$^{13}$C NMR (126 MHz, CDCl$_3$) δ: 19.57, 27.25, 31.05, 46.61, 59.45, 65.45, 73.16, 75.78, 83.96, 87.30, 88.33, 102.58, 128.00, 128.15, 128.26, 128.33, 128.73, 130.33, 130.42, 131.97, 132.89, 135.36, 135.58, 137.33, 139.98, 149.99, 163.08

5'-O-[(1,1-dimethylethyl)diphenylsilyl]-4'-C-azidoethyl-2'-O-methyluridine 23

A dichloromethane solution (42 mL) of 5'-O-[(1,1-dimethylethyl)diphenylsilyl]-4'-C-azidoethyl-3'-O-benzyl-2'-O-methyluridine (1.06 g, 1.62 mmol) was cooled to −78° C. in an argon atmosphere, 1 M boron trichloride in dichloromethane (11 mL, 11 mmol) was added, and the mixture was stirred for 3 hours. The temperature was then raised to −20° C., and the mixture was stirred for 5 hours. Dichloromethane-methanol (1:1 v/v, 24 mL) was added to the reaction mixture, which was then concentrated under reduced pressure. The residue was purified by silica gel column chromatography [hexane-ethyl acetate methanol, 1:1, v/v] to obtain a target substance 23 (0.713 g, 1.26 mmol, 78%).

$^1$H NMR (600 MHz, CDCl$_3$) δ: 1.11 (s, 9H), 1.73-1.78 (m, 1H), 2.05-2.10 (m, 1H), 2.89 (d, J=5.52 Hz, 1H), 3.28-3.33 (m, 1H), 3.36-3.40 (m, 1H), 3.53 (s, 3H), 3.71 (d, J=11.7 Hz, 1H), 3.89-3.93 (m, 2H), 4.49 (t, J=6.18 Hz, 1H), 5.33 (d, J=6.18 Hz, 1H), 6.08 (s, J=4.14 Hz, 1H), 7.40-7.43 (m, 4H), 7.46-7.48 (m, 2H), 7.61 (d, J=7.56 Hz, 2H), 7.65 (d, J=7.56 Hz, 2H), 7.78 (d, J=8.22 Hz, 1H), 9.11 (s, 1H)

$^{13}$C NMR (151 MHz, CDCl$_3$) δ: 19.52, 27.20, 30.91, 46.63, 59.39, 66.80, 70.11, 84.41, 86.66, 87.77, 102.95, 128.23, 128.28, 130.43, 130.51, 131.84, 132.68, 135.39, 135.68, 139.93, 150.31, 163.09

4'-C-azidoethyl-2'-O-methyluridine 24

1 M tetrabutyl ammonium fluoride tetrahydrofuran solution (TBAF) (1.85 mL, 1.85 mmol) was added in an argon atmosphere to a tetrahydrofuran solution (7.0 mL) of 5'-O-[(1,1-dimethylethyl)diphenylsilyl]-4'-C-azidoethyl-2'-O-methyluridine (0.693 g, 1.23 mmol), and stirred for 21 hours at room temperature. The solvent was then distilled off under reduced pressure, and the residue was purified by silica gel column chromatography [chloroform-methanol, 8:1, v/v] to obtain a target substance 24 (0.390 g, 1.19 mmol, 97%).

$^1$H NMR (500 MHz, DMSO-d$_6$) δ: 0.901-0.961 (m, 1H), 1.08-1.14 (m, 1H), 2.45 (s, 3H), 2.50-2.63 (m, 4H), 3.14 (t, J=6.30 Hz, 1H), 3.33 (t, J=5.75 Hz, 1H), 4.44-4.48 (m, 2H), 4.83 (d, J=8.05 Hz, 11H), 5.07 (d, J=6.90 Hz, 1H), 7.05 (d, 8.05 Hz, 1H), 10.5 (s, 1H)

$^{13}$C NMR (101 MHz, DMSO-d$_6$) δ: 30.99, 46.38, 57.45, 64.27, 69.70, 82.28, 84.98, 87.21, 102.34, 140.62, 150.75, 163.02

5'-O-[bis(4-methoxyphenyl)phenylmethyl]-4'-C-azidoethyl-2'-O-methyluridine 25

4,4'-dimethoxytrityl chloride (DMTrCl) (0.569 g, 1.68 mmol) was added in an argon atmosphere to a pyridine solution (4.0 mL) of 4'-C-azidoethyl-2'-O-methyluridine (0.365 g, 1.12 mmol), and stirred for 20 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 25 (0.365 g, 1.12 mmol, 96%).

$^1$H NMR (400 MHz, CDCl$_3$) δ: 1.74-1.81 (m, 1H), 2.08-2.11 (m, 11H), 2.87 (d, J=6.44 Hz, 11H), 3.18-3.23 (m, 1H), 3.26-3.30 (m, 1H), 3.35 (s, 2H), 3.58 (s, 3H), 3.80 (s, 6H), 3.93 (dd, J=5.96 Hz and 3.64 Hz, 1H), 4.10-4.15 (m, 11H), 4.61 (t, J=6.40 Hz, 1H), 5.22 (d, J=8.24 Hz, 11H), 6.03 (d, J=3.64 Hz, 1H), 6.85 (d, J=9.16 Hz, 4H), 7.24-7.25 (m, 2H), 7.26-7.35 (m, 7H), 7.81 (d, J=8.24 Hz, 1H), 8.50 (s, 1H)

5'-O-[bis(4-methoxyphenyl)phenylmethyl]-4'-C-trifluoroacetylaminoethyl-2'-O-methyluridine 26

Triphenylphosphine (PPh$_3$) (0.708 g, 2.70 mmol) and water (0.798 mL) were added to a tetrahydrofuran solution (25 mL) of 5'-O-[bis(4-methoxyphenyl)phenylmethyl]-4'-C-azidoethyl-2'-O-methyluridine (0.679 g, 1.08 mmol), and stirred for 23 hours at 45° C. The tetrahydrofuran in the reaction mixture was distilled off under reduced pressure, and a dichloromethane (6.8 mL) solution was obtained. Ethyl trifluoroacetate (CF$_3$COOEt) (0.387 mL, 3.24 mmol) and triethylamine (Et$_3$N) (0.558 mL, 1.626 mmol) were added, and stirred overnight at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 2:3, v/v] to obtain a target substance 26 (1.12 g, 1.39 mmol, 92%).

$^1$H NMR (600 MHz, CDCl$_3$) δ: 1.94-1.97 (m, 1H), 2.03-2.08 (m, 1H), 3.05 (d, J=4.60 Hz, 1H), 3.31-3.41 (m, 4H), 3.54 (s, 3H), 3.80 (s, 6H), 4.03 (t, J=5.04 Hz, 1H), 4.47 (t, J=5.04 Hz, 1H), 5.29 (d, J=8.24 Hz, 1H), 6.03 (d, J=5.04

Hz, 1H), 6.85 (d, J=8.76 Hz, 4H), 7.23-7.25 (m, 2H), 7.28-7.34 (m, 7H), 8.18 (s, 1H)

5'-O-[bis(4-methoxyphenyl)phenylmethyl]-4'-C-trifluoroacetylaminoethyl-2'-O-methyl-3'-[2-cyanoethyl-N,N-bis(1-methylethyl)-phosphoramidite]-uridine 27

Diisopropyl ethylamine (DIPEA) (1.25 mL, 7.15 mmol) and 2-cyanoethyl N,N-diisopropylchlorophosphoramidite (CEP-Cl) (0.638 mL, 2.86 mmol) were added in an argon atmosphere to a tetrahydrofuran solution (10 mL) of 5'-O-[bis(4-methoxyphenyl)phenylmethyl]-4'-C-trifluoroacetylaminoethyl-2'-O-methyluridine (1.00 g, 1.43 mmol), and stirred for 1.5 hours at room temperature. The reaction mixture was extracted with chloroform, and the organic layer was washed with saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 27 (0.884 g, 0.983 mmol, 69%).

$^{31}$P NMR (162 MHz, CDCl$_3$) δ: 150.94, 151.53

(4) 2'OH-4' Aminopropyl Amidite Unit and Resin Body

A 2'OH-4' aminopropyl amidite unit and resin body were synthesized according to the following scheme.

[C12]

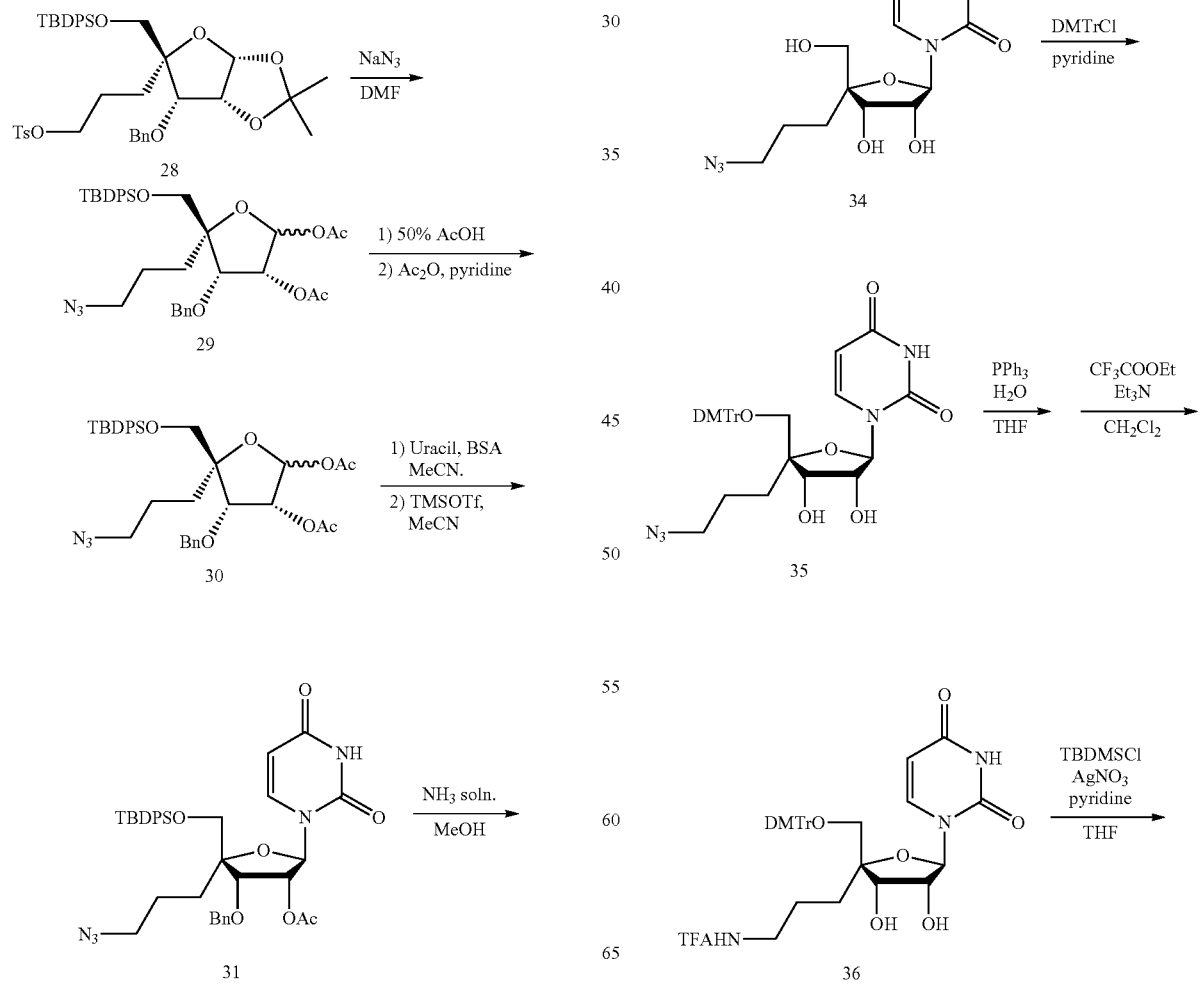

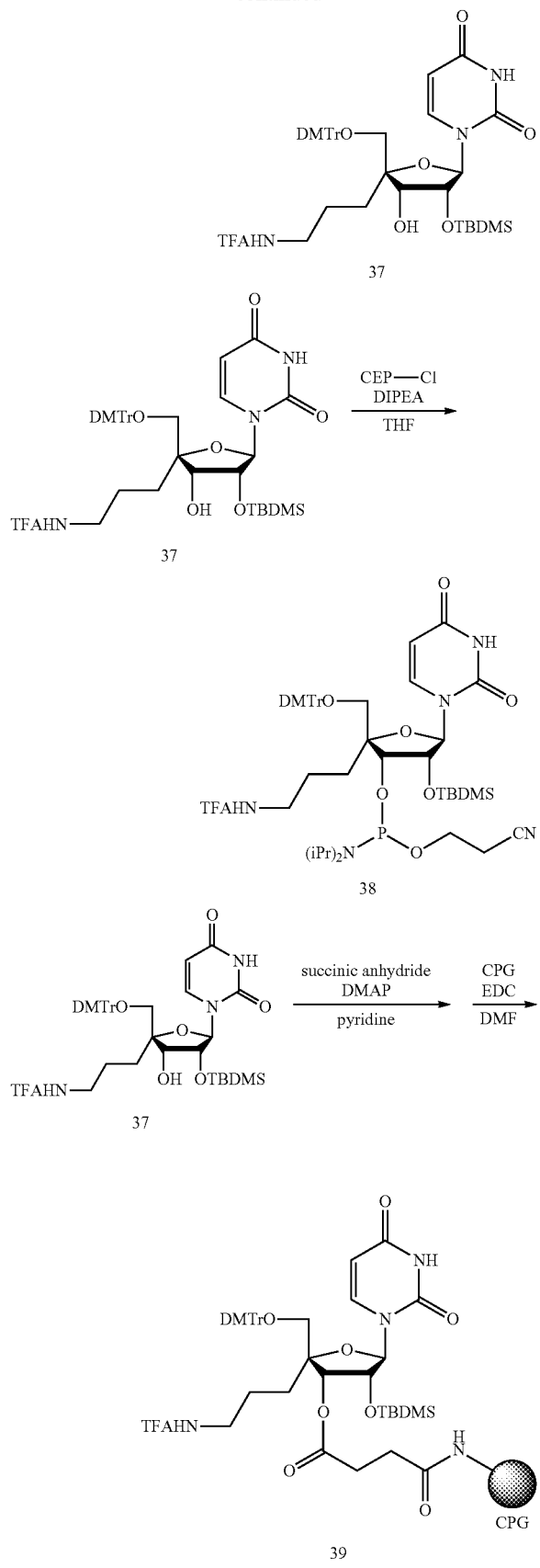

5-O-[(1,1-dimethylethyl)diphenylsilyl]-4-C-azidopropyl-3-O-benzyl-1,2-O-(1-methylethylidene)-α-D-ribofuranose 29

Sodium azide (NaN$_3$) (6.59 g, 101 mmol) was added in an argon atmosphere to a dimethylformamide (DMF) solution (90 mL) of 5-O-[(1,1-dimethylethyl)diphenylsilyl]-4-C-{[(4-methylphenyl)sulfonyl]oxy}propyl-3-O-benzyl-1,2-O-(1-methylethylidene)-α-D-ribofuranose (8.82 g, 12.1 mmol), and stirred overnight at 60° C. An ethyl acetate solution of the reaction mixture was washed with saturated saline. The organic layer was then dried with anhydrous sodium sulfate, filtered, and concentrated under reduced pressure. The residue was purified by silica gel column chromatography [hexane-ethyl acetate, 15:1, v/v] to obtain a target substance 29 (5.98 g, 9.94 mmol, 82%) as a white oily substance.

$^1$H NMR (400 MHz, CDCl$_3$) δ: 0.98 (s, 9H, TBDPS), 1.36 (s, 3H, CH$_3$), 1.35-1.41 (m, 1H, 4-(C)—CH), 1.55-1.57 (m, 1H, 4-(C)—CH), 1.62 (s, 3H, CH$_3$), 1.73-1.78 (m, 1H, 4-(C—CH$_2$)—CH), 2.09-2.13 (m, 1H, 4-(C—CH$_2$)—CH), 3.18-3.23 (m, 2H, 4-(C—CH$_2$—CH$_2$)—CH$_2$), 3.41 (d, J=11.0 Hz, 1H, 5-H), 3.65 (d, J=11.0 Hz, 1H, 5-H), 4.30 (d, J=5.48 Hz, 11H, 3-H), 4.59 (d, J=12.4 Hz, 1H, Bn), 4.67 (dd, J=5.52 Hz and 3.64 Hz, 11H, 2-H), 4.82 (d, J=12.4 Hz, 11H, Bn), 5.79 (d, J=3.68 Hz, 1H, 1-H), 7.30-7.46 (m, 10H, TBDPS), 7.59-7.64 (m, 5H, Bn)

$^{13}$C NMR (101 MHz, CDCl$_3$) δ: 19.33, 23.28, 26.32, 26.92, 29.03, 52.19, 66.46, 72.55, 78.12, 79.45, 87.53, 104.30, 113.32, 127.86, 127.88, 128.58, 129.85, 129.93, 132.99, 133.29, 135.68, 135.77, 138.05

HRMS (ESI) m/z Calcd for C$_{34}$H$_{43}$N$_3$O$_5$SiNa (M+Na)$^+$; 624.28697 found 624.28993.

5-O-[(1,1-dimethylethyl)diphenylsilyl]-4-C-azidopropyl-3-O-benzyl-1,2-di-O-acetyl-α-D-ribofuranose 30

50% acetic acid (5.70 mL) was added to dissolve 5-O-[(1,1-dimethylethyl)diphenylsilyl]-4-C-azidopropyl-3-O-benzyl-1,2-O-(1-methylethylidene)-α-D-ribofuranose (0.40 g, 0.665 mmol), and heat refluxed for 1 hour at 120° C. The reaction mixture was dried azeotropically with ethanol, pyridine (1.43 mL, 17.7 mmol) and acetic anhydride (Ac$_2$O) (0.95 mL, 10.2 mmol) were added, and the mixture was stirred overnight at room temperature in an argon atmosphere. The reaction mixture was cooled in an ice bath, poured into cold water, and extracted with ethyl acetate. The organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 5:1, v/v] to obtain a target substance 30 (0.314 g, 0.486 mmol, 74%) as a colorless oily substance.

$^1$H NMR (400 MHz, CDCl$_3$) δ: 1.06 (s, 9H, TBDPS), 1.10-1.14 (m, 1H, 4-(C)—CH), 1.54-1.58 (m, 1H, 4-(C)—CH), 1.74-1.77 (m, 1H, 4-(C—CH$_2$)—CH), 1.82 (s, 3H, CH$_3$), 1.84-1.90 (m, 1H, 4-(C—CH$_2$)—CH), 2.10 (s, 3H, CH$_3$), 3.19-3.23 (m, 2H, 4-(C—CH$_2$—CH$_2$)—CH$_2$), 3.59 (dd, J=10.6 Hz and 13.3 Hz, 2H, 5-H$_2$), 4.38 (d, J=5.52 Hz, 1H, 3-H), 4.54 (d, J=11.4 Hz, 1H, Bn), 4.60 (d, J=11.4 Hz, 11H, Bn), 5.36 (d, J=5.48 Hz, 11H, 2-H), 6.13 (s, 1H, 1-H), 7.27-7.64 (m, 15H, Bn and TBDPS)

$^{13}$C NMR (101 MHz, CDCl$_3$) δ: 19.48, 20.95, 22.91, 27.05, 29.50, 52.12, 67.42, 73.63, 74.93, 79.26, 88.12, 97.87, 127.63, 127.74, 127.91, 127.97, 130.08, 132.88, 133.20, 135.66, 135.76, 169.45, 169.90

HRMS (ESI) m/z Calcd for C$_{35}$H$_{43}$N$_3$O$_7$SiNa (M+Na)$^+$; 668.27680 found 668.27474.

5'-O-[(1,1-dimethylethyl)diphenylsilyl]-4'-C-azidoepropyl-3'-O-benzyl-2'-O-acetyluridine 31

Uracil (0.957 g, 8.54 mmol) and N,O-bis(trimethylsilyl)acetamide (BSA) (11.1 mL, 34.2 mmol) were added to an acetonitrile solution (28 mL) of 5-O-[(1,1-dimethylethyl)diphenylsilyl]-4-C-azidopropyl-3-O-benzyl-1,2-di-O-acetyl-α-D-ribofuranose (2.76 g, 4.27 mmol) in an argon atmosphere, and heat refluxed for 1 hour at 95° C. This was cooled to 0° C., and trimethylsilyl trifluoromethanesulfonate (TMSOTf) (1.55 mL, 8.54 mmol) was carefully dripped in. This was then heat refluxed again for 15 minutes at 95° C. and then cooled in an ice bath, and saturated sodium bicarbonate solution was added. The reaction mixture was extracted with chloroform, and the organic layer was washed with saturated sodium bicarbonate solution. The organic layer was then dried with anhydrous sodium sulfate, filtered, and concentrated under reduced pressure. The residue was purified by silica gel column chromatography [hexane-ethyl acetate, 2:1, v/v] to obtain a target substance 31 (2.27 g, 3.26 mmol, 76%).

$^1$H NMR (400 MHz, CDCl$_3$) δ: 1.09 (s, 9H, TBDPS), 1.45-1.51 (m, 2H, 4'-(C)—CH$_2$), 1.64-1.69 (m, 1H, 4'-(C—CH$_2$)—CH), 1.82-1.89 (m, 1H, 4'-(C—CH$_2$)—CH), 2.11 (s, 3H, CH$_3$), 3.18-3.24 (m, 2H, 4'-(C—CH$_2$—CH$_2$)—CH$_2$), 3.56 (d, J=11.4 Hz, 1H, 5'-H), 3.84 (d, J=10.9 Hz, 1H, 5'-H), 4.39-4.44 (m, 2H, 3'-H and Bn), 4.61 (d, J=11.0 Hz, 1H, Bn), 5.32-5.48 (m, 2H, 2'-H and 6-H), 6.18 (d, J=5.04 Hz, 1H, 1'-H), 7.28-7.57 (m, 15H, Bn and TBDPS), 7.67 (d, J=8.24 Hz, 1H, 5'-H), 8.66 (s, 1H, 3-NH)

$^{13}$C NMR (101 MHz, CDCl$_3$) δ: 19.46, 20.90, 23.01, 23.12, 26.96, 27.17, 29.18, 51.88, 66.51, 74.63, 75.09, 77.76, 86.30, 88.18, 103.03, 128.01, 128.07, 128.20, 128.25, 128.68, 130.34, 130.46, 131.96, 132.68, 135.45, 135.68, 135.77, 137.30, 139.83, 150.28, 162.84, 170.17 HRMS (ESI) m/z Calcd for C$_{37}$H$_{43}$N$_5$O$_7$SiNa (M+Na)$^+$; 720.28294 found 720.28484.

5'-O-[(1,1-dimethylethyl)diphenylsilyl]-4'-C-azidopropyl-3'-O-benzyluridine 32

Ammonia water (16 mL) and methanol (16 mL) were added to 5'-O-[(1,1-dimethylethyl)diphenylsilyl]-4'-C-azidoepropyl-3'-O-benzyl-2'-O-acetyluridine (1.57 g, 2.24 mmol), and stirred overnight at room temperature. Ethanol was added to the reaction mixture, which was then concentrated under reduced pressure. The residue was purified by silica gel column chromatography [hexane-ethyl acetate, 2:1, v/v] to obtain a target substance 32 (1.44 g, 2.19 mmol, 98%).

$^1$H NMR (400 MHz, CDCl$_3$) δ: 1.09 (s, 9H, TBDPS), 1.37-1.41 (m, 1H, 4'-(C)—CH), 1.51-1.55 (m, 1H, 4'-(C)—CH), 1.61-1.68 (m, 1H, 4'-(C—CH$_2$)—CH), 1.85-1.89 (m, 1H, 4'-(C—CH$_2$)—CH), 3.13-3.19 (m, 2H, 4'-(C—CH$_2$—CH$_2$)—CH$_2$), 3.55 (d, J=11.0 Hz, 1H, 5'-H), 3.60 (d, J=7.80 Hz, 1H, 2'-OH), 3.78 (d, J=11.0 Hz, 1H, 5'-H), 4.19 (d, J=5.96 Hz, 1H, 3'-H), 4.29 (dd, J=5.96 Hz and 12.36 Hz, 1H, 2'-H), 4.59 (d, J=11.4 Hz, 1H, Bn), 4.74 (d, J=11.5 Hz, 1H, Bn), 5.39 (d, J=8.24 Hz, 1H, 6-H), 5.94 (d, J=5.52 Hz, 1H, 1'-H), 7.34-7.60 (m, 15H, Bn and TBDPS), 7.69 (d, J=7.80 Hz, 1H, 5-H), 9.37 (s, 1H, 3-NH)

$^{13}$C NMR (101 MHz, CDCl$_3$) δ: 19.42, 22.99, 27.16, 29.36, 51.92, 66.76, 74.66, 75.15, 78.84, 87.92, 88.94, 102.80, 128.17, 128.21, 128.31, 128.45, 128.78, 130.32, 130.42, 132.05, 132.64, 135.45, 135.73, 137.12, 139.95, 151.00, 163.16 HRMS (ESI) m/z Calcd for C$_{35}$H$_{41}$N$_5$O$_6$SiNa (M+Na)$^+$; 678.27238 found 678.27027.

5'-O-[(1,1-dimethylethyl)diphenylsilyl]-4'-C-azidopropyluridine 33

A dichloromethane solution (72 mL) of 5'-O-[(1,1-dimethylethyl)diphenylsilyl]-4'-C-azidopropyl-3'-O-benzyluridine (1.80 g, 2.74 mmol) was cooled to −78° C. in an argon atmosphere, 1 M boron trichloride in dichloromethane (16.4 mL, 16.4 mmol) was added, and the mixture was stirred for 3 hours. The temperature was then raised to −30° C., and the mixture was stirred for 3 hours. Dichloromethane-methanol (1:1 v/v, 40 mL) was added to the reaction mixture, which was then concentrated under reduced pressure. The residue was purified by silica gel column chromatography [hexane-ethyl acetate, 2:3, v/v] to obtain a target substance 33 (1.31 g, 2.32 mmol, 85%).

$^1$H NMR (400 MHz, CDCl$_3$) δ: 1.08 (s, 9H, TBDPS), 1.52-1.71 (m, 3H, 4'-(C)—CH$_2$—CH), 1.87-1.98 (in, 1H, 4'-(C—CH$_2$)—CH), 3.20-3.27 (m, 2H, 4'-(C—CH$_2$—CH$_2$)—CH$_2$), 3.39 (s, 1H, 3'-OH), 3.66 (d, J=11.0 Hz, 1H, 5'-H), 3.77 (d, J=11.5 Hz, 1H, 5'-H), 4.32-4.36 (m, 1H, 3'-H), 4.38-4.42 (m, 1H, 2'-H), 5.15 (s, 1H, 2'-OH), 5.39 (d, J=7.8 Hz, 1H, 6-H), 5.94 (d, J=5.48 Hz, 1H, 1'-H), 7.39-7.66 (m, 10H, TBDPS), 7.77 (d, J=8.24 Hz, 1H, 5-H), 10.24 (s, 1H, 3-NH)

$^{13}$C NMR (101 MHz, CDCl$_3$) δ: 19.42, 23.33, 27.14, 29.14, 51.88, 67.01, 72.23, 76.21, 89.57, 102.51, 128.22, 130.33, 130.43, 132.03, 132.65, 135.51, 135.74, 140.32, 151.81, 163.70 HRMS (ESI) m/z Calcd for C$_{25}$H$_{35}$N$_5$O$_6$SiNa (M+Na)$^+$; 588.22543 found 588.22729.

4'-C-azidopropyluridine 34

1 M tetrabutyl ammonium fluoride tetrahydrofuran solution (TBAF) (5.49 mL, 5.49 mmol) was added in an argon atmosphere to a tetrahydrofuran solution (21.0 mL) of 5'-O-[(1,1-dimethylethyl)diphenylsilyl]-4'-C-azidopropyluridine (2.07 g, 3.66 mmol), and stirred overnight at room temperature. The solvent was then distilled off under reduced pressure, and the residue was purified by silica gel column chromatography [chloroform-methanol, 5:1, v/v] to obtain a target substance 34 (1.16 g, 3.55 mmol, 97%) as a colorless amorphous substance.

$^1$H NMR (400 MHz, DMSO-d$_6$) δ: 1.52-1.68 (m, 4H, 4'-(C)—CH$_2$—CH$_2$), 3.26-3.35 (m, 2H, 4'-(C—CH$_2$—CH$_2$)—CH$_2$), 3.42-3.49 (m, 2H, 5'-H$_2$), 3.94-3.96 (m, 1H, 3'-H), 4.21-4.22 (m, 1H, 2'-H), 5.07 (d, J=4.60 Hz, 1H, 3'-OH), 5.15 (s, 1H, 5'-OH), 5.24 (d, J=6.44 Hz, 1H, 2'-OH), 5.65 (d, J=8.24 Hz, 1H, 6-H), 5.80 (d, J=7.80 Hz, 1H, 1'-H), 7.83 (d, J=8.24 Hz, 1H, 5-H), 11.28 (s, 1H, 3-NH)

$^{13}$C NMR (101 MHz, DMSO-d$_6$) δ: 22.87, 29.32, 51.41, 64.60, 71.85, 73.29, 86.05, 87.48, 102.18, 140.90, 151.07, 163.10

HRMS (ESI) m/z Calcd for C$_{12}$H$_{17}$N$_5$O$_6$Na (M+Na)$^+$; 350.10765 found 350.10522.

5'-O-[bis(4-methoxyphenyl)phenylmethyl]-4'-C-azidopropyluridine 35

4,4'-dimethoxytrityl chloride (DMTrCl) (0.497 g, 1.47 mmol) was added in an argon atmosphere to a pyridine solution (3.0 mL) of 4'-C-azidopropyluridine (0.30 g, 0.917 mmol), and stirred for 5.5 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 35 (0.331 g, 0.526 mmol, 57%).

$^1$H NMR (400 MHz, CDCl$_3$) δ: 1.46-1.56 (m, 2H, 4'-(C)—CH$_2$), 1.70-1.78 (m, 1H, 4'-(C—CH$_2$)—CH), 1.87-

1.94 (m, 1H, 4'-(C—CH$_2$)—CH), 3.21-3.24 (m, 2H, 4'-(C—CH$_2$—CH$_2$)—CH$_2$), 3.27 (s, 2H, 5'-H$_2$), 3.41 (d, J=4.12 Hz, 1H, 3'-H), 3.78 (s, 6H, DMTr), 4.42 (d, J=4.12 Hz, 1H, 2'-H), 4.45 (s, 1H, 3'-OH), 5.15 (s, 1H, 2'-OH), 5.39 (d, J=7.80 Hz, 1H, 6-H), 5.91 (d, J=5.04 Hz, 1H, 1'-H), 6.85-7.31 (m, 13H, DMTr), 7.74 (d, J=8.28 Hz, 1H, 5-H), 10.12 (s, 1H, 3-NH)

$^{13}$C NMR (101 MHz, CDCl$_3$) δ: 23.24, 29.60, 51.83, 55.36, 65.89, 72.52, 76.16, 87.40, 89.01, 89.85, 102.42, 113.43, 127.32, 128.19, 130.24, 135.01, 135.15, 140.51, 144.19, 151.74, 158.80, 163.72

HRMS (ESI) m/z Calcd for C$_{33}$H$_{35}$N$_5$O$_8$Na (M+Na)$^+$; 652.23833 found 652.23622.

5'-O-[bis(4-methoxyphenyl)phenylmethyl]-4'-C-trifluoroacetylaminopropyluridine 36

Triphenylphosphine (PPh$_3$) (1.27 g, 4.85 mmol) and water (1.40 mL, 77.6 mmol) were added to a tetrahydrofuran solution (35 mL) of 5'-O-[bis(4-methoxyphenyl)phenylmethyl]-4'-C-azidopropyluridine (1.22 g, 1.94 mmol), and stirred for 8 hours at 45° C. The tetrahydrofuran in the reaction mixture was distilled off under reduced pressure, and a dichloromethane (12 mL) solution was obtained. Ethyl trifluoroacetate (CF$_3$COOEt) (0.69 mL, 5.82 mmol) and triethylamine (Et$_3$N) (0.40 mL, 2.91 mmol) were added, and stirred for 24 hours at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 36 (1.09 g, 1.55 mmol, 80%).

$^1$H NMR (400 MHz, CDCl$_3$) δ: 1.34-1.55 (m, 4H, 4'-(C)—CH$_2$—CH$_2$), 1.68-1.84 (m, 2H, 4'-(C—CH$_2$—CH$_2$)—CH$_2$), 3.23-3.31 (m, 4H, 5'-H$_2$ and 2'-OH and 3'-OH), 3.77 (s, 6H, DMTr), 4.20-4.26 (m, 1H, —NHCOCF$_3$), 4.40 (d, J=5.48 Hz, 1H, 3'-H), 4.53 (t, J=5.96 Hz, 1H, 2'-H), 5.38 (d, J=7.80 Hz, 1H, 6-H), 5.98 (d, J=5.96 Hz, 1H, 1'-H), 6.84-7.38 (m, 13H, DMTr), 7.69 (d, J=7.80 Hz, 1H, 5-H), 10.35 (s, 1H, 3-NH)

$^{13}$C NMR (101 MHz, CDCl$_3$) δ: 11.06, 23.08, 23.81, 29.01, 30.43, 38.79, 55.31, 68.26, 72.78, 75.49, 87.44, 88.51, 88.67, 113.42, 127.30, 128.17, 128.90, 130.21, 131.02, 134.93, 135.08, 144.14, 151.83, 158.78, 163.86

HRMS (ESI) m/z Calcd for C$_{35}$H$_{36}$F$_3$N$_3$O$_9$Na (M+Na)$^+$; 722.23013 found 722.23205.

5'-O-[bis(4-methoxyphenyl)phenylmethyl]-4'-C-trifluoroacetylaminopropyl-2'-O-[(1,1-dimethylethyl)dimethylsilyl]-uridine 37

Pyridine (0.955 mL, 11.8 mmol), silver nitrate (AgNO$_3$) (0.560 g, 3.30 mmol) and tert-butyldimethylsilyl chloride (TBDMSCl) (0.526 g, 3.49 mmol) were added in an argon atmosphere to a tetrahydrofuran solution (14 mL) of 5'-O-[bis(4-methoxyphenyl)phenylmethyl]-4'-C-trifluoroacetylaminopropyluridine (1.36 g, 1.94 mmol), and stirred for 4 hours at room temperature. The reaction mixture was diluted with chloroform, filtered through Celite, and concentrated under reduced pressure. The residue was purified by silica gel column chromatography [hexane-ethyl acetate, 3:2, v/v] to obtain a target substance 37 (1.34 g, 1.64 mmol, 85%) as a colorless amorphous substance.

$^1$H NMR (400 MHz, CDCl$_3$) δ: 0.0547 (s, 3H, TBDMS), 0.119 (s, 3H, TBDMS), 0.915 (s, 9H, TBDMS), 1.47-1.57 (m, 4H, 4'-(C)—CH$_2$—CH$_2$), 1.69-1.74 (m, 2H, 4'-(C—CH$_2$—CH$_2$)—CH$_2$), 3.05 (s, 1H, 3'-OH), 3.22-3.25 (m, 2H, 5'-H$_2$), 3.31-3.34 (m, 1H, —NHCOCF$_3$), 3.81 (s, 6H, DMTr), 4.26 (d, J=5.52 Hz, 1H, 3'-H), 4.62 (dd, J=5.52 Hz and 6.84 Hz, 1H, 2'-H), 5.33 (d, J=8.28 Hz, 1H, 6-H), 6.04 (d, J=7.32 Hz, 1H, 1'-H), 6.84-7.32 (m, 13H, DMTr), 7.71 (d, J=8.24 Hz, 1H, 5-H), 8.11 (s, 1H, 3-NH)

$^{13}$C NMR (101 MHz, CDCl$_3$) δ: 18.01, 22.93, 25.61, 30.26, 40.27, 55.40, 67.43, 73.12, 75.88, 86.89, 87.96, 102.96, 113.53, 127.54, 128.16, 128.28, 130.19, 130.30, 134.63, 134.80, 140.36, 144.08, 150.49, 157.55, 158.98, 162.82 HRMS (ESI) m/z Calcd for C$_{41}$H$_{50}$F$_3$N$_3$O$_9$SiNa (M+Na)$^+$; 836.31661 found 836.31586.

5'-O-[bis(4-methoxyphenyl)phenylmethyl]-4'-C-trifluoroaminopropyl-2'-O-[(1,1-dimethylethyl)dimethylsilyl]-3'-[2-cyanoethyl-N,N-bis(1-methylethyl)-phosphoramidite]-uridine 38

Diisopropyl ethylamine (DIPEA) (1.21 mL, 6.95 mmol) and 2-cyanoethyl N,N-diisopropylchlorophosphoramidite (CEP-Cl) (0.620 mL, 2.78 mmol) were added in an argon atmosphere to a tetrahydrofuran solution (11 mL) of 5'-O-[bis(4-methoxyphenyl)phenylmethyl]-4'-C-trifluoroacetylaminopropyl-2'-O-[(1,1-dimethylethyl)dimethylsilyl]-uridine (1.13 g, 1.39 mmol), and stirred for 1.5 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:2, v/v] to obtain a target substance 38 (1.25 g, 1.23 mmol, 88%).

$^{31}$P NMR (202 MHz, CDCl$_3$) δ: 149.4626, 151.1583

HRMS (ESI) m/z Calcd for C$_{50}$H$_{67}$F$_3$N$_5$O$_{10}$PSiNa (M+Na)$^+$; 1036.42446 found 1036.42397.

5'-O-[bis(4-methoxyphenyl)phenylmethyl]-4'-C-trifluoroacetylaminopropyl-2'-O-[(1,1-dimethylethyl)dimethylsilyl]-uridine carrying CPG carrier 39

N,N-dimethyl-4-aminopyridine (DMAP) (48.9 mg, 0.40 mmol) and succinic anhydride (80.1 mg, 0.80 mmol) were added in an argon atmosphere to a pyridine solution (1.7 mL) of 5'-O-[bis(4-methoxyphenyl)phenylmethyl]-4'-C-trifluoroacetylaminopropyl-2'-O-[(1,1-dimethylethyl)dimethylsilyl]-uridine (0.163 g, 0.20 mmol), and stirred for 23 hours at room temperature. The reaction mixture was extracted with ethyl acetate, and the organic layer was washed with saturated sodium bicarbonate solution. The organic layer was then dried with anhydrous sodium sulfate, filtered, and concentrated under reduced pressure. Dimethylformamide (1.98 mL) was added to dissolve the residue, and controlled pore glass (CPG) (0.326 g) and 1-(3-dimethylaminopropyl)-3-ethylcarbodiimide hydrochloride (EDC) (38.0 mg, 0.198 mmol) were added and shaken for 5 days. The CPG was filtered and washed with pyridine, after which DMAP (0.183 g), pyridine (13.5 mL) and acetic anhydride (1.5 mL) were added in an argon atmosphere and left standing for 16 hours. The CPG was filtered, and dried after washing with pyridine, ethanol and acetonitrile to obtain a target substance 39 (activity: 40.8 μmol/g).

(5) 2'OMe-4' Aminopropyl Amidite Unit and Resin Body

A 2'OMe-4' aminopropyl amidite unit and resin body were synthesized according to the following scheme.

[C13]

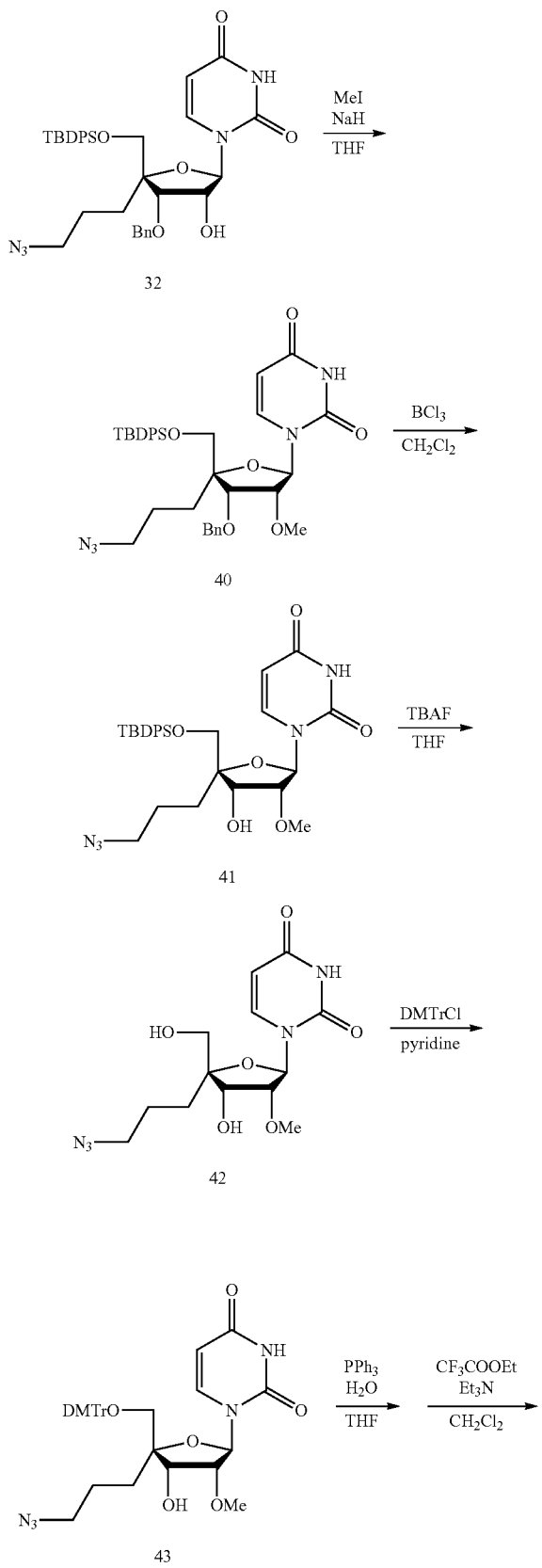

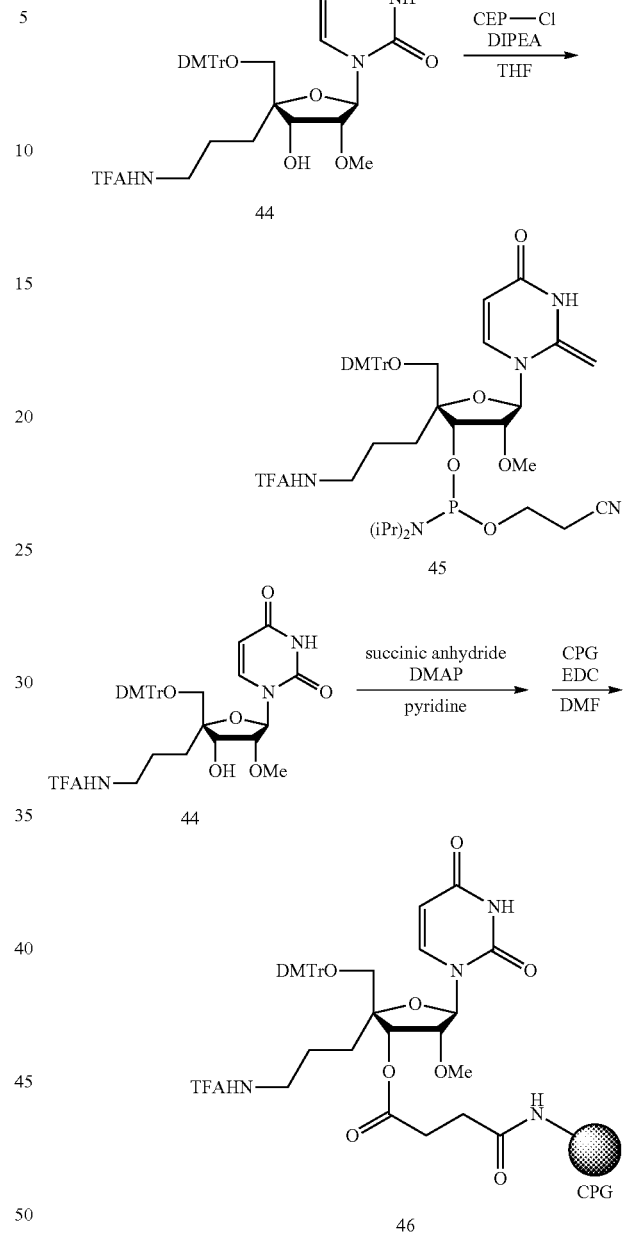

5'-O-[(1,1-dimethylethyl)diphenylsilyl]-4'-C-azidopropyl-3'-O-benzyl-2'-O-methyluridine 40

60% sodium hydride (NaH) (0.972 g, 24.3 mmol) was added in an ice bath in an argon atmosphere to a tetrahydrofuran solution (53 mL) of 5'-O-[(1,1-dimethylethyl)diphenylsilyl]-4'-C-azidopropyl-3'-O-benzyluridine (5.33 g, 8.10 mmol), and stirred for 10 minutes at 0° C. Iodomethane (CH₃I) (3.02 mL, 48.6 mmol) was then dripped carefully into this, and the mixture was shaken for 8 hours at 0° C. under shaded conditions. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 3:1, v/v) to obtain a target substance 40 (4.00 g, 5.98 mmol, 74%).

$^1$H NMR (400 MHz, CDCl$_3$) δ: 1.08 (s, 9H, TBDPS), 1.39-1.46 (m, 1H, 4'-(C)—CH), 1.52-1.60 (m, 1H, 4'-(C)—CH), 1.65-1.70 (m, 1H, 4'-(C—CH$_2$)—CH), 1.97-2.05 (m, 1H, 4'-(C—CH$_2$)—CH), 3.19-3.26 (m, 2H, 4'-(C—CH$_2$—CH$_2$)—CH$_2$), 3.51 (s, 3H, 2'-OCH$_3$), 3.68 (d, J=11.5 Hz, 1H, 5'-H), 3.74 (m, 1H, 2'-H), 3.95 (d, J=11.5 Hz, 1H, 5'-H), 4.35 (d, J=4.60 Hz, 1H, 3'-H), 4.52 (d, J=11.5 Hz, 1H, Bn), 4.73 (d, J=11.9 Hz, 1H, Bn), 5.12 (d, J=8.24 Hz, 1H, 6-H), 6.09 (s, 1H, 1'-H), 7.35-7.63 (m, 15H, Bn and TBDPS), 7.78 (d, J=8.24 Hz, 1H, 5-H), 9.04 (s, 1H, 3-NH)

$^{13}$C NMR (101 MHz, CDCl$_3$) δ: 19.56, 22.84, 27.26, 29.00, 51.85, 59.44, 65.37, 73.25, 75.93, 84.19, 87.95, 88.06, 102.59, 128.02, 128.09, 128.14, 128.25, 128.69, 130.29, 130.39, 132.07, 132.99, 135.36, 135.60, 137.49, 140.03, 150.09, 163.16

5'-O-[(1,1-dimethylethyl)diphenylsilyl]-4'-C-azidopropyl-2'-O-methyluridine 41

A dichloromethane solution (60 mL) of 5'-O-[(1,1-dimethylethyl)diphenylsilyl]-4'-C-azidopropyl-3'-O-benzyl-2'-O-methyluridine (4.00 g, 5.98 mmol) was cooled to −78° C. in an argon atmosphere, 1 M boron trichloride in dichloromethane (35.9 mL, 35.9 mmol) was added, and the mixture was stirred for 3 hours. The temperature was then raised to −30° C., and the mixture was stirred for 5 hours. Dichloromethane-methanol (1:1 v/v, 100 mL) was added to the reaction mixture, which was then concentrated under reduced pressure. The residue was purified by silica gel column chromatography [hexane-ethyl acetate, 1:1, v/v] to obtain a target substance 41 (2.99 g, 5.16 mmol, 86%).

$^1$H NMR (600 MHz, CDCl$_3$) δ: 1.11 (s, 9H, TBDPS), 1.49-1.56 (m, 2H, 4'-(C)—CH$_2$), 1.58-1.64 (m, 1H, 4'-(C—CH$_2$)—CH), 1.76-1.80 (m, 1H, 4'-(C—CH$_2$)—CH), 2.74 (d, J=5.52 Hz, 1H, 3'-OH), 3.21-3.25 (m, 2H, 4'-(C—CH$_2$—CH$_2$)—CH$_2$), 3.52 (s, 3H, 2'-OCH$_3$), 3.70 (d, J=11.0 Hz, 1H, 5'-H), 3.88 (d, J=11.0 Hz, 1H, 5'-H), 3.93 (m, 1H, 2'-H), 4.49 (t, J=5.46 Hz, 1H, 3'-H), 5.31 (d, J=8.28 Hz, 1H, 6-H), 6.06 (d, J=4.80 Hz, 1H, 1'-H), 7.41-7.66 (m, 10H, TBDPS), 7.08 (d, J=7.56 Hz, 1H, 5-H), 8.04 (s, 1H, 3-NH)

$^{13}$C NMR (101 MHz, CDCl$_3$) δ: 19.52, 23.10, 27.21, 28.98, 51.86, 59.37, 66.76, 70.09, 84.61, 86.50, 88.46, 102.90, 128.22, 128.27, 130.39, 130.48, 131.96, 132.81, 135.41, 135.70, 140.01, 150.37, 163.12

4'-C-azidopropyl-2'-O-methyluridine 42

A 1 M tetrabutyl ammonium fluoride tetrahydrofuran solution (TBAF) (7.74 mL, 7.74 mmol) was added in an argon atmosphere to a tetrahydrofuran solution (30.0 mL) of 5'-O-[(1,1-dimethylethyl)diphenylsilyl]-4'-C-azidopropyl-2'-O-methyluridine (2.99 g, 5.16 mmol), and stirred overnight at room temperature. The solvent was then distilled off under reduced pressure, and the residue was purified by silica gel column chromatography [chloroform-methanol, 10:1, v/v] to obtain a target substance 42 (1.68 g, 4.94 mmol, 96%).

$^1$H NMR (600 MHz, DMSO-d$_6$) δ: 1.55-1.67 (m, 4H, 4'-(C)—CH$_2$—CH$_2$), 3.27-3.29 (m, 2H, 4'-(C—CH$_2$—CH$_2$)—CH$_2$), 3.32 (s, 3H, 2'-OCH$_3$), 3.42-3.45 (m, 2H, 5'-H$_2$), 3.98 (dd, J=7.56 Hz and 4.80 Hz, 1H, 2'-H), 4.16 (t, J=5.46 Hz, 1H, 3'-H), 5.13 (d, J=6.18 Hz, 1H, 3'-OH), 5.20 (d, J=5.46 Hz, 1H, 5'-OH), 5.67 (d, J=8.28 Hz, 1H, 6-H), 5.90 (d, J=6.84 Hz, 1H, 1'-H), 7.89 (d, J=8.22 Hz, 1H, 5-H), 11.34 (s, 1H, 3-NH)

$^{13}$C NMR (101 MHz, DMSO-d$_6$) δ: 22.77, 29.13, 51.33, 57.32, 64.24, 69.61, 82.45, 84.68, 88.00, 102.27, 140.67, 150.74, 162.95

5'-O-[bis(4-methoxyphenyl)phenylmethyl]-4'-C-azidopropyl-2'-O-methyluridine 43

4,4'-dimethoxytrityl chloride (DMTrCl) (2.51 g, 7.41 mmol) was added in an argon atmosphere to a pyridine solution (17 mL) of 4'-C-azidopropyl-2'-O-methyluridine (1.68 g, 4.94 mmol), and stirred for 5 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 2:1, v/v] to obtain a target substance 43 (3.12 g, 4.85 mmol, 98%).

$^1$H NMR (400 MHz, CDCl$_3$) δ: 1.38-1.44 (m, 1H, 4'-(C)—CH), 1.54-1.64 (m, 2H, 4'-(C)—CH—CH), 1.78-1.84 (m, 1H, 4'-(C—CH$_2$)—CH), 2.77 (d, J=6.44 Hz, 1H, 3'-OH), 3.17-3.22 (m, 2H, 4'-(C—CH$_2$—CH$_2$)—CH$_2$), 3.34 (s, 2H, 5'-H$_2$), 3.57 (s, 3H, 2'-OCH$_3$), 3.80 (s, 6H, DMTr), 3.92 (dd, J=4.12 Hz and 5.96 Hz, 1H, 2'-H), 4.60 (t, J=5.96 Hz, 1H, 3'-H), 5.22 (d, J=8.24 Hz, 1H, 6-H), 6.02 (d, J=4.12 Hz, 1H, 1'-H), 6.84-7.36 (m, 13H, DMTr), 7.82 (d, J=8.24 Hz, 1H, 5-H), 8.09 (s, 1H, 3-NH)

$^{13}$C NMR (101 MHz, CDCl$_3$) δ: 14.33, 23.00, 29.32, 51.82, 55.40, 59.50, 60.52, 65.42, 70.55, 84.72, 86.84, 87.63, 87.98, 102.67, 113.48, 127.43, 128.19, 128.33, 130.29, 130.34, 134.96, 135.18, 140.33, 144.26, 150.28, 158.94, 158.99, 163.10

5'-O-[bis(4-methoxyphenyl)phenylmethyl]-4'-C-trifluoroacetylaminopropyl-2'-O-methyluridine 44

Triphenylphosphine (PPh$_3$) (3.18 g, 12.1 mmol) and water (3.50 mL, 194 mmol) were added to a tetrahydrofuran solution (62.4 mL) of 5'-O-[bis(4-methoxyphenyl)phenylmethyl]-4'-C-azidopropyl-2'-O-methyluridine (3.12 g, 4.85 mmol), and stirred for 20 hours at 45° C. The tetrahydrofuran in the reaction mixture was distilled off under reduced pressure, and a dichloromethane solution (30 mL) was obtained. Ethyl trifluoroacetate (CF$_3$COOEt) (1.74 mL, 14.5 mmol) and triethylamine (Et$_3$N) (1.00 mL, 7.28 mmol) were added, and stirred for 24 hours at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 44.

$^1$H NMR (400 MHz, CDCl$_3$) δ: 1.40-1.45 (m, 1H, 4'-(C)—CH), 1.51-1.54 (m, 1H, 4'-(C)—CH), 1.63-1.67 (m, 1H, 4'-(C—CH$_2$)—CH), 1.72-1.78 (m, 1H, 4'-(C—CH$_2$)—CH), 2.88 (d, J=4.56 Hz, 1H, 3'-OH), 3.25-3.28 (m, 2H, 4'-(C—CH$_2$—CH$_2$)—CH$_2$), 3.30 (d, J=10.5 Hz, 1H, 5'-H), 3.35 (d, J=10.1 Hz, 1H, 5'-H), 3.54 (s, 3H, 2'-OCH$_3$), 3.80 (s, 6H, DMTr), 4.03 (t, J=5.04 Hz, 1H, 2'-H), 4.54 (t, J=5.04 Hz, 1H, 3'-H), 5.26 (d, J=8.24 Hz, 1H, 6-H), 6.03 (d, J=5.04 Hz, 1H, 1'-H), 6.66 (m, 1H, —NHCOCF$_3$), 6.84-7.55 (m, 13H, DMTr), 7.74 (d, J=8.24 Hz, 1H, 5-H), 8.17 (s, 1H, 3-NH)

$^{13}$C NMR (101 MHz, CDCl$_3$) δ: 14.32, 22.78, 29.38, 40.20, 55.38, 59.30, 60.52, 65.89, 70.75, 84.28, 86.43, 87.71, 87.97, 102.79, 113.48, 127.45, 128.21, 128.28, 130.26, 130.32, 132.07, 133.11, 134.81, 135.03, 140.24, 144.14, 150.39, 158.94, 158.99, 163.03

5'-O-[bis(4-methoxyphenyl)phenylmethyl]-4'-C-trifluoroaminopropyl-2'-O-methyl-3'-[2-cyanoethyl-N,N-bis(1-methylethyl)-phosphoramidite]-uridine 45

Diisopropyl ethylamine (DIPEA) (1.90 mL, 10.9 mmol) and 2-cyanoethyl N,N-diisopropylchlorophosphoramidite (CEP-Cl) (0.97 mL, 4.34 mmol) were added in an argon atmosphere to a tetrahydrofuran solution (15 mL) of 5'-O-[bis(4-methoxyphenyl)phenylmethyl]-4'-C-trifluoroacetylaminopropyl-2'-O-methyluridine (1.55 g, 2.17 mmol), and stirred for 1.5 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 45 (1.57 g, 1.71 mmol, 79%). $^{31}$P NMR (243 MHz, CDCl$_3$) δ: 150.57, 151.44

5'-O-[bis(4-methoxyphenyl)phenylmethyl]-4'-C-trifluoroacetylaminopropyl-2'-O-methyluridine carrying CPG carrier 46

N,N-dimethyl-4-aminopyridine (DMAP) (48.9 mg, 0.40 mmol) and succinic anhydride (80.1 mg, 0.80 mmol) were added in an argon atmosphere to a pyridine solution (1.4 mL) of 5'-O-[bis(4-methoxyphenyl)phenylmethyl]-4'-C-trifluoroacetylaminopropyl-2'-O-methyluridine (0.142 g, 0.20 mmol), and stirred for 24 hours at room temperature. The reaction mixture was extracted with ethyl acetate, and the organic layer was washed with saturated sodium bicarbonate solution. The organic layer was then dried with anhydrous sodium sulfate, filtered, and concentrated under reduced pressure. Dimethylformamide (2.0 mL) was added to dissolve the residue, and controlled pore glass (CPG) (0.373 g) and 1-(3-dimethylaminopropyl)-3-ethylcarbodiimide hydrochloride (EDC) (38.3 mg, 0.20 mmol) were added and shaken for 4 days. The CPG was filtered and washed with pyridine, after which DMAP (0.183 g), pyridine (13.5 mL) and acetic anhydride (1.5 mL) were added in an argon atmosphere and left standing for 16 hours. The CPG was filtered, and dried after washing with pyridine, ethanol and acetonitrile to obtain a target substance 46 (activity: 35.8 µmol/g).

(6) 2'OMe-4' Guanidinomethyl Amidite Unit and Resin Body

A 2'OMe-4' guanidinomethyl amidite unit and resin body were synthesized according to the following scheme.

[C14]

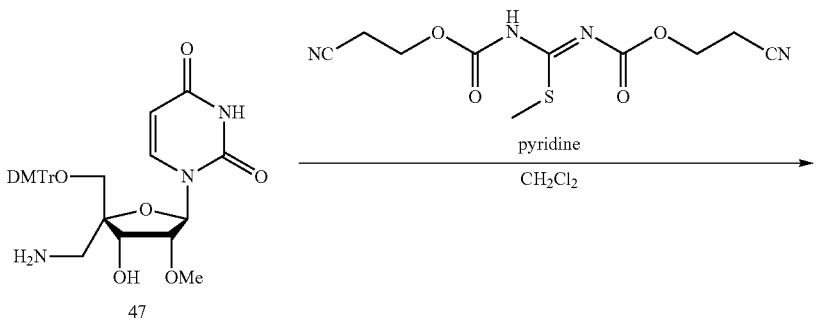

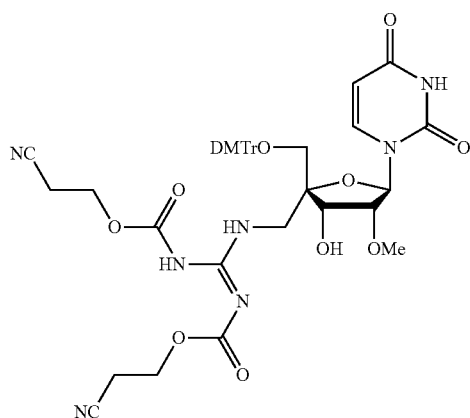

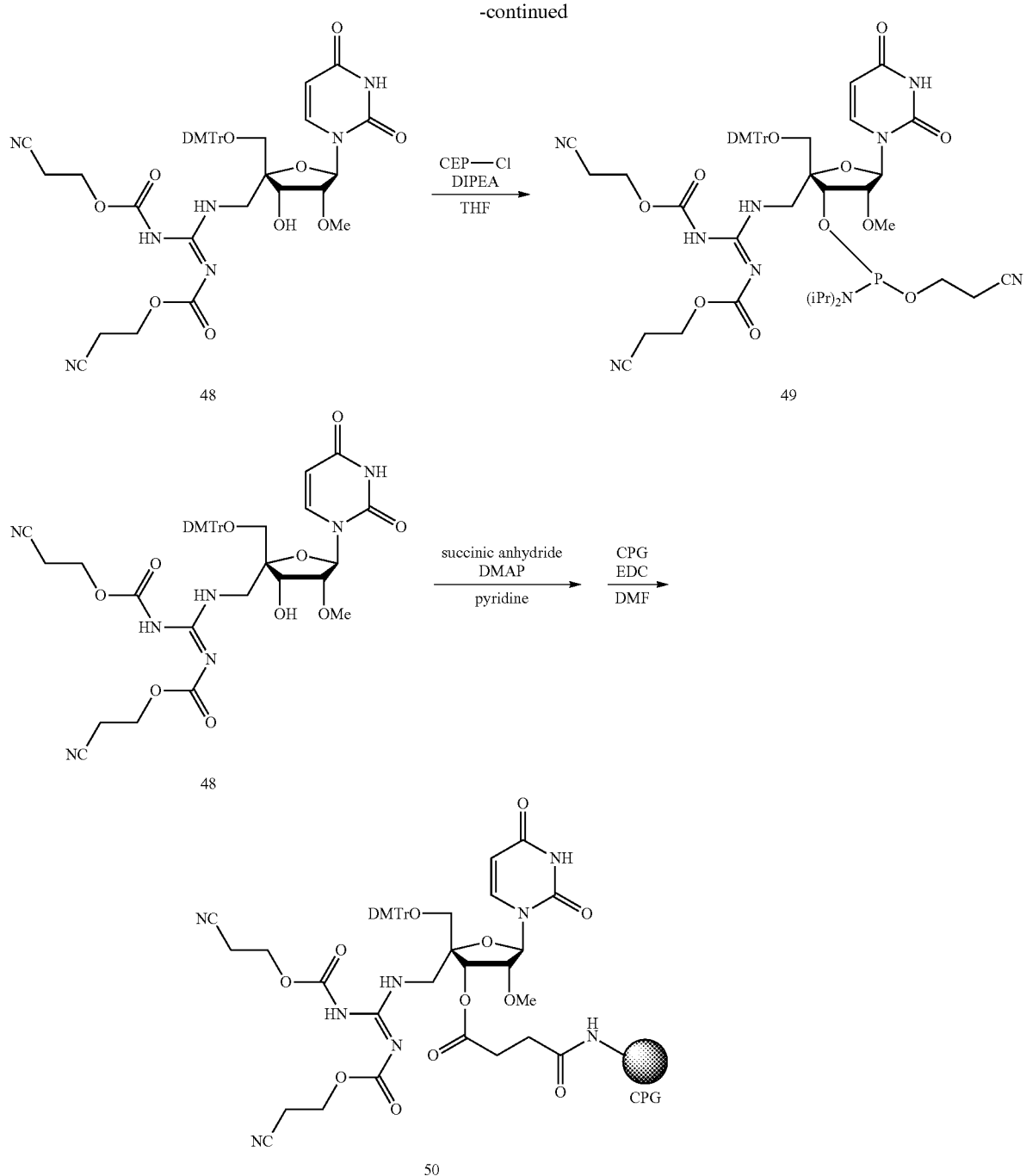

5'-O-(4,4'-dimethoxytrityl)-4'-C-aminomethyl-2'-O-methyluridine 47

A target substance 47 was synthesized by known methods using glucose as a starting material.

5'-O-(4,4'-dimethoxytrityl)-4'-C—{N,N'-bis-[(2-cyanoethoxy)carbonyl]guanidinyl}-2'-O-methyluridine 48

Activated 3 Å molecular sieves were added in an argon atmosphere to a dichloromethane solution (4.0 mL) of 5'-O-(4,4'-dimethoxytrityl)-4'-C-aminomethyl-2'-O-methyluridine (0.40 g, 0.679 mmol), and stirred for 15 minutes. A pyridine solution (0.263 mL, 3.26 mmol) of N,N'-Bis-[(2-cyanoethoxy)carbonyl]-S-methyl-isothiourea (0.463 g, 2.4 mmol) was added to this, and heat refluxed for 2 hours at 40° C. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography ethyl acetate to obtain a target substance 48 (0.35 g, 0.423 mmol, 62%).

$^1$H NMR (400 MHz, CDCl$_3$) δ: 1.88 (1H, s), 2.72 (2H, t, J=6.84 Hz), 2.80 (2H, t, J=6.44 Hz), 3.36 (1H, s, J=10.5 Hz), 3.41 (1H, d, J=11.0 Hz), 3.54 (3H, s), 3.69 (1H, dd, J=5.96 Hz), 3.83 (6H, s), 3.87 (1H, dd, J=7.8 Hz), 3.99 (1H, m), 4.3 (2H, t, J=6.44 Hz), 4.42-4.44 (2H, m), 4.56 (1H, t, J=5.92 Hz), 5.35 (1H, d, J=6.88 Hz), 6.10 (1H, d, J=4.12 Hz), 6.85

(4H, d, J=8.28 Hz), 7.26-7.37 (7H, m), 7.64 (1H, d, J=8.24 Hz), 8.65 (1H, t, J=5.96 Hz), 9.48 (1H, s), 11.63 (1H, s)

5'-O-(4,4'-dimethoxytrityl)-4'C—{N,N'-bis[(2-cyanoethoxy)carbonyl]guanidinyl}methyl-2'-O-methyl-3'-[2-cyanoethyl-N,N-bis(1-methylethyl)-phosphoramidite]-uridine 49

Diisopropyl ethylamine (DIPEA) (0.37 mL, 2.12 mmol) and 2-cyanoethyl N,N-diisopropylchlorophosphoramidite (CEP-Cl) (0.19 mL, 0.846 mmol) were added in an argon atmosphere to a tetrahydrofuran solution (3.5 mL) of 5'-O-(4,4'-dimethoxytrityl)-4'-C—{N,N'-bis-[(2-cyanoethoxy)carbonyl]guanidinyl}-2'-O-methyluridine (0.35 g, 0.423 mmol), and stirred for 1.5 hours at room temperature. The reaction mixture was extracted with chloroform, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:2, v/v] to obtain a target substance 49 (0.339 g, 0.330 mmol, 78%). $^{31}$P NMR (202 MHz, CDCl$_3$) δ: 151.8312, 152.1004

5'-O-[bis(4-methoxyphenyl)phenylmethyl]-4'-C-trifluoroacetylaminopropyl-2'-O-[(1,1-dimethylethyl)dimethylsilyl]-uridine carrying CPG carrier 50

N,N-dimethyl-4-aminopyridine (DMAP) (34.0 mg, 0.278 mmol) and succinic anhydride (56.0 mg, 0.556 mmol) were added in an argon atmosphere to a pyridine solution (1.0 mL) of 5'-O-(4,4'-dimethoxytrityl)-4'-C—{N,N'-bis-[(2-cyanoethoxy)carbonyl]guanidinyl}-2'-O-methyluridine (0.114 g, 0.139 mmol), and stirred for 25 hours at room temperature. The reaction mixture was extracted with ethyl acetate, and the organic layer was washed with saturated sodium bicarbonate solution. The organic layer was then dried with anhydrous sodium sulfate, filtered, and concentrated under reduced pressure. Dimethylformamide (1.28 mL) was added to dissolve the residue, and controlled pore glass (CPG) (0.192 g) and 1-(3-dimethylaminopropyl)-3-ethylcarbodiimide hydrochloride (EDC) (24.5 mg, 0.128 mmol) were added and shaken for 4 days. The CPG was filtered and washed with pyridine, after which DMAP (0.183 g), pyridine (13.5 mL) and acetic anhydride (1.5 mL) were added in an argon atmosphere and left standing for 65 hours. The CPG was filtered, and dried after washing with pyridine, ethanol and acetonitrile to obtain a target substance 50 (activity: 41.4 μmol/g).

(7) 2'OMe-4' Aminoethylcytosine Amidite Unit

A 2'OMe-4' aminoethylcytosine amidite unit was synthesized according to the following scheme.

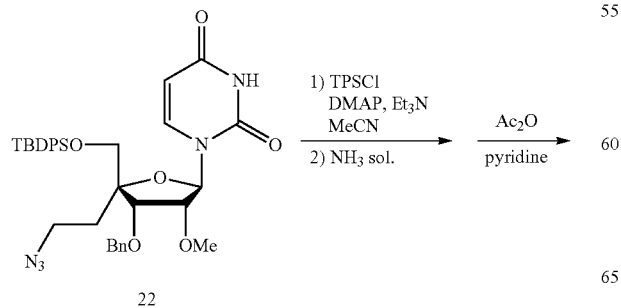

-continued

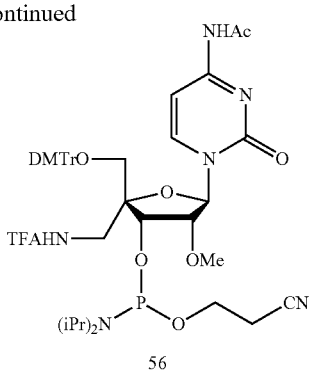

56

5'-O-[(1,1-dimethylethyl)diphenylsilyl]-4'-C-azidoethyl-3'-O-benzyl-2'-O-methyl-4-N-acetylcytosine 51

Triethylamine (Et₃N) (0.55 mL, 4.0 mmol), N,N-dimethyl-4-aminopyridine (DMAP) (367 mg, 3.0 mmol) and 2,4,6-triisopropyl benzenesulfonyl chloride (TPSCl) (606 mg, 3.0 mmol) were added in an argon atmosphere to an acetonitrile solution (10 mL) of 5'-O-[(1,1-dimethylethyl)diphenylsilyl]-4'-C-azidoethyl-3'-O-benzyl-2'-O-methyluridine (623.6 mg, 0.95 mmol), and stirred for 1 hour. Ammonia water (16 mL) was added to the reaction mixture, which was then stirred for 1.5 hours. The reaction mixture was then extracted with ethyl acetate, and the organic layer was washed with saturated saline. The organic layer was then dried with anhydrous sodium sulfate, filtered, and concentrated under reduced pressure. The residue was made into a pyridine solution (10 mL), acetic anhydride (0.19 mL, 2.0 mmol) was added, and the mixture was stirred for 1.5 hours. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [chloroform-methanol, 20:1, v/v] to obtain a target substance 51 (333.4 mg, 0.48 mmol, 50%).

$^1$H NMR (500 MHz, CDCl₃) δ: 1.11 (s, 9H), 1.75-1.78 (m, 1H), 2.20 (s, 3H), 2.42-2.45 (m, 1H), 3.32-3.38 (m, 2H), 3.68-3.73 (m, 2H), 4.04 (d, J=11.48 Hz, 1H), 4.34 (d, J=5.48 Hz, 1H), 4.46 (d, J=11.44 Hz, 1H), 4.63 (d, J=11.44 Hz, 1H), 6.12 (s, 1H), 6.90 (d, J=2.93 Hz), 7.31-7.48 (m, 12H), 7.55-7.66 (m, 4H), 8.33 (d, J=8.20 Hz, 1H), 8.74 (s, 1H)

5'-O-[(1,1-dimethylethyl)diphenylsilyl]-4'-C-azidoethyl-2'-O-methyl-4-N-acetylcytosine 52

A dichloromethane solution (10 mL) of 5'-O-[(1,1-dimethylethyl)diphenylsilyl]-4'-C-azidoethyl-3'-O-benzyl-2'-O-methyl-4-N-acetylcytosine (333.4 mg, 0.48 mmol) was cooled to −78° C. in an argon atmosphere, 1 M boron trichloride in dichloromethane (3.5 mL, 3.5 mmol) was added, and the mixture was stirred for 3 hours. The temperature was then raised to −30° C., and the mixture was stirred for 3 hours. The reaction mixture was extracted with dichloromethane, and the organic layer was washed with saturated sodium bicarbonate solution and saturated saline. The organic layer was then dried with anhydrous sodium sulfate, filtered, and concentrated under reduced pressure. The residue was purified by silica gel column chromatography [chloroform-methanol, 20:1, v/v] to obtain a target substance 52 (225.8 mg, 0.37 mmol, 78%).

$^1$H NMR (400 MHz, CDCl₃) δ: 1.12 (s, 9H), 1.71-1.75 (m, 1H), 2.13-2.21 (m, 4H), 2.85 (d, J=8.24 Hz, 1H), 3.28-3.41 (m, 2H), 3.64 (s, 3H), 3.71 (d, J=11.48 Hz, 1H), 3.82 (dd, J=3.68 Hz, 2.72 Hz, 1H), 3.97 (d, J=11.44 Hz, 1H), 4.52 (t, J=6.40 Hz, 1H), 6.12 (d, J=4.10 Hz, 1H), 7.41-7.51 (m, 6H), 7.63-7.66 (m, 4H), 8.5 (d, J=7.32 Hz, 1H), 8.47 (s, 1H)

4'-C-azidoethyl-2'-O-methyl-4-N-acetylcytosine 53

1 M tetrabutyl ammonium fluoride tetrahydrofuran solution (TBAF) (0.56 mL, 0.56 mmol) was added in an argon atmosphere to a tetrahydrofuran solution (5.0 mL) of 5'-O-[(1,1-dimethylethyl)diphenylsilyl]-4'-C-azidoethyl-2'-O-methyl-4-N-acetylcytosine (225.8 mg, 0.37 mmol), and stirred for 14 hours at room temperature. The solvent was then distilled off under reduced pressure, and the residue was purified by silica gel column chromatography [chloroform-methanol, 10:1, v/v] to obtain a target substance 53 (95.6 mg, 0.26 mmol, 70%).

$^1$H NMR (400 MHz, CDCl₃) δ: 1.87-1.91 (m, 1H), 2.10-2.17 (m, 1H), 2.25 (s, 3H), 2.94 (d, J=5.04 Hz, 1H), 3.43-3.47 (m, 1H), 3.54 (s, 3H), 3.65-3.83 (m, 3H), 4.42 (t, J=5.04 Hz, 1H), 4.50 (t, J=5.04 Hz, 1H), 5.63 (d, J=5.04 Hz, 1H), 7.44 (d, J=7.32 Hz, 1H), 8.02 (d, J=7.80 Hz, 1H), 8.90 (s, 11H)

5'-O-[bis(4-methoxyphenyl)phenylmethyl]-4'-C-azidoethyl-2'-O-methyl-4-N-acetylcytosine 54

4,4'-dimethoxytrityl chloride (DMTrCl) (847 mg, 2.5 mmol) was added in an argon atmosphere to a pyridine solution (30 mL) of 4'-C-azidoethyl-2'-O-methyl-4-N-acetylcytosine (570.5 mg, 1.55 mmol), and stirred for 18.5 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [chloroform-methanol, 20:1, v/v] to obtain a target substance 54 (948.9 mg, 1.41 mmol, 91%).

$^1$H NMR (500 MHz, CDCl₃) δ: 1.73-1.78 (m, 1H), 2.12-2.18 (m, 1H), 2.22 (s, 3H), 2.89 (d, J=6.45 Hz, 11H), 3.16-3.22 (m, 11H), 3.28-3.31 (m, 1H), 3.35 (d, J=10.9 Hz, 1H), 3.41 (d, J=10.9 Hz, 11H), 3.66 (s, 31H), 3.81 (s, 6H), 4.62 (s, 11H), 6.07 (d, J=1.70 Hz, 11H), 6.86 (d, J=8.00 Hz, 4H), 6.96 (d, J=8.70 Hz, 11H), 7.27-7.36 (m, 9H), 8.31 (d, J=7.45 Hz, 11H), 9.43 (s, 11H)

5'-O-[bis(4-methoxyphenyl)phenylmethyl]-4'-C-trifluoroacetylaminoethyl-2'-O-methyl-4-N-acetylcytosine 55

Triphenylphosphine (PPh₃) (918 mg, 3.5 mmol) and water (1.0 mL, 56 mmol) were added to a tetrahydrofuran solution (15 mL) of 5'-O-[bis(4-methoxyphenyl)phenylmethyl]-4'-C-azidoethyl-2'-O-methyl-4-N-acetylcytosine (948.9 mg, 1.41 mmol), and stirred for 22 hours at 45° C. The tetrahydrofuran in the reaction mixture was distilled off under reduced pressure, and a dichloromethane (10 mL) solution was obtained. Ethyl trifluoroacetate (CF₃COOEt) (0.5 mL, 4.2 mmol) and triethylamine (Et₃N) (0.30 mL, 2.1 mmol) were added, and stirred for 42 hours at room temperature. The reaction mixture was extracted with chloroform, and the organic layer was washed with saturated saline. The organic layer was then dried with anhydrous sodium sulfate, filtered, and concentrated under reduced pressure. The residue was purified by silica gel column chromatography [chloroform-methanol, 20:1, v/v] to obtain a target substance 55 (252.6 mg, 0.34 mmol, 25%).

$^1$H NMR (400 MHz, CDCl₃) δ: 1.89-1.96 (m, 1H), 2.07-2.14 (m, 1H), 2.21 (s, 3H), 3.12 (d, J=12.0 Hz, 1H), 3.25-3.29 (m, 1H), 3.31-3.41 (m, 4H), 3.62 (s, 3H), 3.81 (s, 6H), 3.90 (dd, J=2.76 Hz, 3.20 Hz, 1H), 4.54 (t, J=5.96 Hz, 1H), 6.12 (d, J=5.04 Hz, 1H), 6.85 (d, J=8.72 Hz, 4H), 6.99 (d, J=8.72 Hz, 1H), 7.27-7.36 (m, 7H), 8.20 (d, J=8.72 Hz, 1H), 8.84 (s, 1H)

57

5'-O-[bis(4-methoxyphenyl)phenylmethyl]-4'-C-trifluoroacetylaminoethyl-2'-O-methyl-3'-[2-cyanoethyl-N,N-bis(1-methylethyl)-phosphoramidite]-4-N-acetylcytosine 56

Diisopropyl ethylamine (DIPEA) (0.31 mL, 1.8 mmol) and 2-cyanoethyl N,N-diisopropylchlorophosphoramidite (CEP-Cl) (0.16 mL, 0.72 mmol) were added in an argon atmosphere to a tetrahydrofuran solution (2.5 mL) of 5'-O-[bis(4-methoxyphenyl)phenylmethyl]-4'-C-trifluoroacetylaminoethyl-2'-O-methyl-4-N-acetylcytosine (252.6 mg, 0.34 mmol), and stirred for 1.5 hours at room temperature. The reaction mixture was extracted with chloroform, and the organic layer was washed with saturated saline. The organic layer was then dried with anhydrous sodium sulfate, filtered, and concentrated under reduced pressure. The residue was purified by silica gel column chromatography [hexane-ethyl acetate, 1:5, v/v] to quantitatively obtain a target substance 56.

$^{31}$P NMR (162 MHz, CDCl$_3$) δ: 151.02, 151.61

Second Embodiment (Synthesis of 2'F-4' Aminoethyluridine Amidite Unit)

A 2'F-4' aminoethyluridine amidite unit was synthesized according to the following scheme.

[C16]

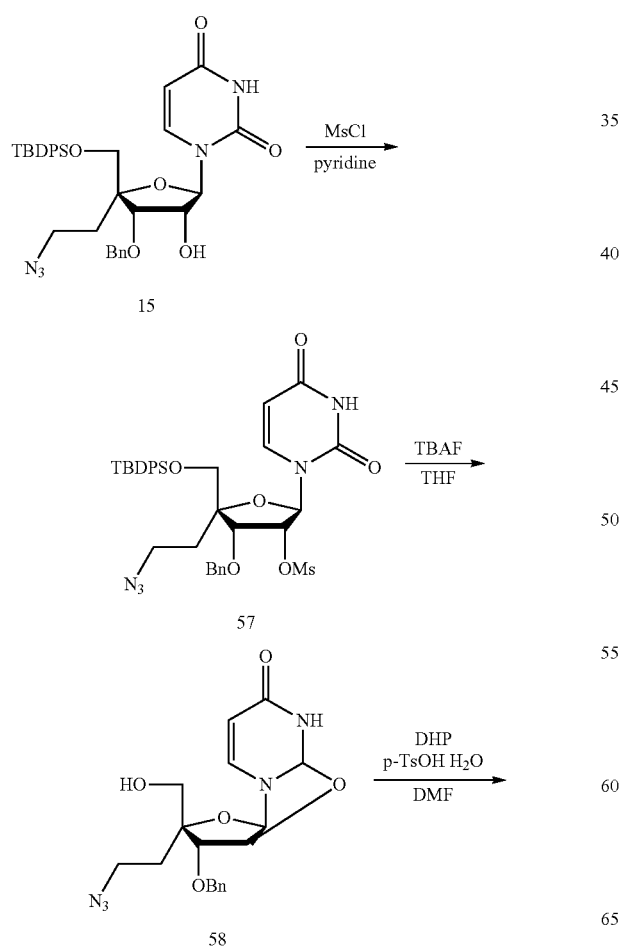

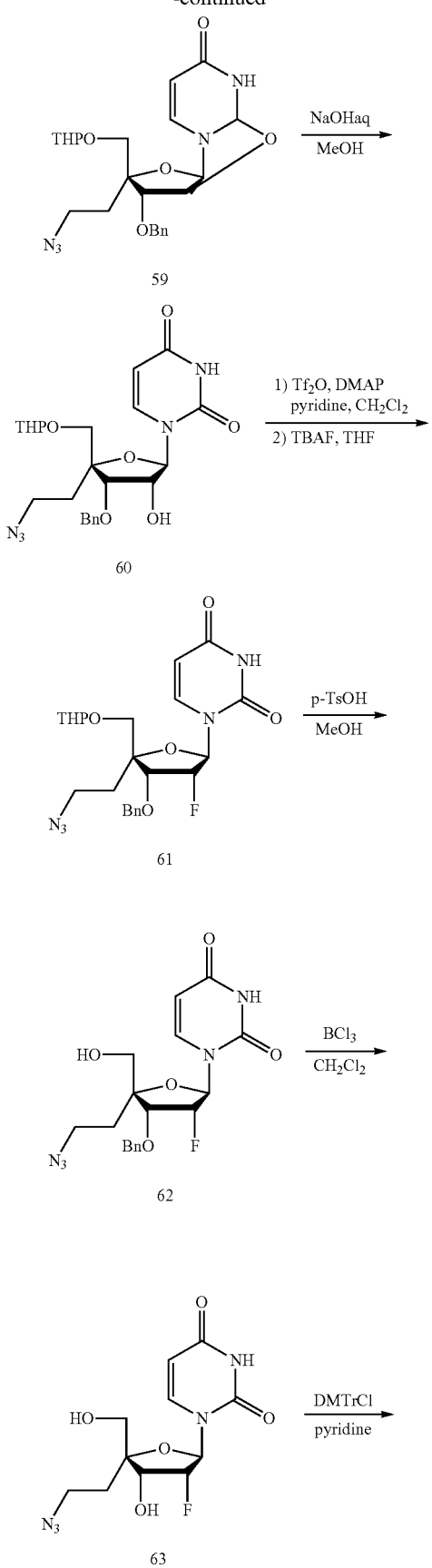

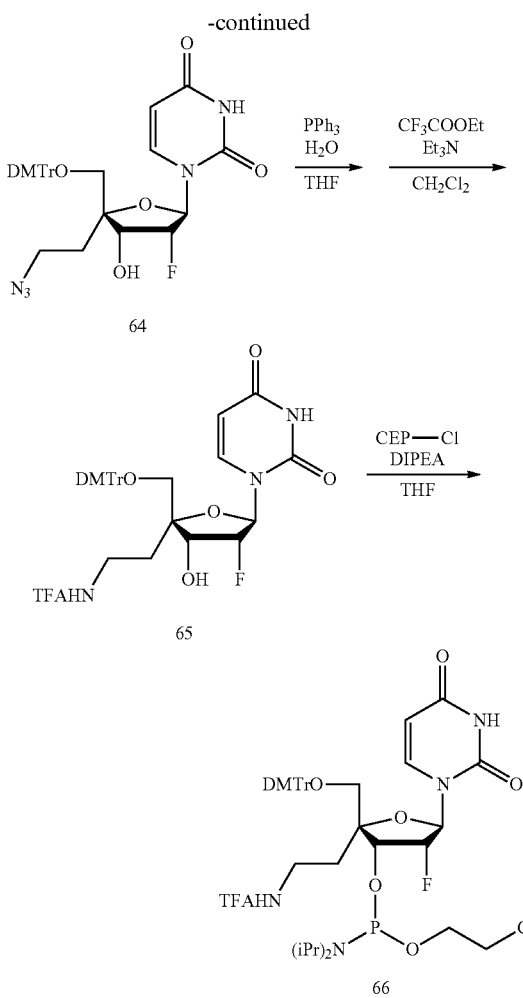

5'-O-[(1,1-dimethylethyl)diphenylsilyl]-4'-C-azidoethyl-3'-O-benzyl-2'-O-methanesulfonyluridine 57

Methanesulfonyl chloride (MsCl) (0.13 mL, 1.63 mmol) was dripped carefully into a pyridine solution (4.30 mL) of 5'-O-[(1,1-dimethylethyl)diphenylsilyl]-4'-C-azidoethyl-3'-O-benzyluridine (0.524 g 0.817 mmol) in an argon atmosphere in an ice bath, and stirred for 6 hours. The reaction product was extracted with chloroform, and the organic layer was washed with saturated sodium bicarbonate solution. The organic layer was then dried with anhydrous sodium sulfate, filtered, and concentrated under reduced pressure. The residue was purified by silica gel column chromatography [hexane-ethyl acetate, 1:1, v/v] to obtain a target substance 57 (0.585 g, 0.813 mmol, quant.).

$^1$H NMR (400 MHz, CDCl$_3$) δ: 1.10 (s, 9H), 1.67-1.75 (m, 1H), 2.07-2.14 (m, 1H), 3.14 (s, 3H), 3.26-3.37 (m, 2H), 3.59 (d, J=11.5 Hz, 1H), 3.91 (d, J=11.4 Hz, 1H), 4.36 (d, J=5.96 Hz, 1H), 4.48 (d, J=11.0 Hz, 1H), 4.84 (d, J=11.5 Hz, 1H), 5.29-5.33 (m, 2H), 6.13 (d, J=4.12 Hz, 1H), 7.34-7.40 (m, 9H), 7.42-7.49 (m, 2H), 7.55-7.57 (m, 2H), 7.60 (m, 2H), 7.69 (d, J=8.24 Hz, 1H), 8.30 (s, 1H)

4'-C-azidoethyl-3'-O-benzyl-2,2'-anhydrouridine 58

1 M tetrabutyl ammonium fluoride tetrahydrofuran solution (TBAF) (1.22 mL, 1.22 mmol) was added in an argon atmosphere to a tetrahydrofuran solution (6.0 mL) of 5'-O-[(1,1-dimethylethyl)diphenylsilyl]-4'-C-azidoethyl-3'-O-benzyl-2'-O-methanesulfonyluridine (0.585 g, 0.813 mmol), and stirred for 2 hours at room temperature. The solvent was then distilled off under reduced pressure, and the residue was purified by silica gel column chromatography [chloroform-methanol, 15:1, v/v] to obtain a target substance 58 (0.268 g, 0.696 mmol, 86%).

$^1$H NMR (400 MHz, CDCl$_3$) δ: 1.05-1.20 (m, 2H), 2.30-2.42 (m, 1H), 2.43-2.46 (m, 1H), 2.58 (t, J=7.80 Hz, 2H), 3.51 (s, 1H), 3.81 (d, J=11.5 Hz, 1H), 3.98 (d, J=11.9 Hz, 11H), 4.39 (t, J=5.04 Hz, 11H), 4.73 (d, J=5.96 Hz, 11H), 5.04 (d, J=7.36 Hz, 1H), 5.52 (d, J=5.96 Hz, 11H), 6.50-6.54 (m, 1H), 6.57-6.58 (m, 4H), 6.99 (d, J=7.36 Hz, 1H)

4'-C-azidoethyl-3'-O-benzyl-2'-deoxy-2'-fluorouridine 62

Dihydropyran (DHP) (15.3 mL, 169 mmol) and para-toluenesulfonic acid monohydrate (p-TsOH·H$_2$O) (1.36 g, 7.15 mmol) were added in an argon atmosphere in an ice bath to a dimethylformamide solution (45 mL) of 4'-C-azidoethyl-3'-O-benzyl-2,2'-anhydrouridine (2.50 g, 6.50 mmol), and stirred for 4 hours. The reaction product was neutralized with triethylamine, the solvent was distilled off under reduced pressure, and the residue was extracted with ethyl acetate and washed with saturated sodium bicarbonate solution. The organic layer was then dried with anhydrous sodium sulfate, filtered, and concentrated under reduced pressure. The residue was purified by silica gel column chromatography [chloroform-methanol, 15:1, v/v] to obtain a diastereomeric mixture (5'-O-tetrahydropyranyl-4'-C-azidoethyl-3'-O-benzyl-2,2'-anhydrouridine) 59 (2.74 g, 5.84 mmol, 90%).

Next, 1 M sodium hydroxide aqueous solution (10 mL) was added to a methanol solution (38 mL) of the diastereomeric mixture 59 (2.74 g, 5.84 mmol), and stirred for 3 hours at room temperature. The reaction product was neutralized with 1 M acetic acid, and the solvent was azeotroped with ethanol. The residue was purified by silica gel column chromatography [chloroform-methanol, 30:1, v/v] to obtain a diastereomeric mixture (5'-O-tetrahydropyranyl-4'-C-azidoethyl-3'-O-benzyl-arabinouridine) 60 (2.82 g, 5.78 mmol, quant.).

Pyridine (8.64 mL) and N,N-dimethyl-4-aminopyridine (DMAP) (3.82 g, 31.3 mmol) were added in an argon atmosphere to a dichloromethane solution (181 mL) of the diastereomeric mixture 60 (3.39 g, 6.95 mmol), which was then cooled to 0° C. Trifluoromethanesulfonic anhydride (Tf$_2$O) (3.42 mL, 20.9 mmol) was dripped carefully into the reaction mixture, which was then stirred for 1 hour at 0° C. The reaction product was extracted with chloroform, and the organic layer was washed with saturated sodium bicarbonate solution. The organic layer was then dried with anhydrous sodium sulfate, filtered, and concentrated under reduced pressure. The residue was azeotroped with acetonitrile, and made into a tetrahydrofuran solution (167 mL). A tetrahydrofuran solution (34.7 mL) of tetrabutylammonium fluoride (TBAF) (10.9 g, 3.06 mmol) was dripped in carefully in an ice bath in an argon atmosphere, and stirred for 1 hour at 0° C. The same amount of a tetrabutylammonium fluoride tetrahydrofuran solution (TBAF) (34.7 mL, 3.06 mmol) was dripped carefully into the reaction mixture, which was then stirred for 4 hours at 0° C. The reaction product was concentrated under reduced pressure, and the residue was extracted with chloroform and washed with saturated saline. The organic layer was then dried with anhydrous sodium sulfate, filtered, and concentrated under reduced pressure. The residue was purified by silica gel column chromatography [hexane-ethyl acetate, 1:2, v/v] to obtain a diastereomeric mixture (2.34 g, 4.78 mmol, 69%) of a target substance (5'-O-tetrahydropyranyl-4'-C-azidoethyl-3'-O-benzyl-2'-fluorouridine) 61.

Next, Para-toluenesulfonic acid monohydrate (p-TsOH·H$_2$O) (1.39 g, 7.47 mmol) was added in an argon atmosphere to a methanol solution (48.0 mL) of the diastereomeric mixture (2.34 g, 4.78 mmol), which was then stirred for 6 hours at room temperature. The reaction mixture was distilled under reduced pressure and azeotroped 3 times with pyridine, and the residue was purified by silica gel column chromatography [hexane-ethyl acetate, 5:2, v/v] to obtain a target substance 62 (1.36 g, 3.33 mmol, 70%).

$^1$H NMR (400 MHz, DMSO-d$_6$) δ: 1.78-1.86 (m, 1H), 1.99-2.06 (m, 1H), 3.42-3.48 (m, 3H), 3.60-3.64 (m, 1H), 4.36 (dd, J=19.3 Hz and 5.04 Hz, 1H), 4.62 (d, J=11.9 Hz, 1H), 4.70 (d, J=11.4 Hz, 1H), 5.36 (m, 0.5H), 5.42 (t, J=5.52 Hz, 1H), 5.50 (m, 0.5H), 5.65 (dd, J=7.80 Hz and 1.84 Hz, 1H), 6.04 (dd, J=17.9 Hz and 2.32 Hz, 1H), 7.31-7.35 (m, 1H), 7.36-7.37 (m, 4H), 7.91 (d, J=8.28 Hz, 1H), 11.4 (s, 1H)

$^{13}$C NMR (101 MHz, DMSO-d$_6$) δ: 30.38, 46.00, 63.09, 72.30, 76.61, 76.75, 86.68, 87.45, 87.79, 91.67, 93.55, 101.77, 127.47, 127.71, 128.33, 137.89, 140.90, 150.35, 163.15

$^{19}$F NMR (376 MHz, DMSO-d$_6$) δ: −120.08, −119.88

4'-C-azidoethyl-2'-deoxy-2'-fluorouridine 63

A dichloromethane solution (27 mL) of 4'-C-azidoethyl-3'-O-benzyl-2'-deoxy-2'-fluorouridine (0.672 g, 1.66 mmol) was cooled to −78° C. in an argon atmosphere, 1 M boron trichloride in dichloromethane (13.3 mL, 13.3 mmol) was added, and the mixture was stirred for 3 hours. The temperature was then raised to −30° C., and the mixture was stirred for 5 hours. Dichloromethane-methanol (1:1 v/v, 25 mL) was added to the reaction mixture, which was then concentrated under reduced pressure. The residue was purified by silica gel column chromatography [chloroform-methanol, 8:1, v/v] to obtain a target substance 63 (339 mg, 1.08 mmol, 65%).

$^1$H NMR (400 MHz, DMSO-d$_6$) δ: 1.74-1.79 (m, 1H), 1.81-2.01 (m, 1H), 3.38-3.45 (m, 3H), 3.55 (dd, J=11.9 Hz and 5.04 Hz, 1H), 4.26-4.32 (m, 1H), 5.10 (t, J=5.04 Hz, 0.5H), 5.23 (t, J=5.04 Hz, 1H), 5.35 (t, J=5.04 Hz, 1H), 5.66 (d, J=7.80 Hz, 1H), 5.79 (d, J=5.52 Hz, 1H), 6.05 (dd, J=15.1 Hz and 4.12 Hz, 1H), 7.90 (d, J=8.24 Hz, 1H), 11.4 (s, 1H)

$^{13}$C NMR (101 MHz, DMSO-d$_6$) δ: 30.44, 46.15, 63.40, 69.37, 69.53, 79.20, 85.81, 86.13, 87.10, 92.26, 94.13, 102.09, 140.61, 150.53, 163.09

$^{19}$F NMR (376 MHz, DMSO-d$_6$) δ−123.84, −123.97

5'-O-[bis(4-methoxyphenyl)phenylmethyl]-4'-C-azidoethyl-2'-deoxy-2'-fluorouridine 64

4,4'-dimethoxytrityl chloride (DMTrCl) (554 mg, 1.64 mmol) was added in an argon atmosphere to a pyridine solution (4.0 mL) of 4'-C-azidoethyl-2'-deoxy-2'-fluorouridine (343 mg, 1.09 mmol), and stirred for 6 hours at room temperature. The reaction mixture was extracted with ethyl acetate, and the organic layer was washed with saturated sodium bicarbonate solution and saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 64 (615 mg, 0.996 mmol, 91%).

$^1$H NMR (400 MHz, CDCl$_3$) δ: 1.85-1.93 (m, 1H), 2.02-2.09 (m, 1H), 2.78 (s, 1H), 3.21-3.27 (m, 1H), 3.31-3.40 (m, 3H), 3.80 (s, 6H), 4.60-4.64 (m, 1H), 5.10 (t, J=1.84 Hz, 0.5H), 5.25 (t, J=1.60 Hz, 0.5H), 5.36 (d, J=8.24 Hz, 1H), 6.14 (dd, J=15.6 Hz and 3.20 Hz, 1H), 6.85 (d, J=8.72 Hz, 4H), 7.24 (s, 3H), 7.27-7.36 (m, 6H), 7.65 (d, J=7.80 Hz, 1H), 8.99 (s, 1H)

$^{13}$C NMR (101 MHz, CDCl$_3$) δ: 31.16, 46.51, 55.41, 65.70, 71.48, 71.63, 86.97, 87.19, 87.52, 87.76, 92.90, 94.80, 102.96, 113.52, 127.47, 128.23, 128.26, 130.24, 130.28, 134.82, 135.00, 140.50, 144.08, 150.18, 158.96, 163.02

$^{19}$F NMR (376 MHz, CDCl$_3$) δ: −122.41, −122.67

5'-O-[bis(4-methoxyphenyl)phenylmethyl]-4'-C-trifluoroacetylaminoethyl-2'-deoxy-2'-fluorouridine 65

Triphenylphosphine (PPh$_3$) (654 mg, 2.49 mmol) and water (0.719 mL) were added to a tetrahydrofuran solution (25 mL) of 5'-O-[bis(4-methoxyphenyl)phenylmethyl]-4'-C-azidoethyl-2'-deoxy-2'-fluorouridine (616 mg, 0.997 mmol), and stirred for 15 hours at 45° C. The tetrahydrofuran in the reaction mixture was distilled off under reduced pressure, and a dichloromethane solution (6.0 mL) was obtained. Ethyl trifluoroacetate (CF$_3$COOEt) (0.35 mL, 2.93 mmol) and triethylamine (Et$_3$N) (0.203 mL, 1.47 mmol) were added, and stirred overnight at room temperature. The reaction mixture was extracted with ethyl acetate, and the organic layer was washed with saturated saline. The organic layer was then dried with anhydrous sodium sulfate, filtered, and concentrated under reduced pressure. The residue was purified by silica gel column chromatography [hexane-ethyl acetate, 2:3, v/v] to obtain a target substance 65 (610 mg, 0.887 mmol, 91%).

$^1$H NMR (400 MHz, CDCl$_3$) δ: 1.90-2.11 (m, 2H), 3.31-3.42 (m, 4H), 3.80 (s, 6H), 4.60 (dd, J=13.8 Hz amd 5.04 Hz, 1H), 5.14 (t, J=4.56 Hz, 0.5H), 5.28 (s, 0.5H), 5.41 (d, J=7.80 Hz, 1H), 6.15 (dd, J=15.1 Hz and 3.64 Hz, 1H), 6.86 (d, J=7.80 Hz, 4H), 7.28-7.37 (m, 10H), 7.63 (d, J=8.28 Hz, 1H), 9.55 (s, 1H)

$^{13}$C NMR (101 MHz, CDCl$_3$) δ: 30.94, 35.33, 55.38, 65.76, 71.47, 71.62, 87.15, 87.36, 87.83, 92.63, 94.52, 103.11, 113.53, 117.35, 127.47, 128.18, 128.26, 130.23, 134.71, 134.90, 140.58, 143.99, 150.54, 157.12, 157.48, 158.92, 163.34

$^{19}$F NMR (376 MHz, CDCl$_3$) δ: −124.43, −124.56

5'-O-[bis(4-methoxyphenyl)phenylmethyl]-4'-C-trifluoroacetylaminoethyl-2'-deoxy-2'-fluoro-3'-[2-cyanoethyl-N,N-bis(1-methylethyl)-phosphoramidite]-uridine 66

Diisopropyl ethylamine (DIPEA) (0.713 mL, 409 mmol) and 2-cyanoethyl N,N-diisopropylchlorophosphoramidite (CEP-Cl) (0.365 mL, 1.63 mmol) were added in an argon atmosphere to a tetrahydrofuran solution (6 mL) of 5'-O-[bis(4-methoxyphenyl)phenylmethyl]-4'-C-trifluoroacetylaminoethyl-2'-deoxy-2'-fluorouridine (562 mg, 0.817 mmol), and stirred for 1 hour at room temperature. The reaction mixture was extracted with chloroform, and the organic layer was washed with saturated saline. The organic layer was then dried with anhydrous sodium sulfate, filtered, and concentrated under reduced pressure. The residue was purified by silica gel column chromatography [hexane-ethyl acetate, 1:1, v/v] to obtain a target substance 66 (696 mg, 0.784 mmol, 96%).

$^{31}$P NMR (162 MHz, CDCl$_3$) δ: 151.16, 151.69, 152.64, 152.72

Third Embodiment (Synthesis of RNA oligomer containing aminoalkyl RNA)

Oligonucleotides were synthesized using the nucleosides synthesized in First Embodiment and Second Embodiment. The oligonucleotides were synthesized with an automatic nucleic acid synthesizer using the phosphoramidite method. Synthesis was performed using 0.1 to 0.15 M acetonitrile solutions of the nucleoside amidites and nucleotides supported on CPG carriers. After completion of synthesis, the CPG resin was transferred to a sampling tube, and shaken for 5 minutes after addition of acetonitrile-diethylamine (9:1, v/v, 1.0 mL). The supernatant was removed, ammonia water-methylamine (1:1, v/v, 1.0 mL) was added, and the mixture was left standing for 10 minutes at 65° C. The reaction mixture was made up to 10 mL with 0.1 M triethylamine-acetic acid buffer (TEAA), and adsorbed through an equilibrated Sep-Pac tC18 reverse-phase column. The column was washed with sterile water and eluted with acetonitrile-water (1:1, v/v, 3 mL), and the pressure was reduced to dryness to produce a crude product. The crude product was dissolved in loading solution (1×TBE in 90% formamide) (200 μL, and purified by 20% PAGE (500 V, 20 mA). 0.1 M triethylamine-acetic acid buffer and 1 mM ethylenediamine tetraacetic acid (EDTA) aqueous solution (20 mL) were added, and shaken overnight. After shaking, the filtrate was adsorbed through an equilibrated Sep-Pac tC18 reverse-phase column. The column was washed with sterile water to remove salts and eluted with acetonitrile-water (1:1, v/v, 3 mL), and the pressure was reduced to dryness.

The oligonucleotide was dissolved in sterile water (1 mL), and the yield was determined from the absorbance of the diluted solution at 260 nm, 60 μmol equivalents of the oligonucleotide were dried under reduced pressure, thoroughly mixed with 3 μL of sterile water and 3 μL of matrix solution and then dried on a plate, and the mass was measured by MALDI-TOF/MS.

Figure 2:
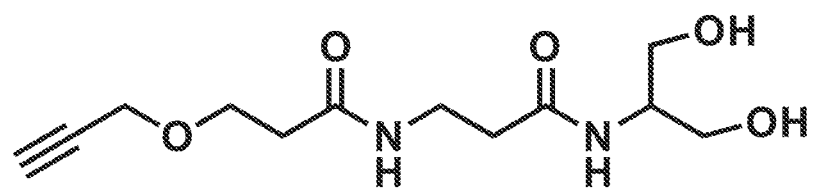
FIG. 2 shows the structure of a linker.

The synthesized sequences (SEQ ID NO:1 for oligoribonucleotide and SEQ ID NO:2 for oligodeoxyribonucleotide) and the results for yield and mass measurement are shown in the tables below. In the tables, $u^{AE}$ represents 2'-OMe-4'-AEU, $u^{AM}$ 2'-OMe-4'-AMU, $u^{GM}$ 2'-OMe-4'-GMU, $u^{AP}$ 2'-OMe-4'-APU, and $u^{FAE}$ 2'-F-4'-AEU. The structures of these are shown in FIG. 1. F represents fluorescein introduced as a fluorescent label, and the lower-case letters a, u, c and g indicate 2'-OMe modified forms of U, A and G, respectively. An alkyne-serinol linker was also introduced at the 3' end, and used as a scaffold for binding DDS molecules by a click reaction. The linker is shown in FIG. 2.

TABLE 1

Base sequences of synthesized oligonucleotides

| ON1  | 5' - F UUC UUC UUC UUS -3' |
| ON2  | 5' - F Uu$^{AE}$C UUC u$^{AE}$UC Uu$^{AE}$S -3' |
| ON3  | 5' - F UUC UUC Uu$^{AE}$C u$^{AE}$u$^{AE}$S -3' |
| ON4  | 5' - F u$^{AE}$u$^{AE}$C u$^{AE}$UC u$^{AE}$UC u$^{AE}$u$^{AE}$S -3' |
| ON5  | 5' - F uuC uUC uUC uuS-3' |
| ON6  | 5' - AAG AAG AAG AA-3' |
| ON7  | 5' - aag aag aag aa -3' |
| ON8  | 5' - F Uu$^{AM}$C UUC u$^{AM}$UC Uu$^{AM}$S -3' |
| ON9  | 5' - F Uu$^{GM}$C UUC u$^{GM}$UC Uu$^{GM}$S -3' |
| ON10 | 5' - F Uu$^{AP}$C UUC u$^{AP}$UC Uu$^{AP}$S -3' |
| ON11 | 5' - F uu$^{AP}$c uuc u$^{AP}$uc uu$^{AP}$S -3' |

TABLE 1-continued

Base sequences of synthesized oligonucleotides

| ON12 | 5' - F UUC UUC UUC UU -3' |
| ON13 | 5' - F Uu$^{AE}$C UUC u$^{AE}$UC Uu$^{AE}$ -3' |
| ON14 | 5' - F Uu$^{tAt}$C UUC u$^{tAt}$UC Uu$^{tAt}$ -3' |
| ON15 | 5' - F Uu$^{AP}$C UUC u$^{AP}$UC Uu$^{AP}$ -3' |

TABLE 2

Properties of Synthesized oligonucleotides

| name | calculated mass | observed mass | OD 260 | C (mM) |
|---|---|---|---|---|
| ON1  | 4175.6 | 4174.7 | 9.71  | 99.5  |
| ON2  | 4346.9 | 4346.0 | 7.20  | 74.0  |
| ON3  | 4346.9 | 4346.1 | 7.62  | 78.1  |
| ON4  | 4518.2 | 4518.4 | 6.10  | 62.5  |
| ON5  | 4259.8 | 4259.0 | 16.0  | 163.9 |
| ON6  | 3607.3 | 3606.8 | 12.5  | 93.8  |
| ON7  | 3761.6 | 3761.1 | 5.76  | 43.2  |
| ON8  | 4304.9 | 4303.9 | 7.84  | 80.3  |
| ON9  | 4430.9 | 4429.6 | 1.51  | 15.5  |
| ON10 | 4389.0 | 4388.0 | 15.0  | 153.7 |
| ON11 | 4501.2 | 4499.6 | 11.5  | 117.8 |
| ON12 | 3841.4 | 3842.9 | 11.4  | 116.8 |
| ON13 | 4012.7 | 4013.0 | 6.00  | 61.5  |
| ON14 | 3976.6 | 3977.1 | 2.30  | 23.6  |
| ON15 | 4054.7 | 4053.3 | 25.1  | 257.2 |

Fourth Embodiment (Measurement of Melting Temperature ($T_m$))

3 μM of the following RNA duplexes, which had been annealed in 10 mM phosphate buffer (pH 7.0, 100 mM NaCl), were heated from 5° C. to 70° C. at a rate of +0.5° C./min, and the melting temperature ($T_m$) was calculated from the change in absorbance. The results are shown in FIGS. 3 and 4.

Figure 3:
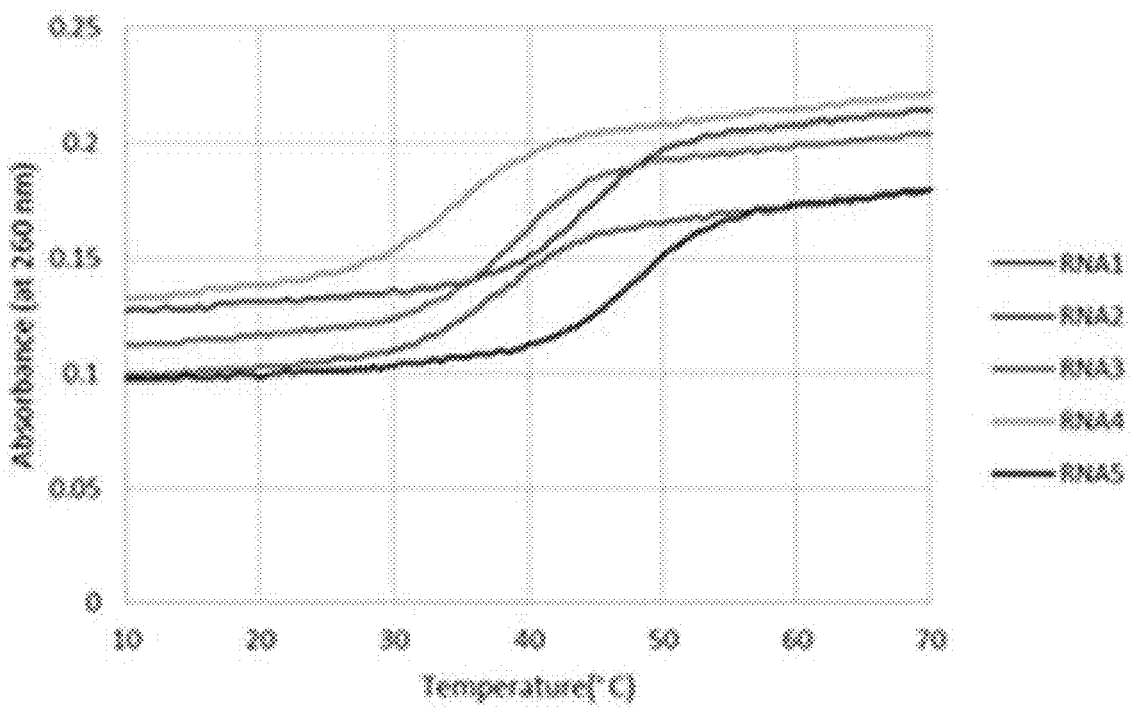
FIG. 3 shows the results of an evaluation of oligonucleotide melting temperature.
Figure 4:
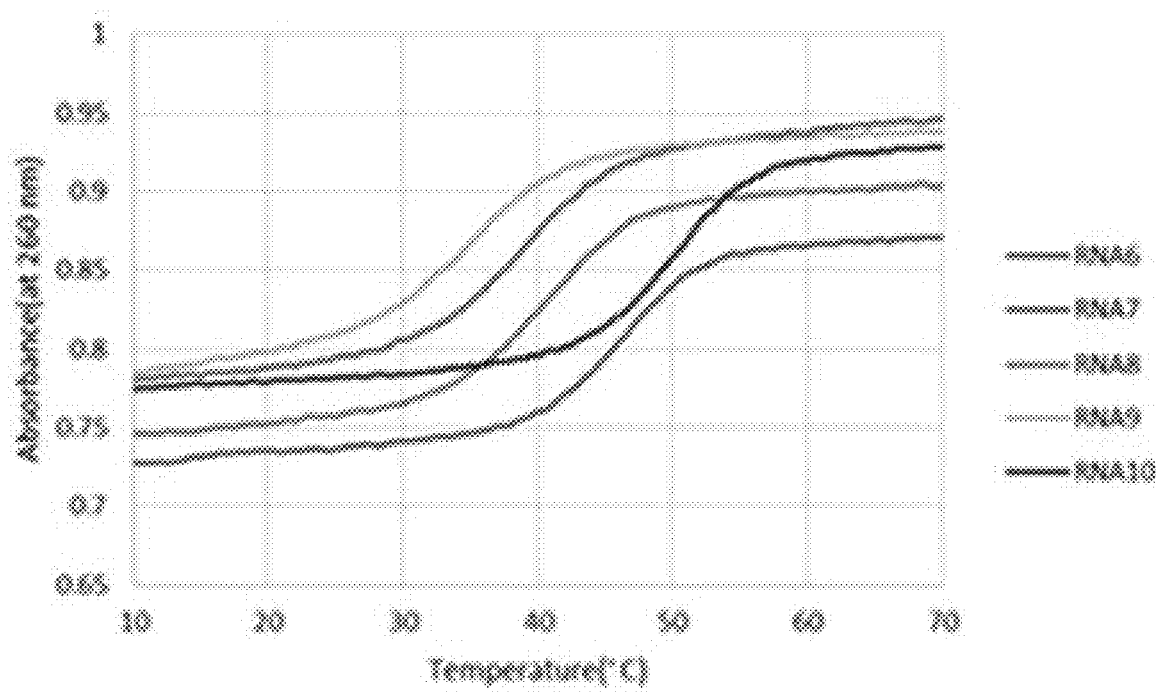
FIG. 4 shows the results of an evaluation of oligonucleotide melting temperature.

As shown in FIG. 3, a decrease in ability to form RNA duplexes was confirmed as a result of aminoethyl modification. The melting temperature of the complement strand decreased by about 2° C. per modification regardless of whether the 2' position was —OH or —OMe.

Fifth Embodiment (Ribonuclease Resistance Test in Bovine Serum)

300 μmol of the fluorescent labeled oligonucleotide synthesized in Third Embodiment was dissolved in 37.5 μL of OPTI-MEM sterile water, and incubated at 37° C. after addition of 1.2 μL of bovine serum as a ribonuclease source. After 0, 0.5, 1, 3, 6, 12 and 24 hours, 1.2 μL of the reaction solution was mixed with 5 μL of loading solution (containing 9 M urea) to terminate the reaction. This reaction solution was separated with 20% PAGE at 500 V, 20 mA, and analyzed with a LAS4000 Lumino Image Analyzer. The results are shown in FIGS. 5 and 6.

Figure 5:
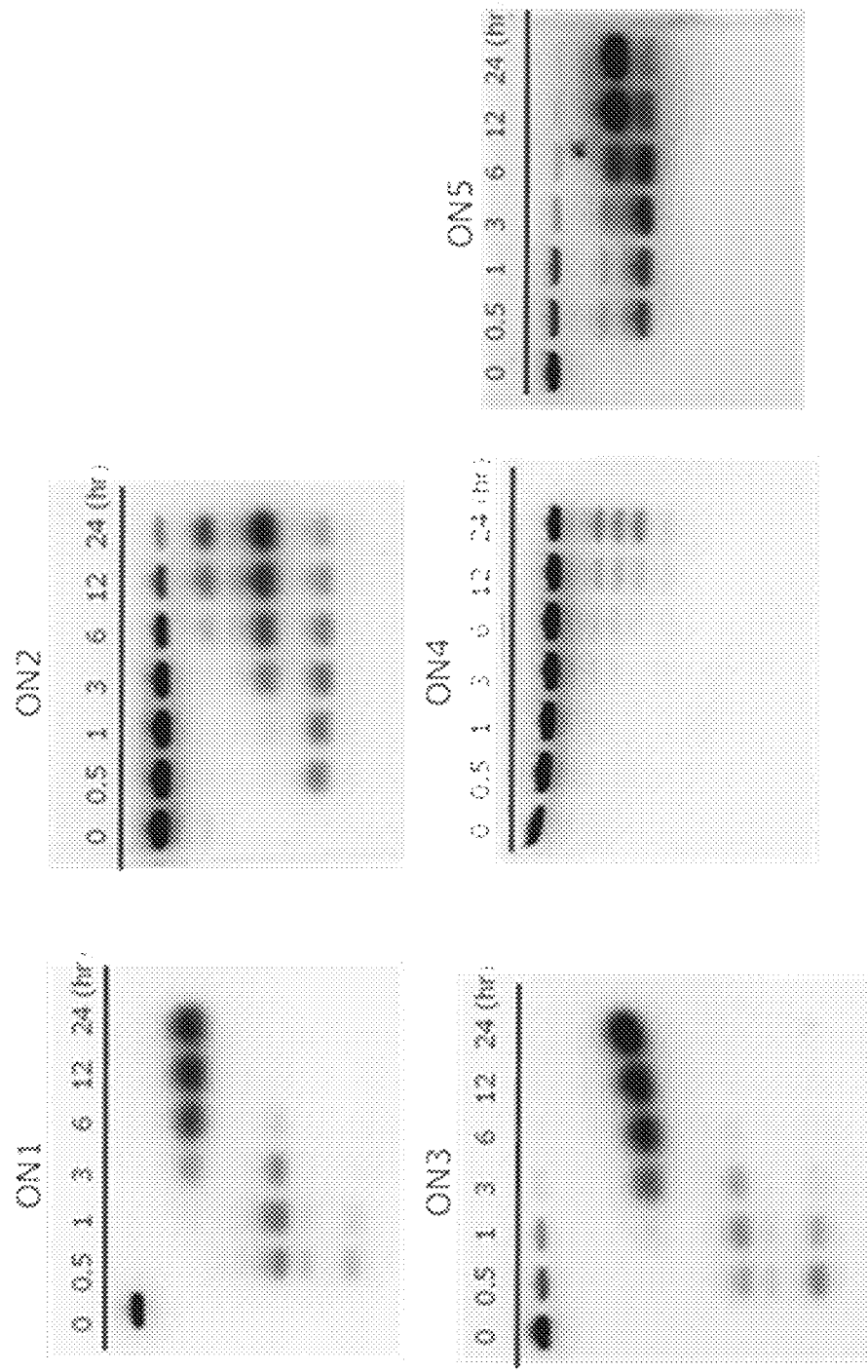
FIG. 5 shows the results of an evaluation of ribonuclease resistance.

As shown in FIG. 5, ribonuclease resistance was first compared according to aminoethyl modification site. In the unmodified ON1 and the ON3 having modifications concentrated at the 3' end, decomposition was mostly complete within 0 to 1 hours, but a decrease in decomposition speed was observed with ON2 and ON4 having aminoethyl modifications introduced uniformly and ON5 having all 2'-OMe modifications. Although decomposition was mostly complete within 6 hours with the 2'-OMe modifications, the presence of full-length RNA was confirmed even after 24 hours with ON2 and ON4. In particular, almost no decomposition products were seen even after 6 hours with ON4 having modifications evenly distributed in 6 locations, confirming that aminoalkyl modification produces strong ribonuclease resistance.

Figure 6:
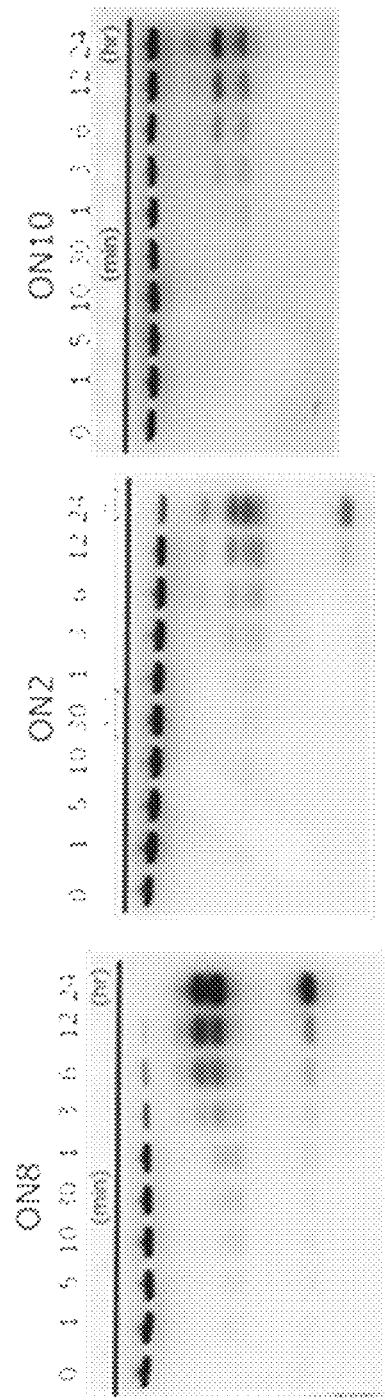
FIG. 6 shows the results of another evaluation of ribonuclease resistance.

Next, as shown in FIG. 6, ribonuclease resistance was compared according to differences in the chain length of the aminoalkyl side chains. As a result, it was confirmed that the decomposition rate of the oligonucleotide declined. That is, it was confirmed that ribonuclease resistance increased as the chain length of the introduced alkyl chain increased from an aminomethyl group (ON8) to an aminoethyl group (ON2) to an aminopropyl group (ON10).

Sixth Embodiment (Cell Membrane Permeability Test)

HeLa cells were prepared to 20,000 cell/mL, added 400 μL per well to a 48-well plate, and cultured for 24 hours. 40 μmol of the fluorescent-labeled oligonucleotide was dissolved in OPTI-MEM (400 μL), and the entire amount was added to the wells after the medium in each well had been aspirated. This was incubated for 1 hour, and 200 μL/well of the culture medium containing serum was added (D-MEM containing 10% BS, Wako Pure Chemical Industries, Ltd.). After 24 hours, the medium was removed from each well, and the wells were washed twice with PBS. The cells were then observed with an inverted fluorescence microscope (IX70, Olympus Corporation). The results are shown in FIGS. 7 and 8.

As shown in FIG. 7, there was a dramatic increase in cell membrane permeability due to aminoethyl modification. In particular, extremely high cellular uptake was confirmed in the case of ON2, even though this was only modified at 3 locations on the 11-mer. Looking at the modified locations, no membrane permeability was seen in ON3 having modifications at the 3' end suggesting that the aminoethyl modifications must be distributed uniformly in the sequence.

Figure 8:
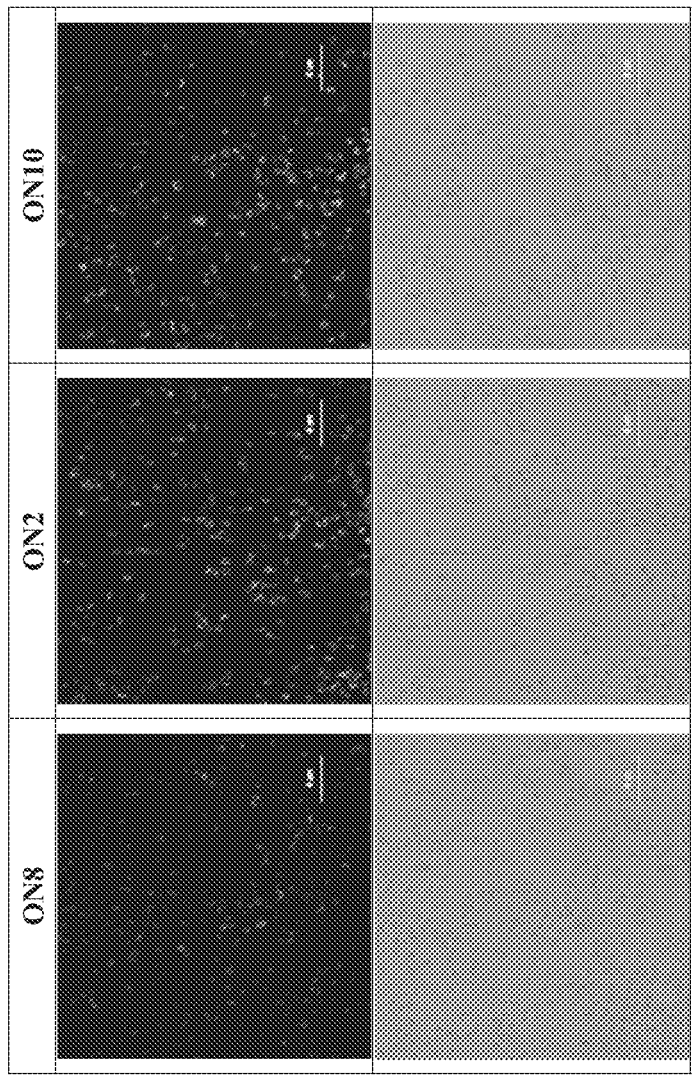
FIG. 8 shows the results of another evaluation of cell membrane permeability due to aminoalkyl group modification.

As shown in FIG. 8, the cell membrane permeability of the oligonucleotide was compared next depending on differences in the chain length of the introduced aminoalkyl side chains. As a result, cell membrane permeability was confirmed to be higher in the oligonucleotides having introduced aminoethyl (ON2) and aminopropyl (ON10) groups in comparison with the oligonucleotide (ON8) having an introduced aminomethyl group. This can be attributed to an increase in lipid solubility caused by the ethyl and propyl groups, or an increase in Van der Waals intermolecular force.

Seventh Embodiment (Verifying RNA Interference Ability)

2'-fluoroaminoethyl modified siRNA and 2'-O-methylaminoethyl modified siRNA were synthesized in accordance with Third Embodiment using the 2'-fluoroaminoethyl uridine and 2'-O-methylaminoethyl uridine synthesized in First Embodiment and Second Embodiment and their derivatives as the uridine in the passenger strand of the siRNA duplex shown below.

[C17]
P-strand
5'- GGCCUUUCACUACUCCUACUU-3'

G-strand
3'-UUCCGGAAAGUGAUGAGGAUG -5'

The RNA interference ability of the aminoethyl modified siRNA was evaluated by a dual luciferase reporter assay. HeLa cells (Firefly luciferase, *Renilla* luciferase stable expression strain) were prepared to $8.0 \times 10^3$ cells/mL, and 100 μL was added to each well of a 96-well plate, and cultured for 24 hours. The respective chains of the synthesized siRNA were dissolved in 10 μl of TE buffer, heated for 3 minutes at 95° C., and left for at least 1 hour to cool to room temperature. Each amount of this siRNA, each amount of the medium (OPTI-MEM), and 1.5 μL of lipofectamin RNAiMAX (transfection reagent) were mixed to a total of 50 μL and added 10 μL per well to the 96-well plate from which the medium had been aspirated, and after 20 minutes in a $CO_2$ incubator at 37° C., 50 μl of medium was added and the cells were cultured for 24 hours in a $CO_2$ incubator at 37° C. After 24 hours the medium was aspirated, and the cells were cold stored. The siRNA was evaluated at two concentrations of 1 nM and 10 nM. Natural siRNA was also treated in the same way as a positive control.

Luciferase luminescence was measured by adding 24 μL of Dual glo substrate (Firefly luciferase substrate) to the thawed cells and leaving them standing for 5 minutes, then transferring 23 μL of sample to a 96-well plate for measuring luminescence, and measuring Firefly luciferase. After this, 23 μL of Stop and glo substrate (*Renilla* luciferase substrate) was added, the cells were left standing for 10 minutes, and *Renilla* luciferase was measured. The measured value for *Renilla* luciferase fluorescence was divided by the value for Firefly luciferase, and compared using % of control. A Luminescenser JNR II was used for luciferase measurement. The results are shown in FIG. 9.

Figure 9:
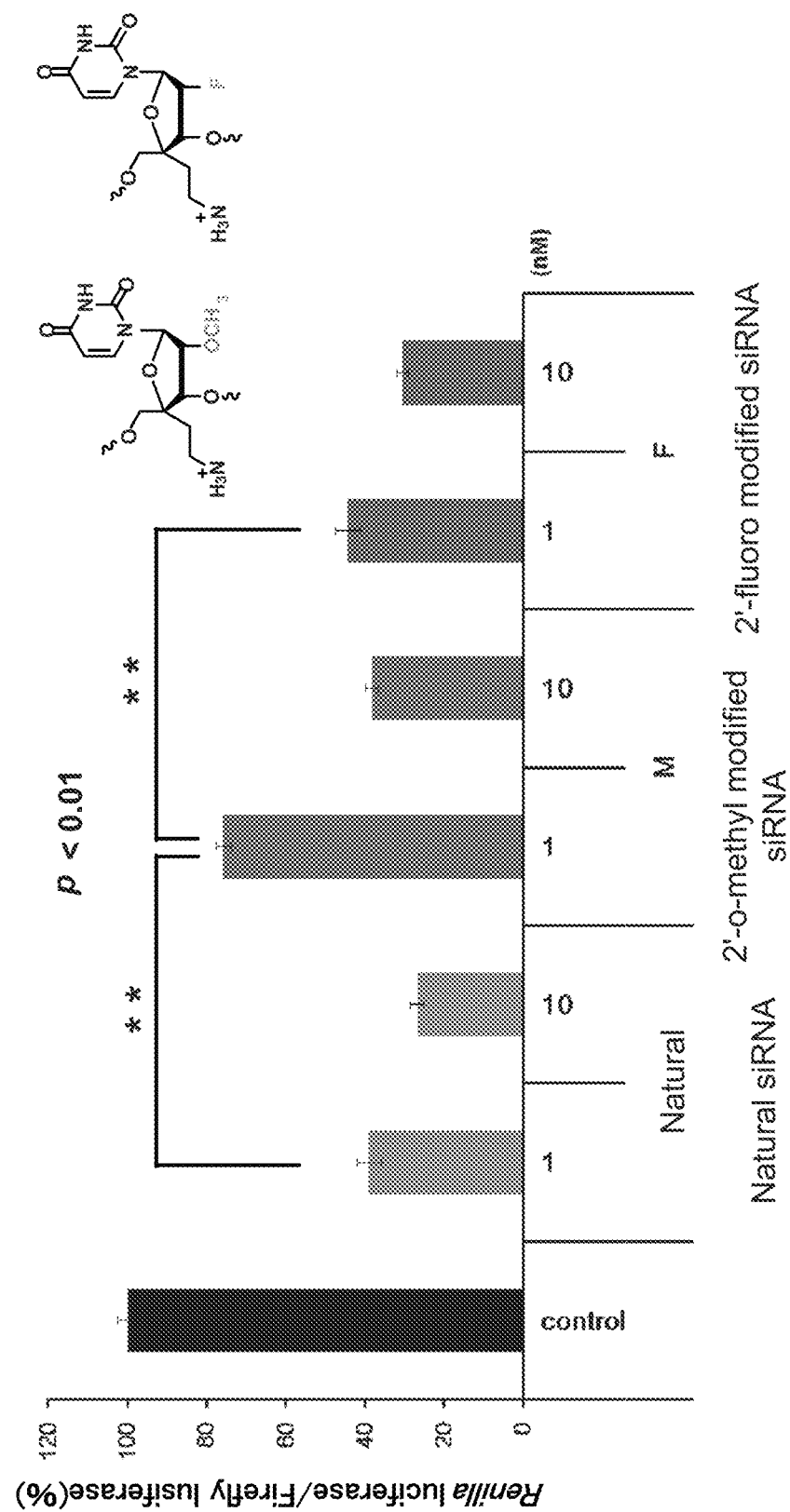
FIG. 9 shows the results of an evaluation of RNAi activity obtained with siRNA in which the uridine unit of the passenger strand is replaced with 2'-fluoroaminoethyluridine or 2'-O-methylaminoethyluridine.

As shown in FIG. 9, both the 2'-fluoroaminoethyl modified siRNA and 2'-O-methylaminoethyl modified siRNA exhibited the ability to suppress gene expression. In particular, the 2'-fluoroaminoethyl modified siRNA exhibited gene expression suppression ability equivalent to that of the natural siRNA used as a positive control.

CITATION LIST

Non-Patent Literature 1: HELVETICA CHIMICA ACTA Vol. 83 (2000) 128-151

Non-Patent Literature 2: The Journal of Organic Chemistry 2012, 77, 3233-3245

Non-Patent Literature 3: Bioorganic & Chemistry letters (1999)2667-2672

Non-Patent Literature 4: The Journal of Organic Chemistry 2013, 78, 9956-9962

SEQUENCE LISTING FREE TEXT

SEQ IDs 1-4: siRNA

The invention claimed is:

1. An oligonucleotide comprising a nucleoside derivative represented by formula (2) below, or a salt thereof,

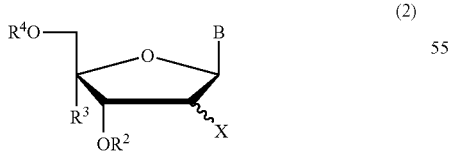

wherein:
X represents a fluorine atom,
$R^2$ and $R^4$ may be the same or different, and each represents:
a hydrogen atom,
a hydroxyl protecting group,
a phosphate group,
a protected phosphate group, or
—$P(=O)_n R^5 R^6$ in which n is 0 or 1, and $R^5$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group, but when n is 1, $R^5$ and $R^6$ are not both hydrogen atoms,
$R^3$ represents:
$NHR^7$ in which $R^7$ represents a hydrogen atom, an alkyl group, an alkenyl group or a protecting group for an amino group,
an azide group,
an amidino group, or
a guanidino group,
each having a linking group, but when $R^7$ is hydrogen atom or a protecting group for an amino group, the linking group is an alkylene group which has 2 to 3 carbon atoms, and
B represents a nucleobase.

2. The oligonucleotide of claim 1, wherein said oligonucleotide is selected from the group consisting of a DNA molecule, a RNA molecule, and a duplex comprising a DNA and/or a RNA molecule.

3. The oligonucleotide of claim 1, wherein said oligonucleotide comprises a nucleoside derivative represented by the structure:

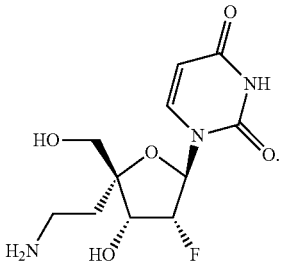

4. An RNA molecule comprising an oligoribonucleotide derivative represented by formula (2) below, or a salt thereof,

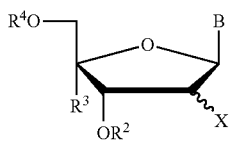

(2)

wherein:
X represents a fluorine atom,
$R^2$ and $R^4$ may be the same or different, and each represents:
a hydrogen atom,
a hydroxyl protection group,
a phosphate group,
a protected phosphate group, or
—P(=O)$_n$R$^5$R$^6$ in which n is 0 or 1, and $R^5$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group, but when n is 1, $R^5$ and $R^6$ are not both hydrogen atoms,
$R^3$ represents:
NHR$^7$ in which R$^7$ represents a hydrogen atom, an alkyl group, an alkenyl group or a protecting group for an amino group,
an azide group,
an amidino group, or
a guanidino group,
each having a linking group, but when R$^7$ is hydrogen atom, the linking group is an alkylene group which has 2 to 3 carbon atoms, and
B represents any of a purine-9-yl group, 2-oxo-pyrimidin-1-yl group, substituted purine-9-yl group or substituted 2-oxo-pyrimidin-1-yl group; and
wherein said RNA molecule consists of an RNA interference agent.

5. The RNA molecule of claim 4, wherein said RNA molecule consists of a siRNA.

6. The RNA molecule according to claim 4, wherein R$^7$ represents a hydrogen atom.

7. The RNA molecule according to claim 4, wherein the nucleoside derivative comprises the structure:

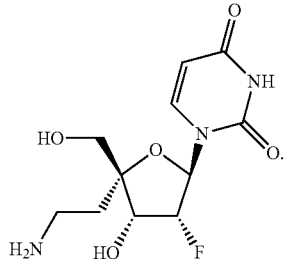 [SMILES: NCC[C@]1(CO)O[C@@H](n2ccc(=O)[nH]c2=O)[C@H](F)[C@@H]1O]

* * * * *